United States Patent
Wang et al.

(10) Patent No.: US 7,960,406 B2
(45) Date of Patent: Jun. 14, 2011

(54) DIKETO SUBSTITUTED PYRROLO[2,3-C] PYRIDINES

(75) Inventors: Tao Wang, Farmington, CT (US); Yasutsugu Ueda, Clinton, CT (US); Lawrence G. Hamann, North Grafton, MA (US); Zhongxing Zhang, Madison, CT (US); Zhiwei Yin, Glastonbury, CT (US); Alicia Regueiro-Ren, Middletown, CT (US); David J. Carini, Wallingford, CT (US); Jacob Swidorski, Southington, CT (US); Zheng Liu, Beacon Falls, CT (US); Barry L. Johnson, Wallingford, CT (US); Nicholas A. Meanwell, East Hampton, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/490,714

(22) Filed: Jun. 24, 2009

(65) Prior Publication Data
US 2010/0009993 A1    Jan. 14, 2010

Related U.S. Application Data

(60) Provisional application No. 61/075,374, filed on Jun. 25, 2008.

(51) Int. Cl.
*A61K 31/44* (2006.01)

(52) U.S. Cl. ........ 514/300; 544/350; 546/113; 548/255; 548/262.2

(58) Field of Classification Search .................. 514/300; 544/350; 546/113; 548/255, 262.2
See application file for complete search history.

(56) References Cited

U.S. PATENT DOCUMENTS

| | | |
|---|---|---|
| 6,469,006 B1 | 10/2002 | Blair et al. |
| 6,476,034 B2 | 11/2002 | Wang et al. |
| 6,573,262 B2 | 6/2003 | Wallace et al. |
| 6,825,201 B2 | 11/2004 | Wang et al. |
| 6,900,206 B2 | 5/2005 | Kadow et al. |
| 6,900,323 B2 | 5/2005 | Wang et al. |
| 7,348,337 B2 | 3/2008 | Wang et al. |
| 7,354,924 B2 | 4/2008 | Wang et al. |
| 7,396,830 B2 | 7/2008 | Wang et al. |
| 7,449,476 B2 | 11/2008 | Ruediger et al. |
| 7,504,399 B2 | 3/2009 | Wang et al. |
| 2004/0063744 A1 | 4/2004 | Wang et al. |
| 2004/0063746 A1 | 4/2004 | Regueiro-Ren et al. |
| 2005/0209246 A1 | 9/2005 | Ueda et al. |
| 2005/0215543 A1 | 9/2005 | Lin et al. |
| 2005/0215544 A1 | 9/2005 | Lin et al. |
| 2005/0215545 A1 | 9/2005 | Lin et al. |
| 2005/0261296 A1 | 11/2005 | Yeung et al. |
| 2007/0155702 A1 | 7/2007 | Chen et al. |

FOREIGN PATENT DOCUMENTS

| | | |
|---|---|---|
| WO | WO 00/76521 | 12/2000 |
| WO | WO 02/062423 | 8/2002 |
| WO | WO 02/085301 | 10/2002 |
| WO | WO 03/068221 | 8/2003 |
| WO | WO 03/103607 | 12/2003 |
| WO | WO 2004/043375 | 5/2004 |
| WO | WO 2005/016344 | 2/2005 |
| WO | WO 2005/121094 | 12/2005 |
| WO | WO 2007/103456 | 9/2007 |
| WO | WO2007/127635 | 11/2007 |

OTHER PUBLICATIONS

Blair, W.S. et al., "HIV-1 entry—an expanding portal for drug discovery", Drug Discovery Today, vol. 5, No. 5, pp. 183-194 (2000).
Dhar, T.G.M. et al., "Synthesis and SAR of p38α MAP kinase inhibitors based on heterobicyclic scaffolds", Bioorganic & Medicinal Chemistry Letters, vol. 17, pp. 5019-5024 (2007).
Hotoda, H., "Small-molecule inhibitors of HIV-1 entry via chemokine receptors", Drugs of the Future, vol. 24, No. 12, pp. 1355-1362 (1999).
Lu, R.-J. et al., "Design and Synthesis of Human Immunodeficiency Virus Entry Inhibitors: Sulfonamide as an Isotere for the α-Ketoamide Group", Journal of Medicinal Chemistry, vol. 50, No. 26, pp. 6535-6544 (2007).
Meanwell, N.A. et al., "Inhibitors of the entry of HIV into host cells", Current Opinion in Drug Discovery & Development, vol. 6, No. 4, pp. 451-461 (2003).
Sodroski, J.G., "HIV-1 Entry Inhibitors in the Side Pocket", Cell, vol. 99, pp. 243-246 (1999).
Wang, J. et al., "Modification and structure-activity relationship of a small molecule HIV-1 inhibitor targeting the viral envelope glycoprotein gp120", Org, Biomol. Chem., vol. 3, pp. 1781-1786 (2005).

*Primary Examiner* — James O Wilson
*Assistant Examiner* — Douglas M Willis
(74) *Attorney, Agent, or Firm* — John F. Levis

(57) ABSTRACT

Compounds having drug and bio-affecting properties, their pharmaceutical compositions and methods of use are set forth. In particular, diketo fused azolopiperidine and azolopiperazine derivatives of Formula I:

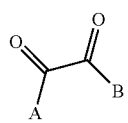

that possess unique antiviral activity are provided. These compounds are useful for the treatment of HIV and AIDS.

4 Claims, No Drawings

DIKETO SUBSTITUTED PYRROLO[2,3-C] PYRIDINES

CROSS-REFERENCE TO RELATED APPLICATION

This non-provisional application claims the benefit of U.S. Provisional Application Ser. No. 61/075,374 filed Jun. 25, 2008.

FIELD OF THE INVENTION

This invention provides compounds having drug and bio-affecting properties, their pharmaceutical compositions and methods of use. In particular, the disclosure is directed to diketo fused azolopiperidine and azolopiperazine derivatives that possess unique antiviral activity. More particularly, the present disclosure relates to compounds useful for the treatment of HIV and AIDS.

BACKGROUND OF THE INVENTION

HIV-1 (human immunodeficiency virus-1) infection remains a major medical problem, with an estimated 45 million people infected worldwide at the end of 2007. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), tenofovir disoproxil fumarate salt (or VIREAD®), emtricitabine (or FTC-EMTRIVA®), COMBIVIR® (contains—3TC plus AZT), TRIZIVIR® (contains abacavir, lamivudine, and zidovudine), Epzicom (contains abacavir and lamivudine), TRUVADA® (contains VIREAD® and EMTRIVA®); non-nucleoside reverse transcriptase inhibitors: nevirapine (or VIRAMUNE®), delavirdine (or RESCRIPTOR®) and efavirenz (or SUSTIVA®), Atripla (TRUVADA®+SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®), and integrase inhibitors such as raltegravir (Isentress), and entry inhibitors such as enfuvirtide (T-20) (FUZEON®) and maraviroc (Selzentry).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g., most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when suboptimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a novel subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. A disclosure describing indoles of which the structure shown below for BMS-705 is representative, has been disclosed (Antiviral Indoleoxoacetyl Piperazine Derivatives).

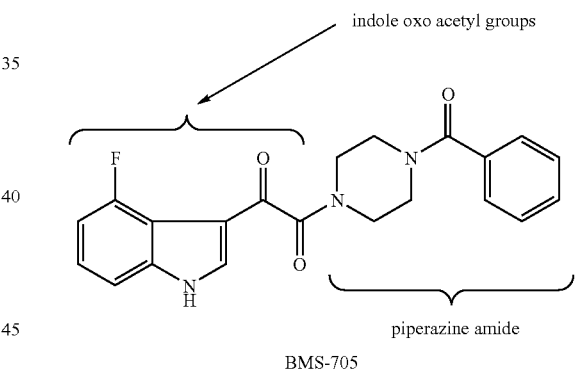

BMS-705

Two other compounds, referred to in the literature as BMS-806 and BMS-043 have been described in both the academic and patent art:

BMS-806

BMS-043

Some description of their properties in human clinical trials has been disclosed in the literature.

It should be noted that in all three of these structures, a piperazine amide (in these three structures a piperazine phenyl amide) is present and this group is directly attached to an oxoacetyl moiety. The oxoacetyl group is attached at the 3-position of 4-fluoro indole in BMS-705 and to the 3 position of substituted azaindoles in BMS-806 and BMS-043.

In an effort to obtain improved anti-HIV compounds, later publications described in part, modified substitution patterns on the indoles and azaindoles. Examples of such efforts include: (1) novel substituted indoleoxoacetic piperazine derivatives, (2) substituted piperazinyloxoacetylindole derivatives, and (3) substituted azaindoleoxoacetic piperazine derivatives.

Replacement of these groups with other heteroaromatics or substituted heteroaromatics or bicyclic hydrocarbons was also shown to be feasible. Examples include: (1) indole, azaindole and related heterocyclic amidopiperazine derivatives; (2) bicyclo 4.4.0 antiviral derivatives; and (3) diazaindole derivatives.

A select few replacements for the piperazine amide portion of the molecules have also been described in the art and among these examples are (1) some piperidine alkenes; (2) some pyrrolidine amides; (3) some N-aryl or heteroaryl piperazines; (4) some piperazinyl ureas; and (5) some carboline containing compounds.

Method(s) for preparing prodrugs for this class of compounds are disclosed in Prodrugs of Piperazine and Substituted Piperidine Antiviral Agents (Ueda et al., U.S. non-provisional application Ser. No. 11/066,745, filed Feb. 25, 2005 or U.S. Publication No. 2005/0209246 or WO 2005/090367 A1).

A published PCT patent application WO 2003/103607 A1 (Jun. 11, 2003) disclosures an assay useful for assaying some HIV inhibitors.

Several published patent applications describe combination studies with piperazine benzamide inhibitors, for example, U.S. Publication No. 2005/0215543 (WO 2005/102328 A1), U.S. Publication No. 2005/0215544 (WO 2005/102391 A1), and U.S. Publication No. 2005/0215545 (WO 2005/102392 A2).

A publication on new compounds in this class of attachment inhibitors (Wang, J. et al., Org. Biol. Chem., 3:1781-1786 (2005)) and a patent application on some more remotely related compounds have appeared WO 2005/016344 published on Feb. 24, 2005.

Published patent applications WO 2005/016344 and WO 2005/121094 also describe piperazine derivatives which are HIV inhibitors. Other references in the HIV attachment area include U.S. Publication Nos. 2007/0155702, 2007/0078141 and 2007/0287712, WO 2007/103456, as well as U.S. Pat. Nos. 7,348,337 and 7,354,924. A literature reference is *J. Med. Chem.*, 50:6535 (2007).

What is therefore needed in the art are new HIV attachment inhibitor compounds, and compositions thereof, which are efficacious against HIV infection. The compounds described in the foregoing references are structurally distinct from the compounds of the present invention hereinafter described.

SUMMARY OF THE INVENTION

The present invention provides compounds of Formula I below, the pharmaceutically acceptable salts and/or solvates (e.g. hydrates) thereof, their pharmaceutical formulations, and their use in patients suffering from or susceptible to a virus such as HIV. The compounds of Formula I, their pharmaceutically acceptable salts and/or solvates are effective antiviral agents, particularly as inhibitors of HIV. They are useful for the treatment of HIV and AIDS.

One embodiment of the present invention is directed to a compound of Formula I, including pharmaceutically acceptable salts thereof:

wherein A is selected from the group consisting of:

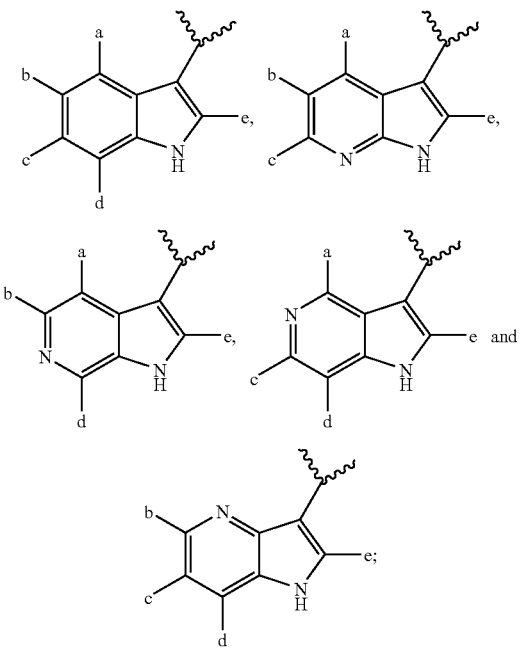

wherein B is selected from the group consisting of:

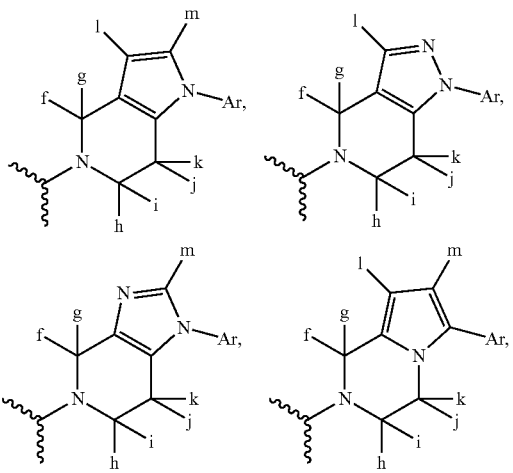

-continued

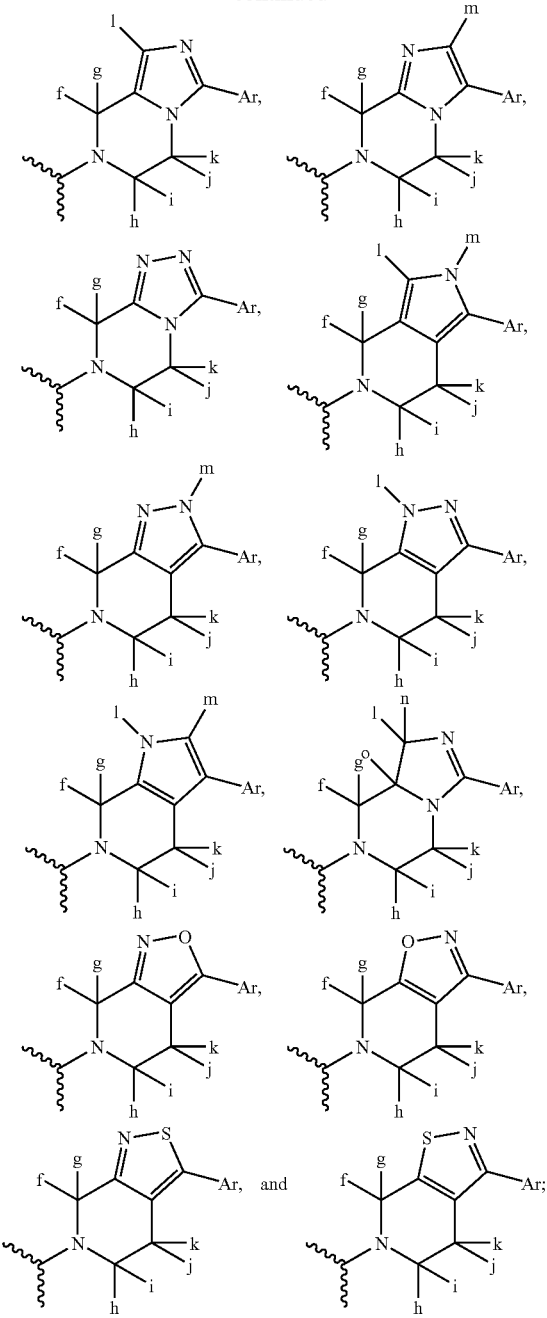

and further wherein a is selected from the group consisting of H, halogen and methoxy;

b and c are selected from the group consisting of H and halogen;

d is selected from the group consisting of H, halogen, methoxy and Group C;

e is H;

f and g are selected from the group consisting of H, $(C_1-C_4)$ alkyl, and $(C_3-C_6)$ cycloalkyl group, and wherein said alkyl or cycloalkyl group is optionally substituted with one to three substitutions selected from the group of F, OH, OR, $NR_1R_2$, COOR, and $CONR_1R_2$;

and wherein f and g can be connected by carbon, oxygen, nitrogen or sulfur atom to form a ring;

h and i are selected from the group consisting of H, $(C_1-C_4)$ alkyl, and $(C_3-C_6)$ cycloalkyl group, wherein said alkyl or cycloalkyl group is optionally substituted with one to three substitutions selected from the group of F, OH, OR, $NR_1R_2$, COOR, and $CONR_1R_2$;

and wherein h and i can be connected by a carbon, oxygen, nitrogen or sulfur atom to form a ring;

j and k are selected from the group consisting of H, F, $(C_1-C_4)$ alkyl, and $(C_3-C_6)$ cycloalkyl group, and wherein said alkyl or cycloalkyl group is optionally substituted with one to three substitutions selected from the group of F, OH, OR, $NR_1R_2$, COOR, and $CONR_1R_2$;

and wherein j and k can be connected by carbon, oxygen, nitrogen or sulfur atom to form a ring;

and further wherein j+k is C=O;

l and m are selected from the group consisting of H, OH, $(C_1-C_4)$ alkyl optionally substituted with one to three substitutions selected from F, OH, OR, $NR_1R_2$, COOR, $CONR_1R_2$, $(C_3-C_6)$ cycloalkyl optionally substituted with one to three substitutions selected from F, OH, OR, $NR_1R_2$, COOR, $CONR_1R_2$, OR, halogen (attached to carbon only), OR, $NR_1R_2$, COOR, $CONR_1R_2$, and Group D;

n and o are selected from the group consisting of H, $(C_1-C_4)$ alkyl optionally substituted with one to three substitutions selected from F, OH, OR, $NR_1R_2$, COOR, $CONR_1R_2$, $(C_3-C_6)$ cycloalkyl optionally substituted with one to three substitutions (selected from F, OH, OR, $NR_1R_2$, COOR, $CONR_1R_2$), COOR, $CONR_1R_2$ and Group D;

Ar is selected from the group consisting of phenyl and heteroaryl; wherein said phenyl and heteroaryl are independently optionally substituted with one to three same or different halogens or from one to three same or different substituents selected from Group E; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

Group C is selected from the group consisting of COOR, $CONR_1R_2$, and Group D;

Group D is selected from the group consisting of phenyl and heteroaryl; wherein said phenyl and heteroaryl are independently optionally substituted with one to three same or different halogens or from one to three same or different substituents selected from Group E; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

Group E is selected from the group consisting of OH, OR, $NR_1R_2$, CN, COOR, $CONR_1R_2$, $(C_1-C_4)$ alkyl, $(C_3-C_6)$ cycloalkyl, and wherein said alkyl or cycloalkyl group is optionally substituted with one to three substitutions selected from the group of F, OH, OR, $NR_1R_2$, COOR, and $CONR_1R_2$;

R, $R_1$ and $R_2$ are independently H, $(C_1-C_4)$ alkyl, $(C_3-C_6)$ cycloalkyl group; and wherein $R_1$ and $R_2$ can be connected by carbon, oxygen, nitrogen or sulfur atom to form a ring.

Another embodiment of the present invention is directed to a method for treating mammals infected with a virus, especially wherein said virus is HIV, comprising administering to said mammal an antiviral effective amount of a compound of Formula I above, and one or more pharmaceutically acceptable carriers, excipients or diluents. Optionally, the compound of Formula I can be administered in combination with an antiviral effective amount of an AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising an antiviral effective amount of a compound of Formula I and one or more pharmaceutically acceptable carriers, excipients, diluents and optionally in combination with an antiviral effective amount of an AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formula I.

The present invention is directed to these, as well as other important ends, hereinafter described.

DETAILED DESCRIPTION OF THE EMBODIMENTS

Since the compounds of the present disclosure may possess asymmetric centers and therefore occur as mixtures of diastereomers and enantiomers, the present disclosure includes the individual diastereoisomeric and enantiomeric forms of the compounds of Formula I in addition to the mixtures thereof.

Definitions

Unless otherwise specifically set forth elsewhere in the application, one or more of the following terms may be used herein, and shall have the following meanings:

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$ fluoroalkyl" refers to F-substituted $C_1$-$C_4$ alkyl wherein at least one H atom is substituted with F atom, and each H atom can be independently substituted by F atom;

"Halogen" refers to chlorine, bromine, iodine or fluorine.

An "aryl" or "Ar" group refers to an all carbon monocyclic or fused-ring polycyclic(i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$ with R$^x$ and R$^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a Z$_3$CC(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O)$_2$ — groups with Z as defined above.

A "trihalomethanesulfonamido" group refers to a Z$_3$CS(=O)$_2$NR$^x$— group with Z as defined above and R$^x$ being H or (C$_{1-6}$)alkyl.

A "sulfinyl" group refers to a —S(=O)—R" group, with R" being (C$_{1-6}$)alkyl.

A "sulfonyl" group refers to a —S(=O)$_2$R" group with R" being (C$_{1-6}$)alkyl.

A "S-sulfonamido" group refers to a —S(=O)$_2$NR$^X$R$^Y$, with R$^X$ and R$^Y$ independently being H or (C$_{1-6}$)alkyl.

A "N-Sulfonamido" group refers to a R"S(=O)$_2$NR$_X$— group, with R$_x$ being H or (C$_{1-6}$)alkyl.

A "O-carbamyl" group refers to a —OC(=O)NR$^x$R$^y$ group, with R$^X$ and R$^Y$ independently being H or (C$_{1-6}$)alkyl.

A "N-carbamyl" group refers to a R$^x$OC(=O)NR$^y$ group, with r$^x$ and R$^y$ independently being H or (C$_{1-6}$)alkyl.

A "O-thiocarbamyl" group refers to a —OC(=S)NR$^x$R$^y$ group, with R$^x$ and R$^y$ independently being H or (C$_{1-6}$)alkyl.

A "N-thiocarbamyl" group refers to a R$^x$OC('S)NR$^y$— group, with R$^x$ and R$^y$ independently being H or (C$_{1-6}$)alkyl.

An "amino" group refers to an —NH$_2$ group.

A "C-amido" group refers to a —C('O)NR$^x$R$^y$ group, with R$^x$ and R$^y$ independently being H or (C$_{1-6}$)alkyl.

A "C-thioamido" group refers to a —C(=S)NR$^x$R$^y$ group, with R$^x$ and R$^y$ independently being H or (C$_{1-6}$)alkyl.

A "N-amido" group refers to a R$^x$C(=O)NR$^y$— group, with R$^x$ and R$^y$ independently being H or (C$_{1-6}$)alkyl.

An "ureido" group refers to a —NR$^x$C(=O)NR$^y$R$^{y2}$ group, with R$^x$, R$^y$, and R$^{y2}$ independently being H or (C$_{1-6}$)alkyl.

A "guanidino" group refers to a —R$^x$NC(=N)NR$^y$R$^{y2}$ group, with R$^x$, R$^y$, and R$^{y2}$ independently being H or (C$_{1-6}$)alkyl.

A "guanyl" group refers to a R$^x$R$^y$NC(=N)— group, with R$^x$ and R$^y$ independently being H or (C$_{1-6}$)alkyl.

A "cyano" group refers to a —CN group.

A "silyl" group refers to a —Si(R")$_3$, with R" being (C$_{1-6}$)alkyl or phenyl.

A "phosphonyl" group refers to a P(=O)(OR$^x$)$_2$ with R$^x$ being (C$_{1-6}$)alkyl.

A "hydrazino" group refers to a —NR$^x$NR$^y$R$^{y2}$ group, with R$^x$, R$^y$, and R$^{y2}$ independently being H or (C$_{1-6}$)alkyl.

A "4, 5, or 6 membered ring cyclic N-lactam" group refers to

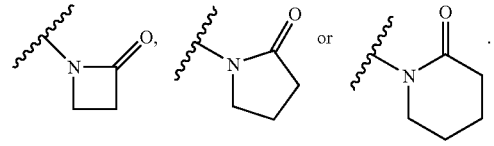

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of this disclosure. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g., hydroxyl-substituted alkylamines such as diethanolamine, triethanolamine or tris (hydroxymethyl)-aminomethane), or with bases such as piperidine or morpholine.

As stated above, the compounds of the invention also include "prodrugs", The term "prodrug" as used herein encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates, half acid esters such as malonates, succinates or glutarates, and the like. In certain embodiments, amino acid esters may be especially preferred.

Examples of such prodrug esters include

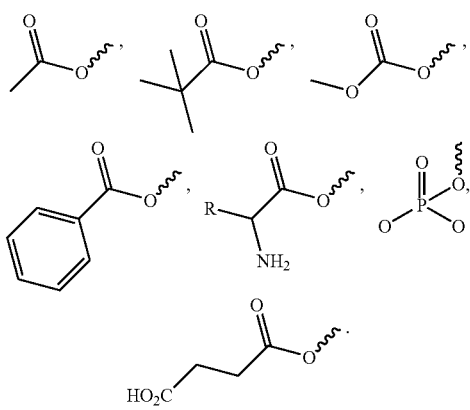

The term "prodrug ethers" include both phosphate acetals and O-glucosides. Representative examples of such prodrug ethers include

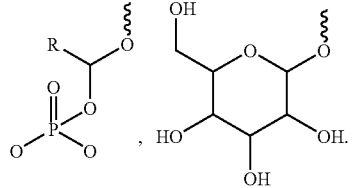

As set forth above, the invention is directed to compounds of Formula I, including pharmaceutically acceptable salts thereof:

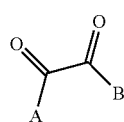

I wherein A is selected from the group consisting of:

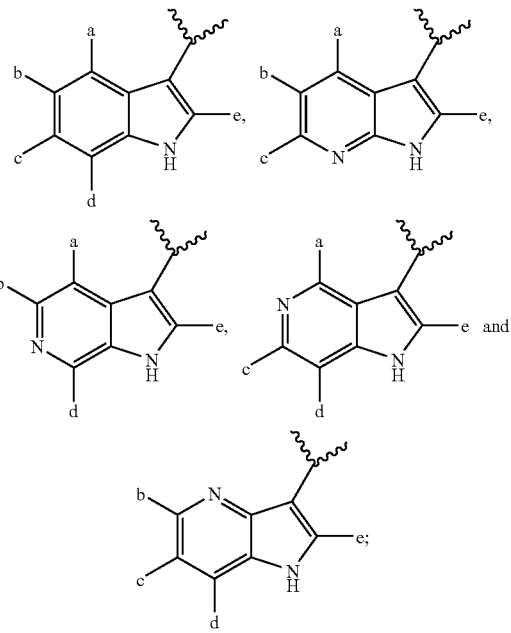

wherein B is selected from the group consisting of:

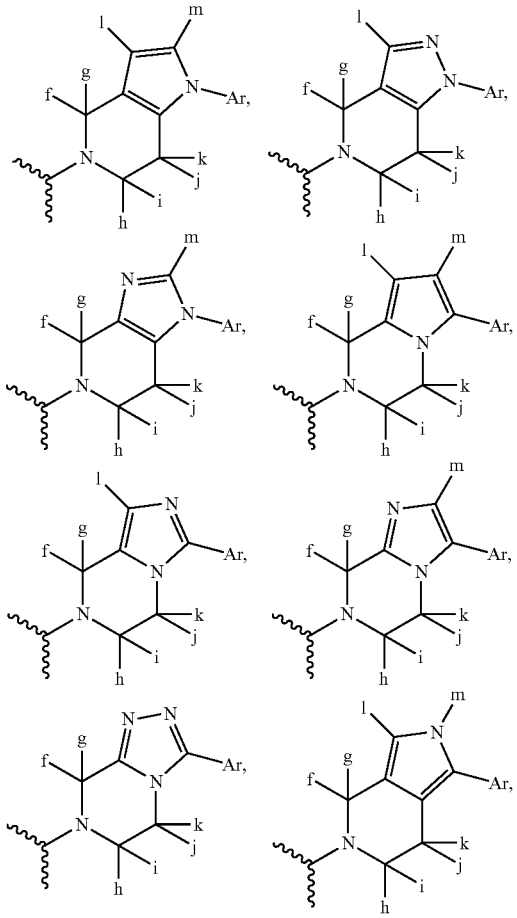

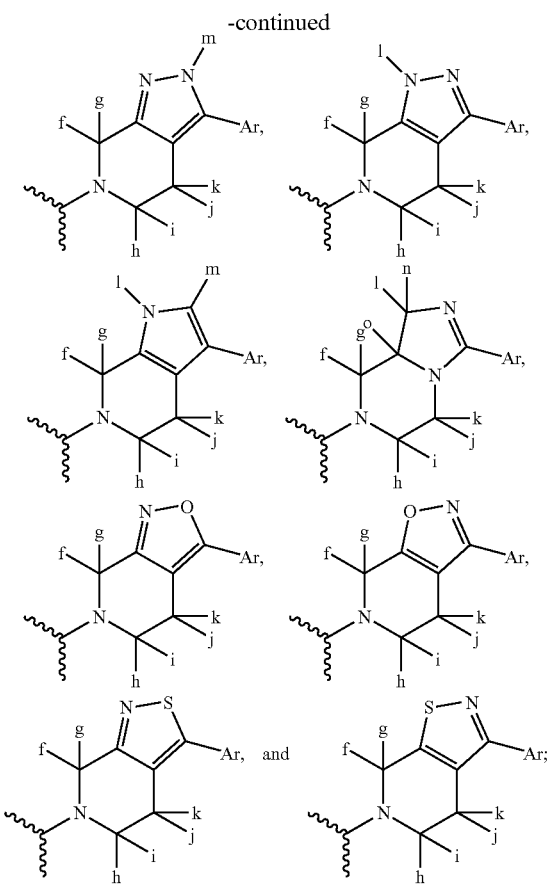

and further wherein a is selected from the group consisting of H, halogen and methoxy;

b and c are selected from the group consisting of H and halogen;

d is selected from the group consisting of H, halogen, methoxy and Group C;

e is H;

f and g are selected from the group consisting of H, $(C_1-C_4)$ alkyl, and $(C_3-C_6)$ cycloalkyl group, and wherein said alkyl or cycloalkyl group is optionally substituted with one to three substitutions selected from the group of F, OH, OR, $NR_1R_2$, COOR, and $CONR_1R_2$;

and wherein f and g can be connected by carbon, oxygen, nitrogen or sulfur atom to form a ring;

h and i are selected from the group consisting of H, $(C_1-C_4)$ alkyl, and $(C_3-C_6)$ cycloalkyl group. wherein said alkyl or cycloalkyl group is optionally substituted with one to three substitutions selected from the group of F, OH, OR, $NR_1R_2$, COOR, and $CONR_1R_2$;

and wherein h and i can be connected by a carbon, oxygen, nitrogen or sulfur atom to form a ring;

j and k are selected from the group consisting of H, F, $(C_1-C_4)$ alkyl, and $(C_3-C_6)$ cycloalkyl group, and wherein said alkyl or cycloalkyl group is optionally substituted with one to three substitutions selected from the group of F, OH, OR, $NR_1R_2$, COOR, and $CONR_1R_2$;

and wherein j and k can be connected by carbon, oxygen, nitrogen or sulfur atom to form a ring;

and further wherein j+k is C=O;

l and m are selected from the group consisting of H, OH, $(C_1-C_4)$ alkyl optionally substituted with one to three substitutions selected from F, OH, OR, $NR_1R_2$, COOR, $CONR_1R_2$, $(C_3-C_6)$ cycloalkyl optionally substituted with one to three substitutions selected from F, OH, OR, $NR_1R_2$, COOR, CON $R_1R_2$, OR, halogen (attached to carbon only), OR, $NR_1R_2$, COOR, $CONR_1R_2$, and Group D;

n and o are selected from the group consisting of H, $(C_1-C_4)$ alkyl optionally substituted with one to three substitutions selected from F, OH, OR, $NR_1R_2$, COOR, CON $R_1R_2$, $(C_3-C_6)$ cycloalkyl optionally substituted with one to three substitutions (selected from F, OH, OR, $NR_1R_2$, COOR, $CONR_1R_2$), COOR, $CONR_1R_2$ and Group D;

Ar is selected from the group consisting of phenyl and heteroaryl; wherein said phenyl and heteroaryl are independently optionally substituted with one to three same or different halogens or from one to three same or different substituents selected from Group E; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

Group C is selected from the group consisting of COOR, $CONR_1R_2$, and Group D;

Group D is selected from the group consisting of phenyl and heteroaryl; wherein said phenyl and heteroaryl are independently optionally substituted with one to three same or different halogens or from one to three same or different substituents selected from Group E; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

Group E is selected from the group consisting of OH, OR, $NR_1R_2$, CN, COOR, $CONR_1R_2$, $(C_1-C_4)$ alkyl, $(C_3-C_6)$ cycloalkyl, and wherein said alkyl or cycloalkyl group is optionally substituted with one to three substitutions selected from the group of F, OH, OR, $NR_{R2}$, COOR, and $CONR_1R_2$;

R, $R_1$ and $R_2$ are independently H, $(C_1-C_4)$ alkyl, $(C_3-C_6)$ cycloalkyl group; and wherein $R_1$ and $R_2$ can be connected by carbon, oxygen, nitrogen or sulfur atom to form a ring.

More preferred compounds of the Formula I include those wherein A=

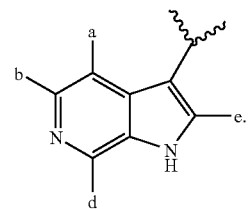

Also preferred compounds of the Formula I include those wherein B=

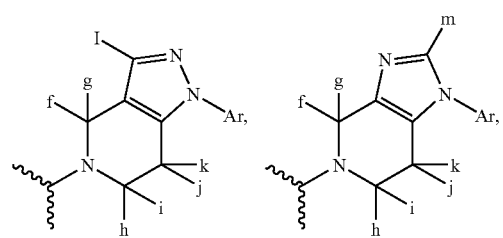

-continued
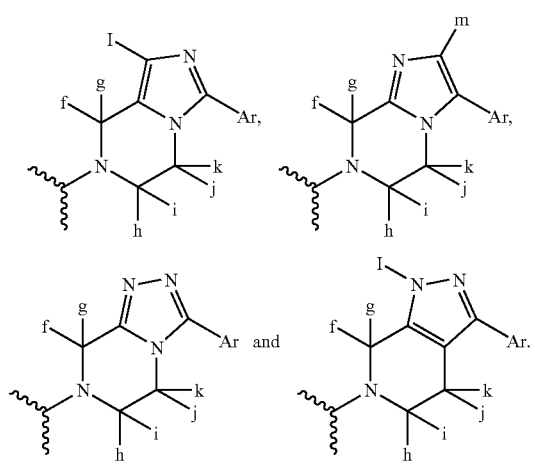
In another embodiment, both the preferred forms of A and B in the compound of Formula I are as set forth above.
Particularly preferred compounds of the invention as part of Formula I include the following:
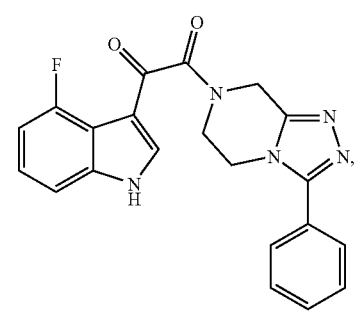
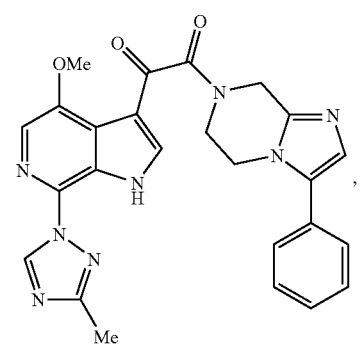
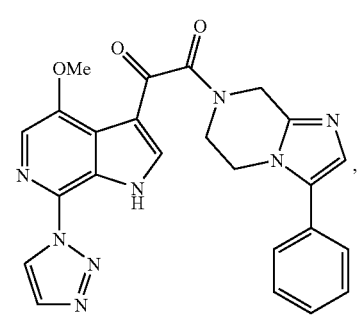
-continued
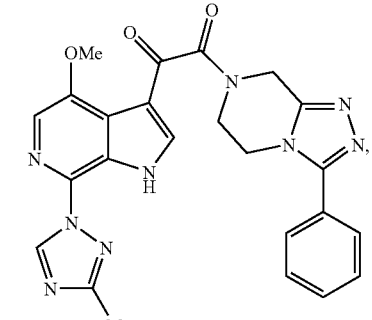
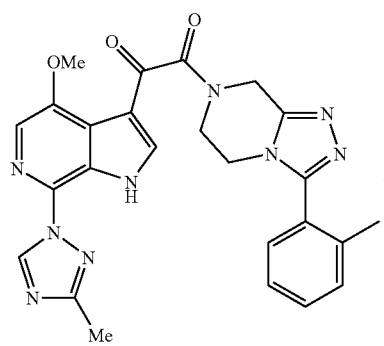
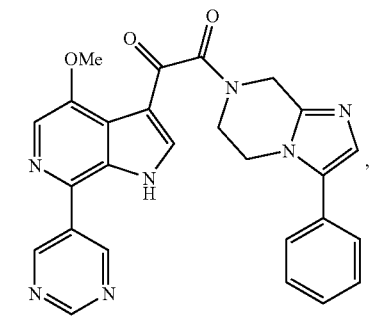
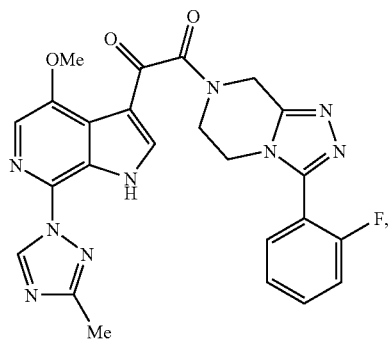
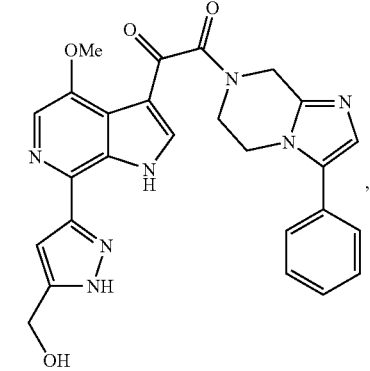

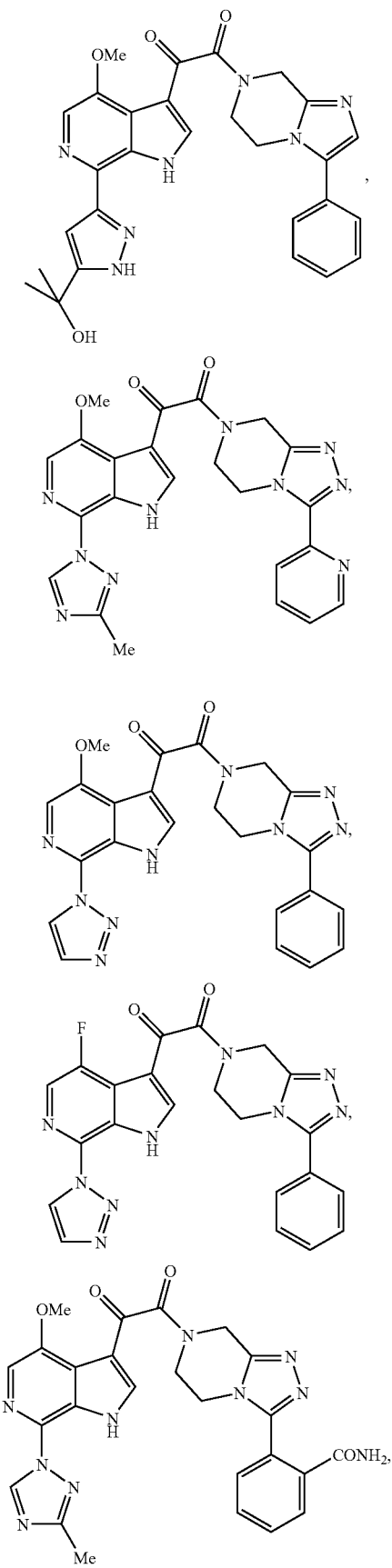
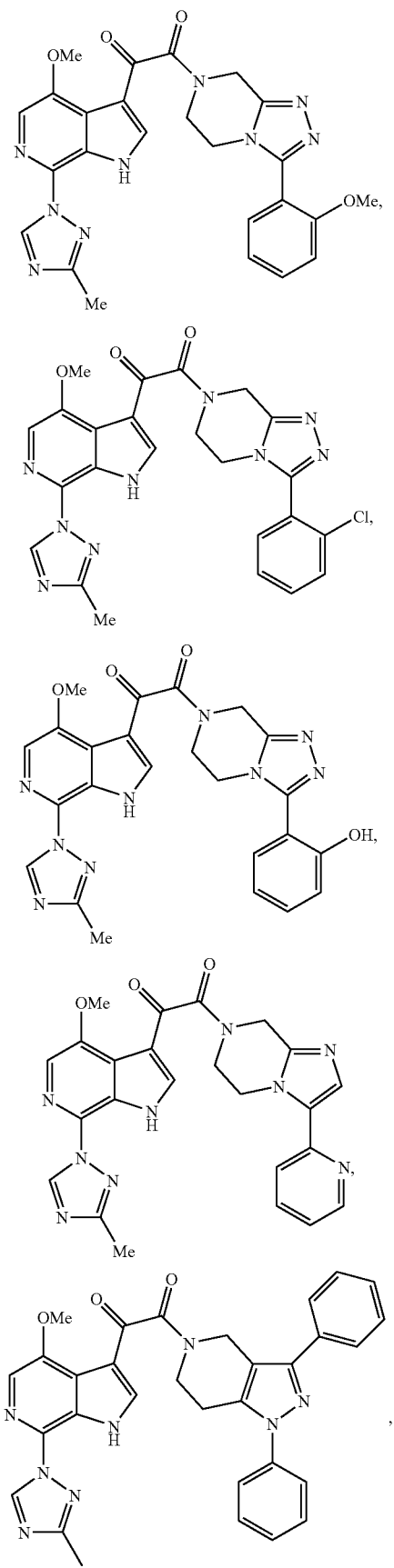

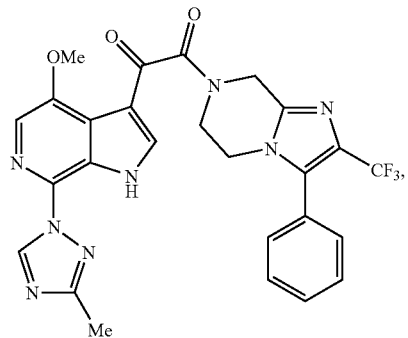
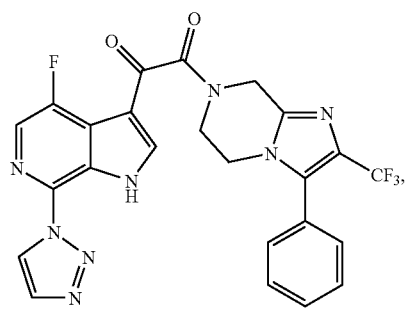
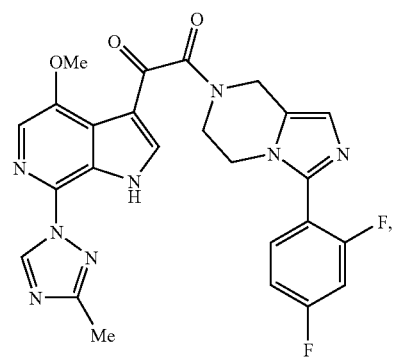
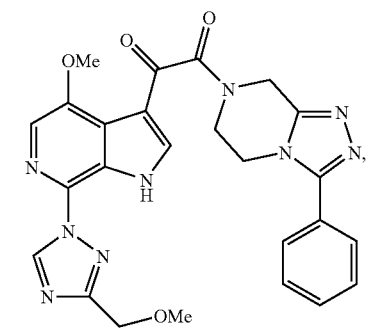
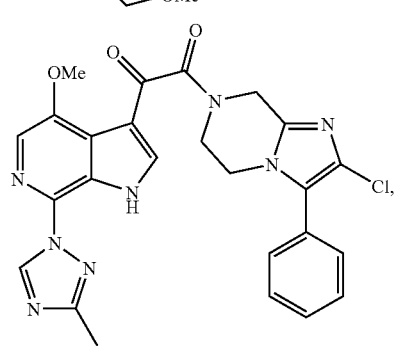
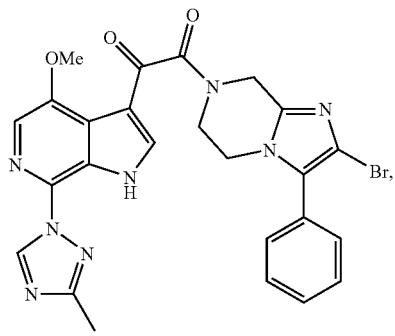
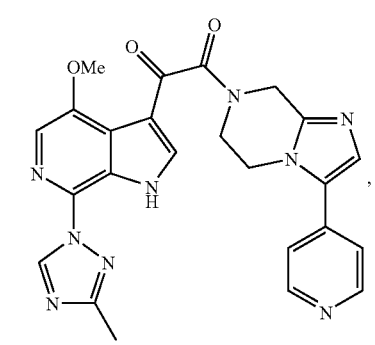
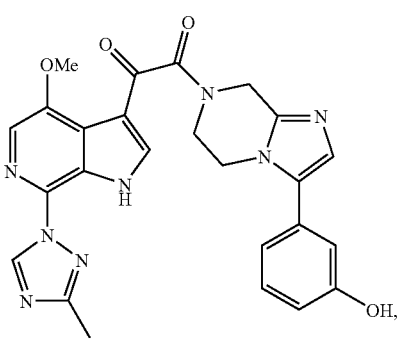
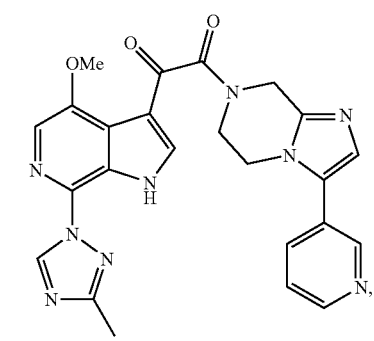
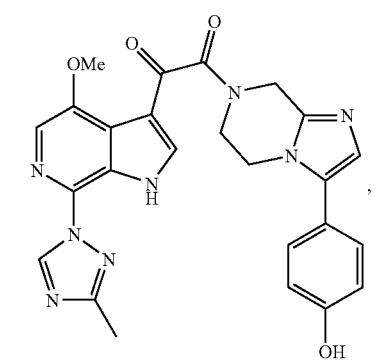

21
-continued
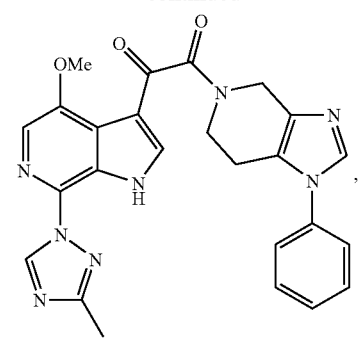,
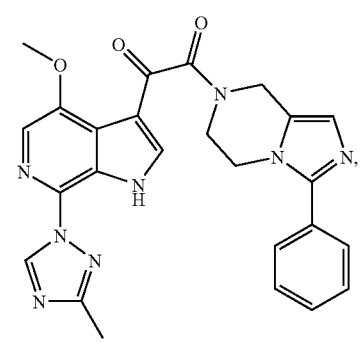,
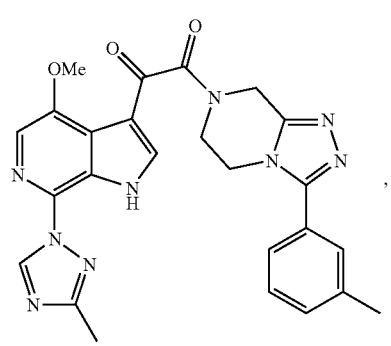,
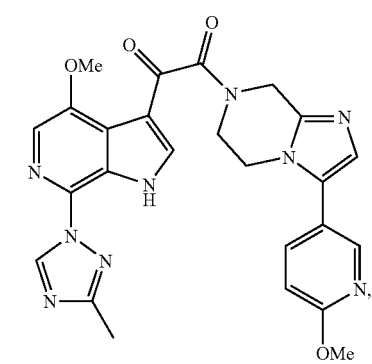,
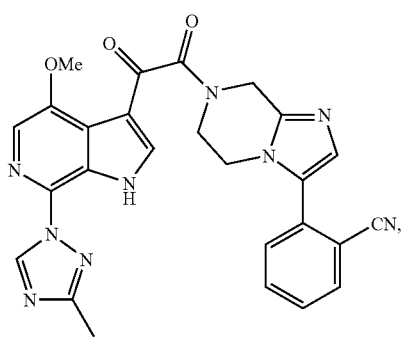,
22
-continued
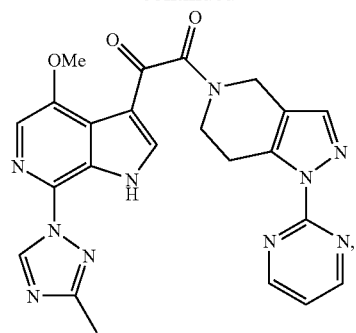,
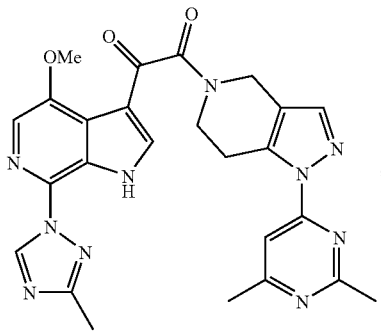,
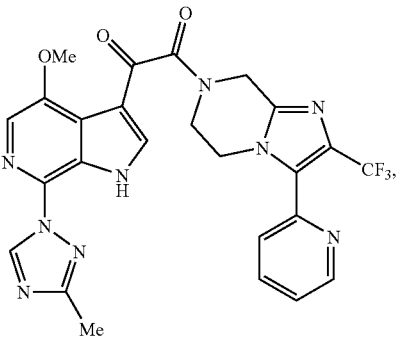,
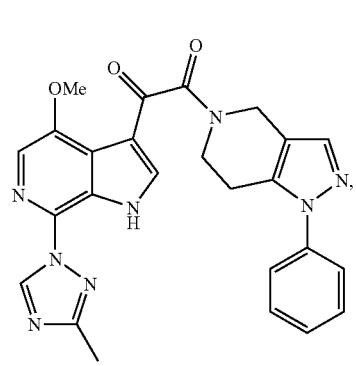,
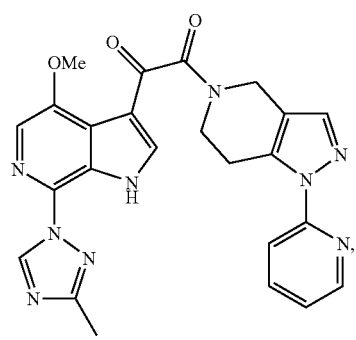, -continued

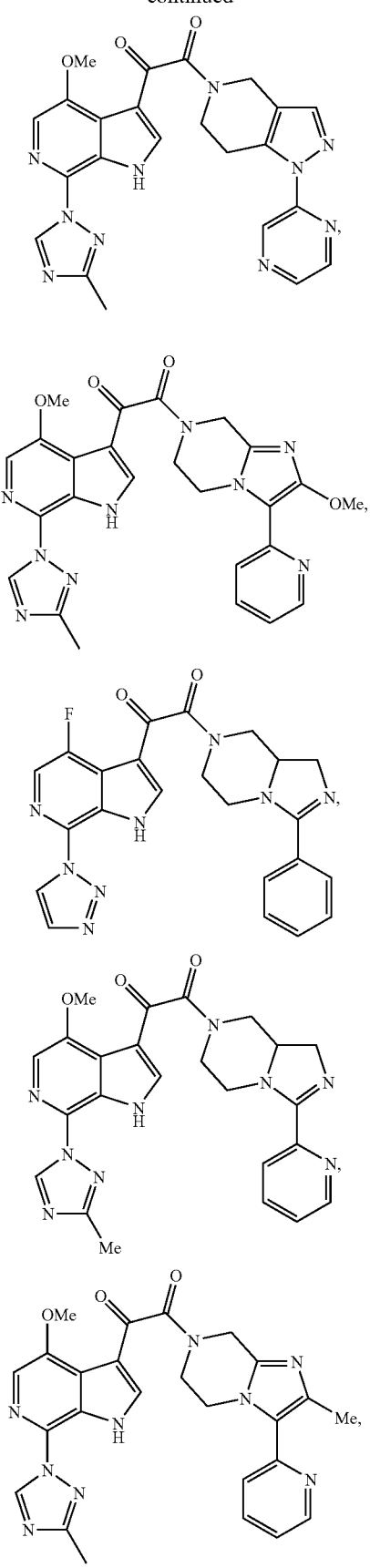

-continued

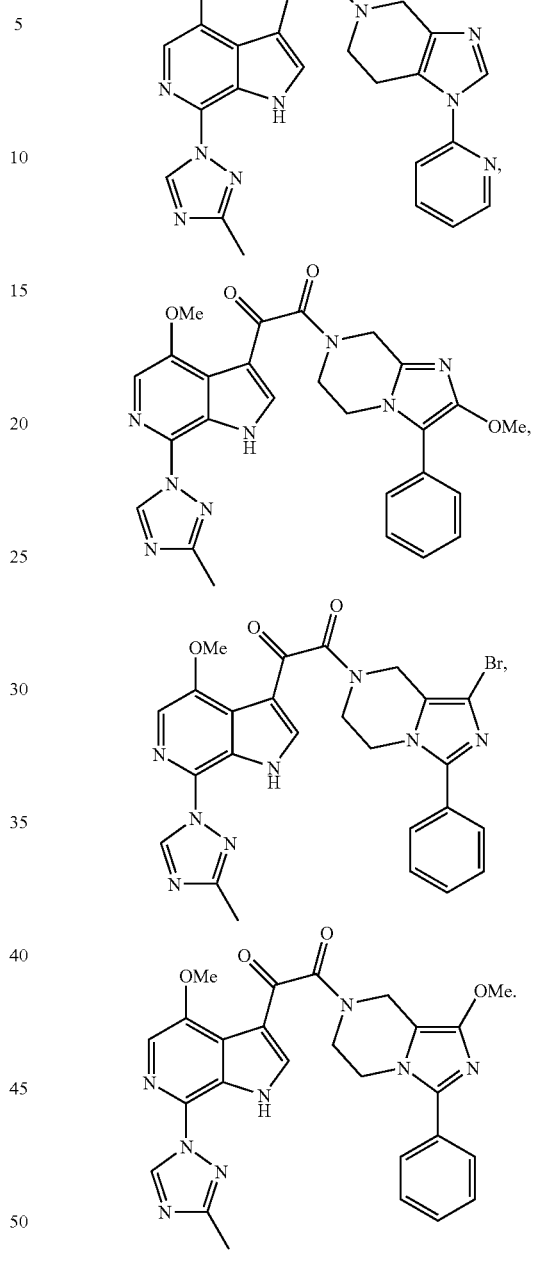

The compounds of the present invention, according to all the various embodiments described above, may be administered orally, parenterally (including subcutaneous injections, intravenous, intramuscular, intrastemal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present disclosure, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formula I, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this disclosure can be administered orally to humans in a dosage range of 1 to 100 mg/kg body weight in divided doses, usually over an extended period, such as days, weeks, months, or even years. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formula I herein set forth, together with one or more agents useful in the treatment of AIDS. For example, the compounds of this disclosure may be effectively administered, whether at periods of pre-exposure and/or post-exposure, in combination with effective amounts of the AIDS antivirals, immunomodulators, anti-infectives, or vaccines, such as those in the following non-limiting table:

| Drug Name | Manufacturer | Indication |
|---|---|---|
| | ANTIVIRALS | |
| 097 | Hoechst/Bayer | HIV infection, AIDS, ARC (non-nucleoside reverse transcriptase (RT) inhibitor) |
| Amprenavir 141 W94 GW 141 | GlaxoWellcome | HIV infection, AIDS, ARC (protease inhibitor) |
| Abacavir (1592U89) GW 1592 | GlaxoWellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection, ARC, PGL, HIV positive, AIDS |
| Alpha Interferon | GlaxoWellcome | Kaposi's sarcoma, HIV in combination with RETROVIR ® |
| Ansamycin LM 427 | Adria Laboratories (Dublin, OH) Erbamont (Stamford, CT) | ARC |
| Antibody which neutralizes pH labile alpha aberrant interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |

-continued

| Drug Name | Manufacturer | Indication |
|---|---|---|
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | Sight threatening CMV peripheral CMV retinitis |
| Darunavir (Prezista) | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, Stocrin | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | SmithKline | Herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | GlaxoWellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |

-continued

| Drug Name | Manufacturer | Indication |
| --- | --- | --- |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | GlaxoWellcome | Genital HSV and CMV infections |
| VIRAZOLE ® (Ribavirin) | Viratek/ICN (Costa Mesa, CA) | Asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | GlaxoWellcome | HIV infection, AIDS, ARC, Kaposi's sarcoma, in combination with other therapies |
| Tenofovir disoproxil, fumarate salt (VIREAD) ® | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection, AIDS, protease inhibitor |
| FUZEON ® (enfuvirtide or T-20) | Roche/Trimeris | HIV infection AIDS, viral fusion inhibitor |
| LEXIVA ® (or fosamprenavir calcium) | GSK/Vertex | HIV infection, AIDS, viral protease inhibitor |
| Selzentry (maraviroc) (UK 427857) | Pfizer | HIV infection, AIDS, (CCR5 antagonist, in development) |
| TRIZIVIR ® | GSK | HIV infection, AIDS, (three drug combination) |
| Bevirimat | Panacos | HIV infection, AIDS, (maturation inhibitor, in development) |
| Sch-417690 (vicriviroc) | Schering-Plough | HIV infection, AIDS, (CCR5 antagonist, in development) |
| TAK-652 | Takeda | HIV infection, AIDS, (CCR5 antagonist, in development) |
| GSK 873140 (ONO-4128) | GSK/ONO | HIV infection, AIDS, (CCR5 antagonist, in development) |
| Integrase Inhibitor MK-0518 Raltegravir | Merck | HIV infection, AIDS |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV infection, AIDS, viral integrase inhibitor in development |
| Triple drug combination Atripla | Gilead/ Bristol-Myers Squibb | Combination of Tenofovir disoproxil fumarate salt (VIREAD ®), EMTRIVA ® (Emtricitabine), and SUSTIVA ® (Efavirenz) |

-continued

| Drug Name | Manufacturer | Indication |
|---|---|---|
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination with TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination with AZT |
| HIV Core Particle Immunostimulant | Rorer | Seropositive HIV |
| IL-2 Interleukin-2 | Cetus | AIDS, in combination with AZT |
| IL-2 Interleukin-2 | Hoffman-LaRoche Immunex | AIDS, ARC, HIV, in combination with AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination with AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering-Plough | Kaposi's sarcoma with AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination with AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination with AZT |
| SK&F106528 Soluble T4 | SmithKline | HIV infection |
| Thymopentin | Immunobiology Research Institute (Annandale, NJ) | HIV infection |
| Tumor Necrosis Factor; TNF | Genentech | ARC, in combination with gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |

| Drug Name | Manufacturer | Indication |
|---|---|---|
| Intraconazole-R51211 | Janssen Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia associated with AZT therapy |
| Recombinant Human Growth Hormone | Serono | AIDS-related wasting, cachexia |
| Megestrol Acetate | Bristol-Myers Squibb | Treatment of anorexia associated with AIDS |
| Testosterone | ALZA ®, SmithKline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with other HIV entry inhibitors. Examples of such HIV entry inhibitors are discussed in *Drugs of the Future,* 24(12):1355-1362 (1999); *Cell,* 9:243-246 (Oct. 29, 1999); and *Drug Discovery Today,* 5(5): 183-194 (May 2000) and Meanwell, N. A. et al., "Inhibitors of the entry of HIV into host cells", *Curr. Op. Drug Disc. Dev,* 6(4):451-461 (2003). Specifically the compounds can be utilized in combination with other attachment inhibitors, fusion inhibitors, and chemokine receptor antagonists aimed at either the CCR5 or CXCR4 coreceptor.

It will be understood that the scope of combinations of the compounds of this disclosure with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2 (R)-hydroxy-1-(S)-indanyl)-2(R)-phenylmethyl-4-(S)-hydroxy-5-(1-(4-(3-pyridyl-methyl)-2(S)-N'-(t-butylcarboxamido)-piperazinyl)-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine. (The preparation of ddC, ddI and AZT are also described in EP 0 484 071.)

In such combinations the compound of the present disclosure and other active agents may be administered separately or in conjunction. In addition, the administration of one element may be prior to, concurrent to, or subsequent to the administration of other agent(s).

GENERAL CHEMISTRY (METHODS of SYNTHESIS)

The present invention comprises compounds of Formula I, their pharmaceutical formulations, and their use in patients suffering from or susceptible to HIV infection. The compounds of Formula I include pharmaceutically acceptable salts thereof. General procedures to construct compounds of Formula I and intermediates useful for their synthesis are described in the following Schemes (after the Abbreviations).

Abbreviations

One or more of the following abbreviations, most of which are conventional abbreviations well known to those skilled in the art, may be used throughout the description of the disclosure and the examples:

h=hour(s)
rt=room temperature
mol=mole(s)
mmol=millimole(s)
g=gram(s)
mg=milligram(s)
mL=milliliter(s)
TFA=trifluoroacetic Acid
DCE=1,2-Dichloroethane
$CH_2Cl_2$=dichloromethane
TPAP=tetrapropylammonium perruthenate
THF=tetrahydrofuran
DEPBT=3-(diethoxyphosphoryloxy)-1,2,3-benzotriazin-4(3H)-one
DMAP=4-dimethylaminopyridine
P-EDC=polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=NN-diisopropylethylamine
MCPBA=meta-chloroperbenzoic acid
azaindole=1H-pyrrolo-pyridine
4-azaindole=1H-pyrrolo[3,2-b]pyridine
5-azaindole=1H-pyrrolo[3,2-c]pyridine
6-azaindole=1H-pyrrolo[2,3-c]pyridine
7-azaindole=1H-pyrrolo[2,3-b]pyridine
PMB=4-methoxybenzyl
DDQ=2,3-dichloro-5,6-dicyano-1,4-benzoquinone
OTf=trifluoromethanesulfonoxy NMM=4-methylmorpholine
PIP-COPh=1-benzoylpiperazine
NaHMDS=sodium hexamethyldisilazide
EDAC=1-(3-dimethylaminopropyl)-3-ethylcarbodiimide
TMS=trimethylsilyl
DCM=dichloromethane
DCE=dichloroethane
MeOH=methanol
THF=tetrahydrofuran
EtOAc=ethyl acetate
LDA=lithium diisopropylamide
TMP-Li=2,2,6,6-tetramethylpiperidinyl lithium
DME=dimethoxyethane
DIBALH=diisobutylaluminum hydride
HOBT=1-hydroxybenzotriazole
CBZ=benzyloxycarbonyl
PCC=pyridinium chlorochromate
TBTU=O-(benzotriazol-1-yl)-N,N,N',N'-tetramethyluronium tetrafluoroborate
DEBPT=3-(diethoxyphosphoryloxy)-1,2,3-benzotriazin-4(3H)-one
BOP=benzotriazole-1-yl-oxy-tris-(dimethylamino)-phosphoniumhexafluorophosphate Preparation of Compounds of Formula I, Chemistry Schemes A general reaction scheme is set forth as follows:

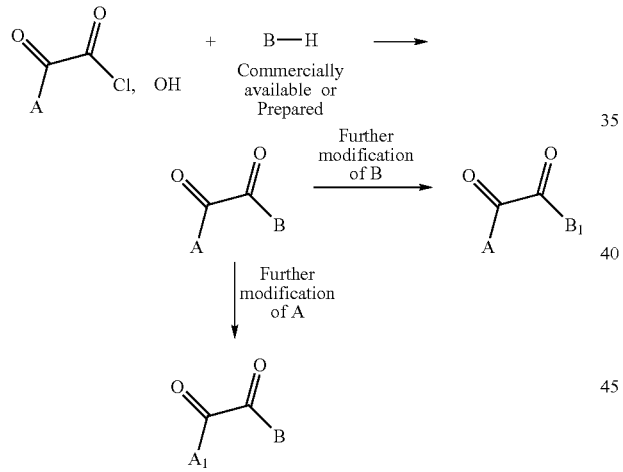

For the preparation of substituent "A" above, the procedures set forth in U.S. Pat. Nos. 6,476,034, 6,573,262, 6,469,006 and 7,354,924, as well as WO 2004/004337 are useful, and are incorporated herein by reference in their entirety.

Other specialized procedures are as follows:
When B=

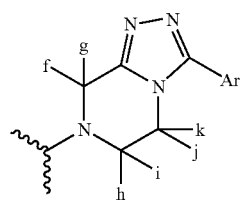

for the preparation of the following compound:

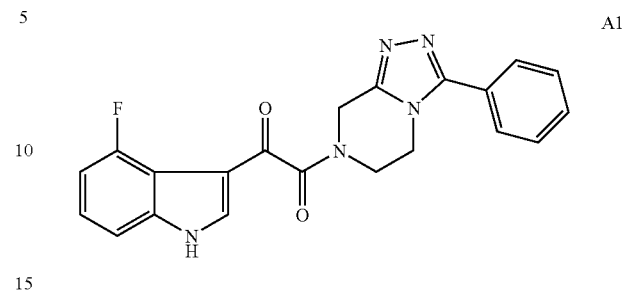

the following reaction scheme may be useful:

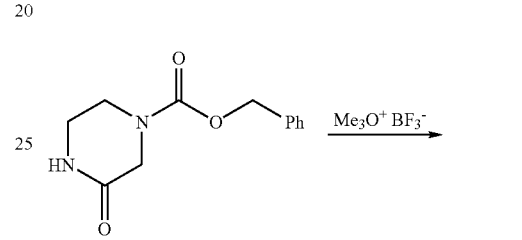

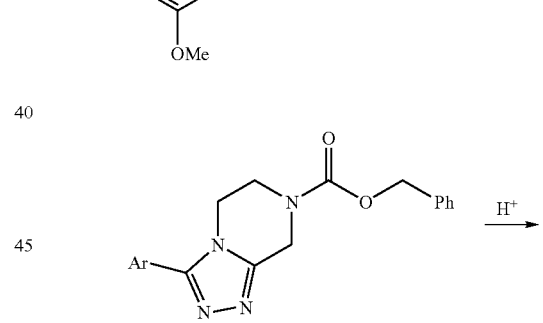

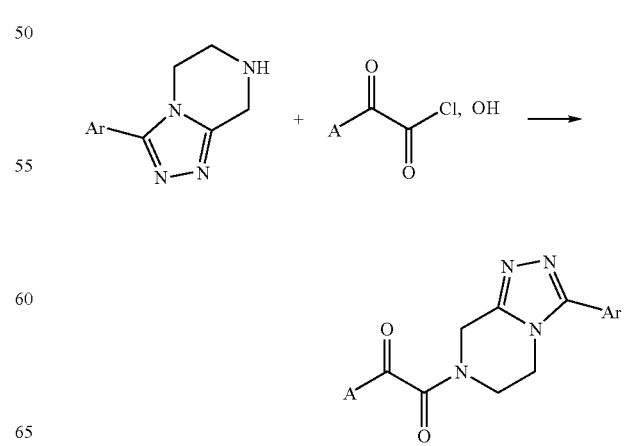

In another embodiment, for the preparation of the following compounds:
B1 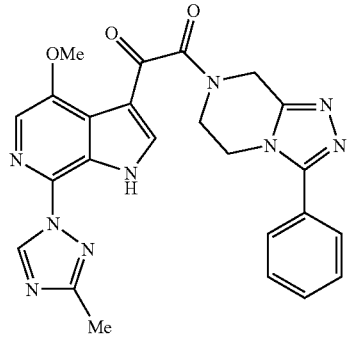
B2 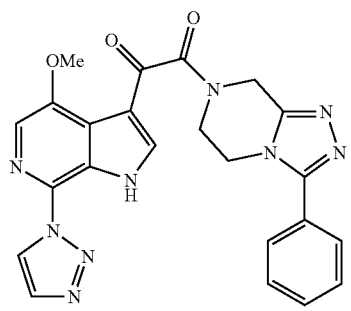
B3 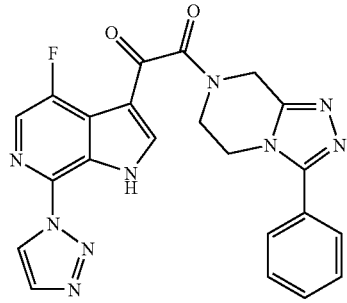
B4 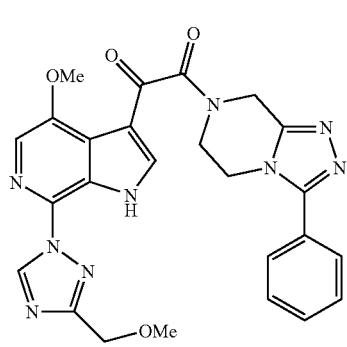
-continued
C1 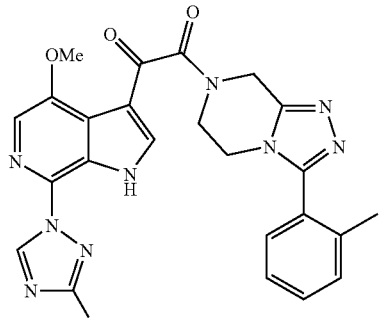
C2 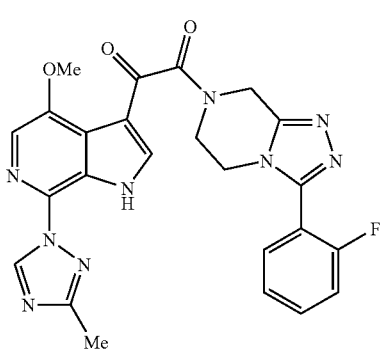
C3 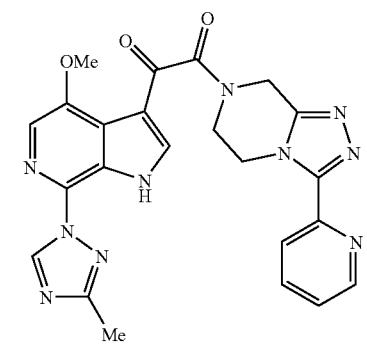
C4 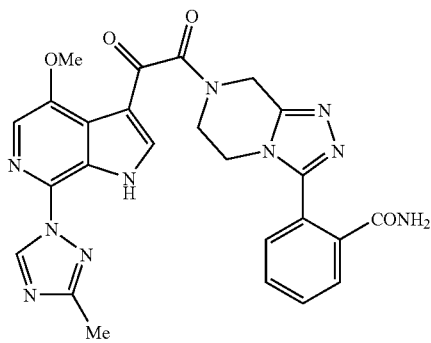

-continued
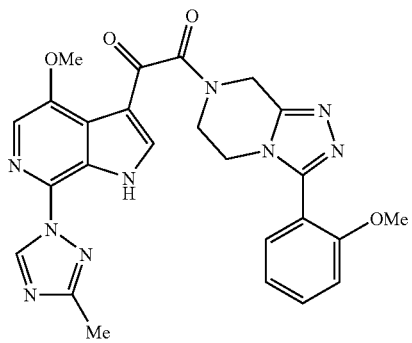
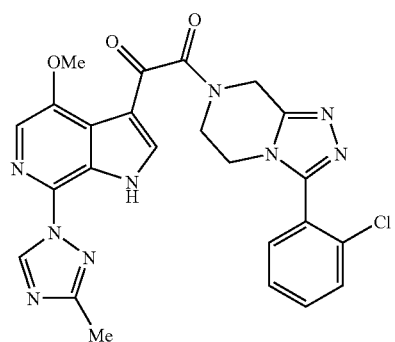
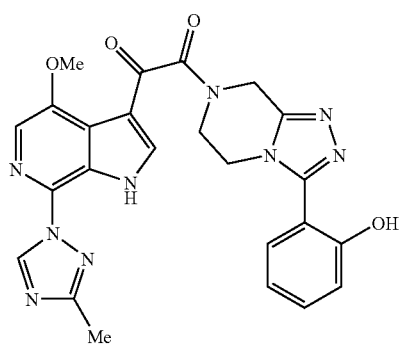
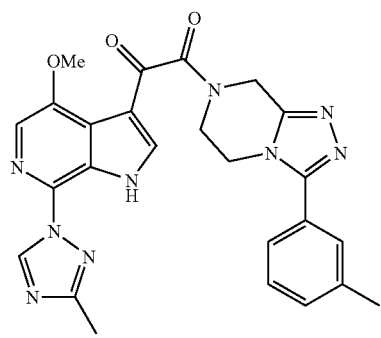
the following schemes may be useful:
C5
Route 1
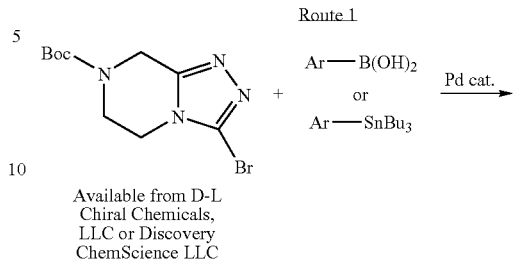
Available from D-L Chiral Chemicals, LLC or Discovery ChemScience LLC
C6
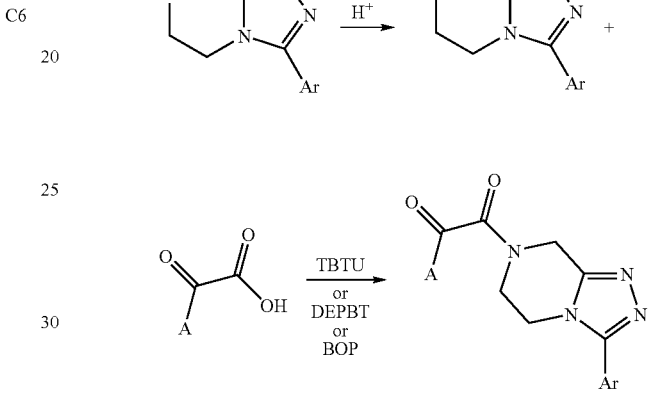
C7
Route 2
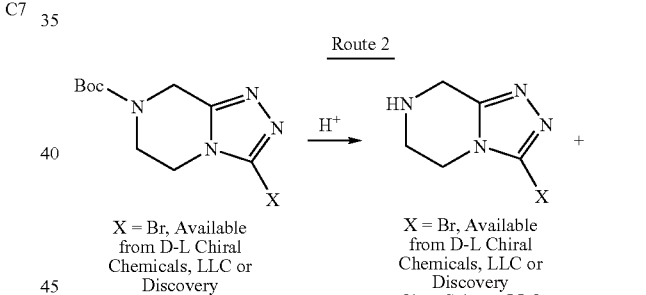
X = Br, Available from D-L Chiral Chemicals, LLC or Discovery ChemScience LLC
X = Br, Available from D-L Chiral Chemicals, LLC or Discovery ChemScience LLC
C8
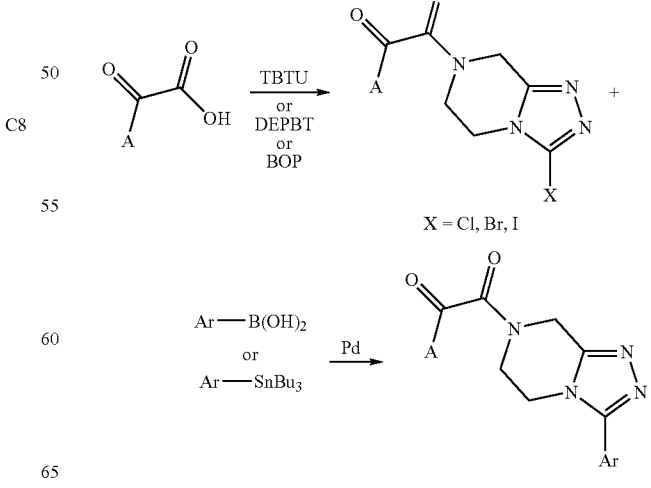
X = Cl, Br, I In another embodiment,
When B=
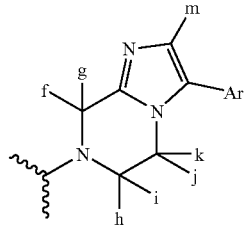
for the following compounds:
D1
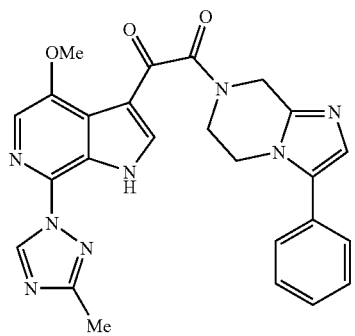
D2
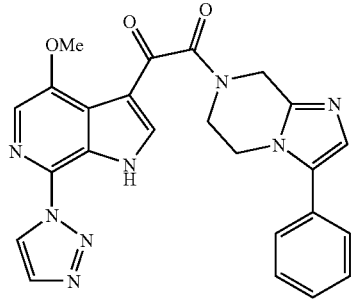
D3
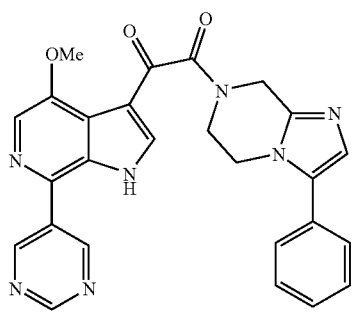
this reaction scheme may be useful:
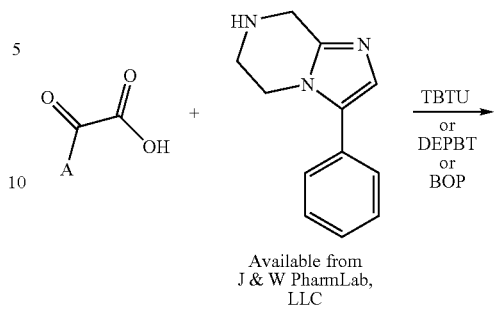
Available from
J & W PharmLab,
LLC
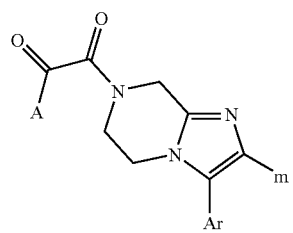
In another embodiment, to prepare the following compounds
E1
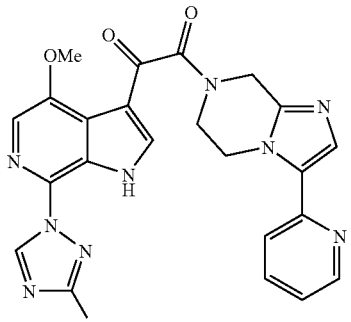
F1
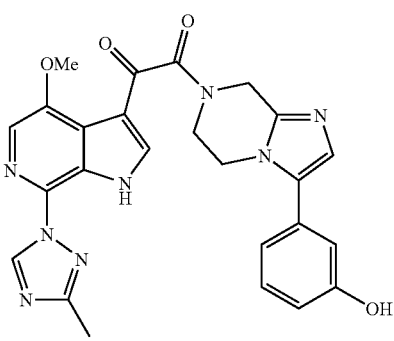
F2
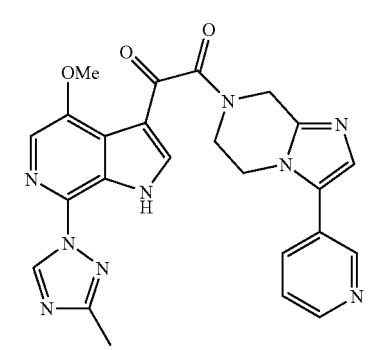

43
-continued
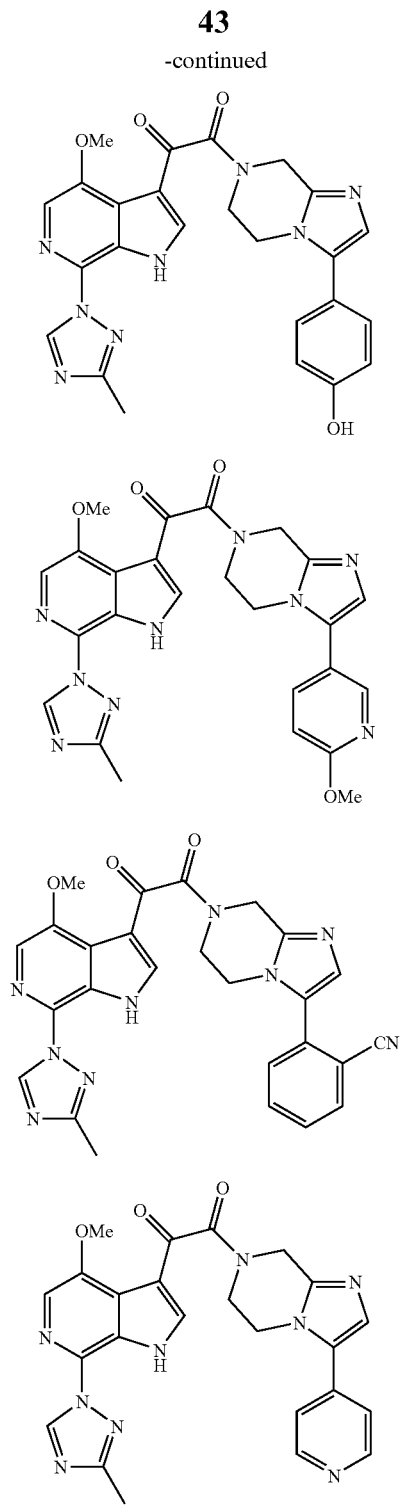
the following reaction schemes may be useful:
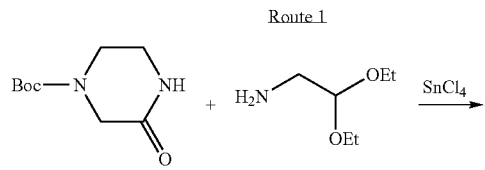
44
-continued
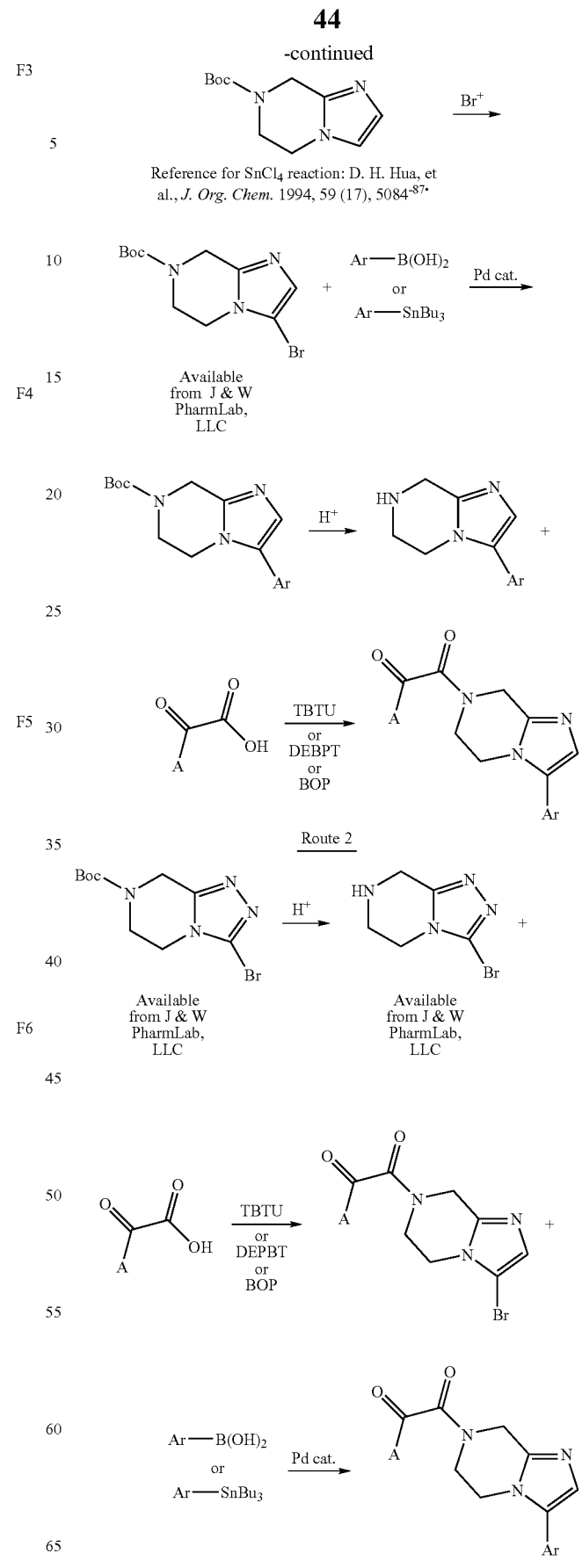
Reference for SnCl₄ reaction: D. H. Hua, et al., *J. Org. Chem.* 1994, 59 (17), 5084-87.
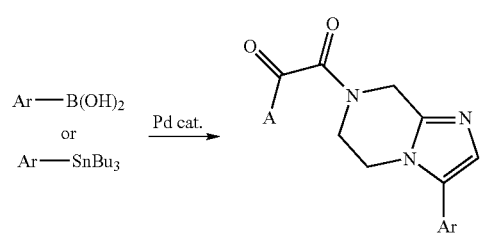

45
In another embodiment, for the preparation of the following compounds:
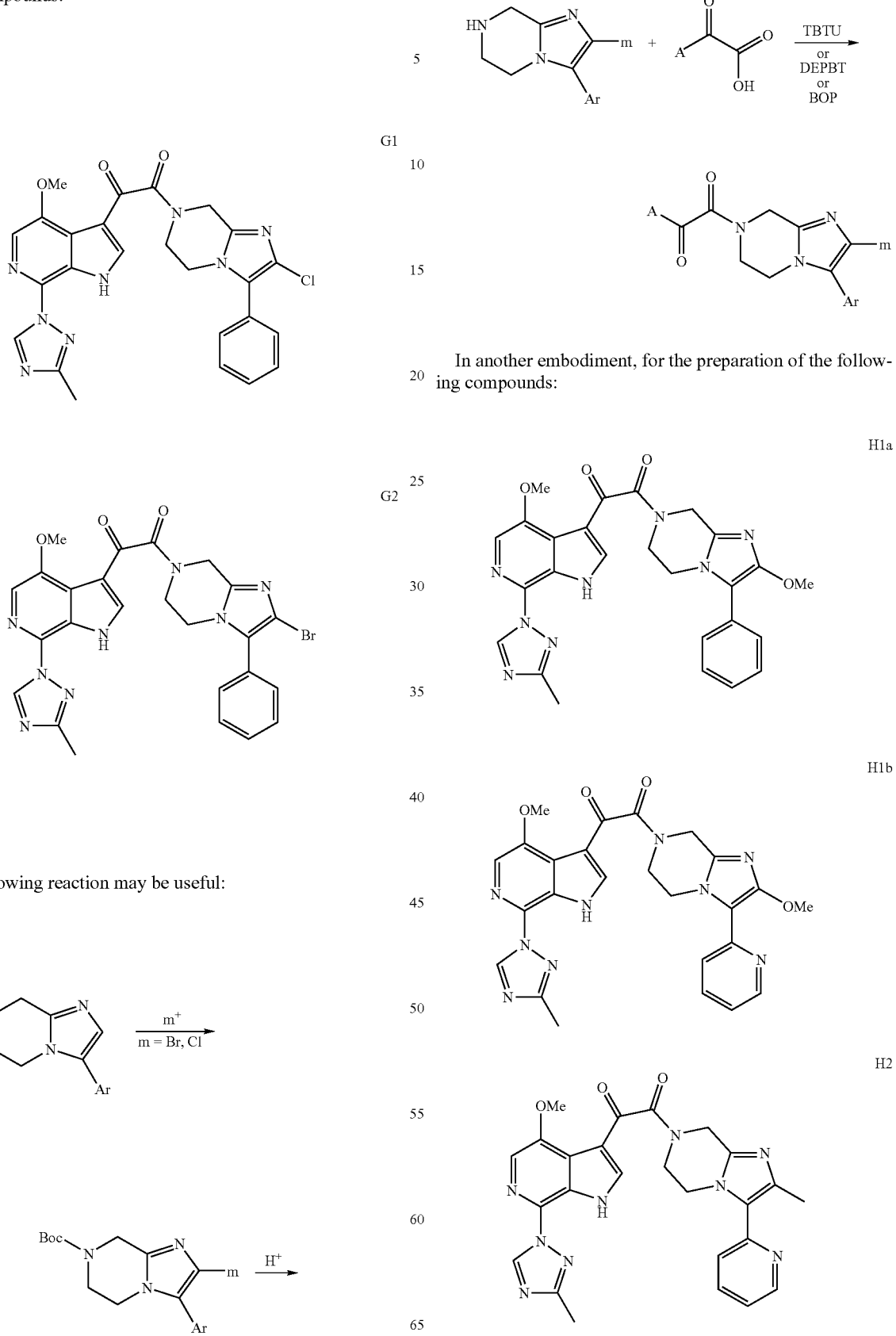
the following reaction may be useful:

the following reaction schemes may be useful:
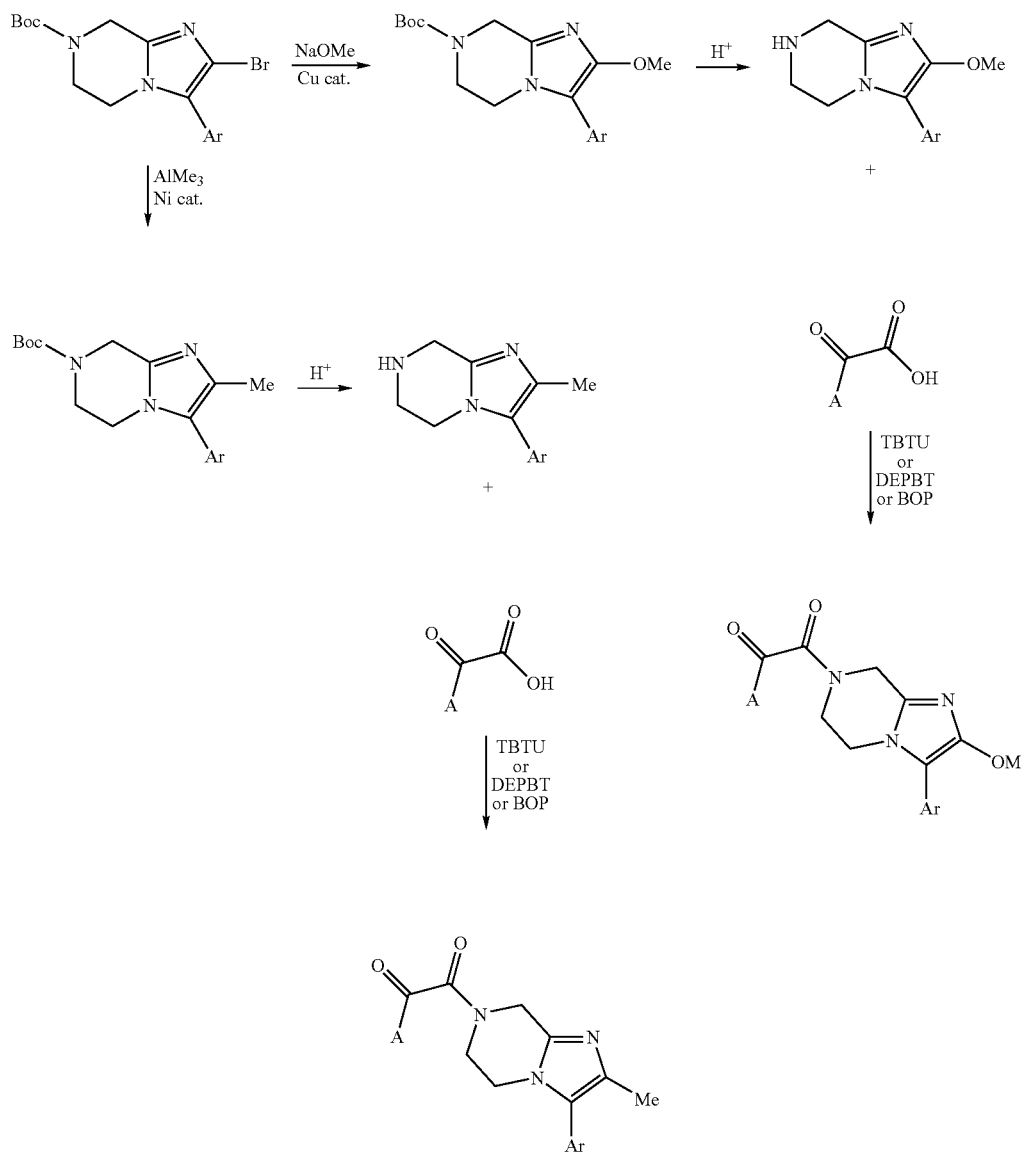
In another embodiment, for the preparation of the following compounds
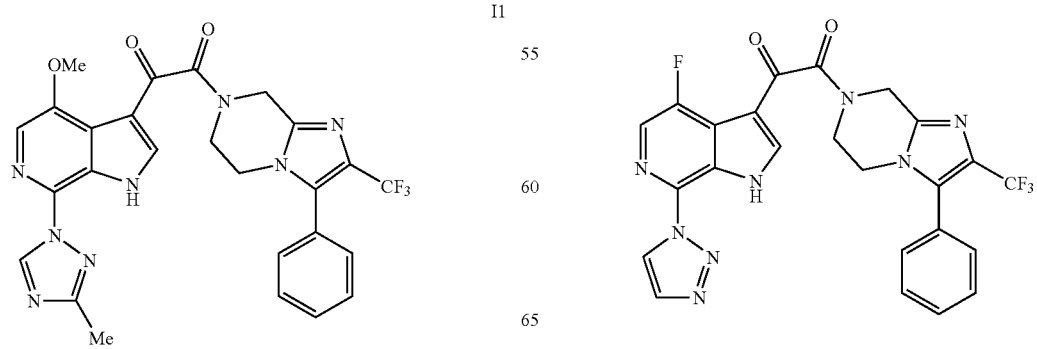
-continued -continued
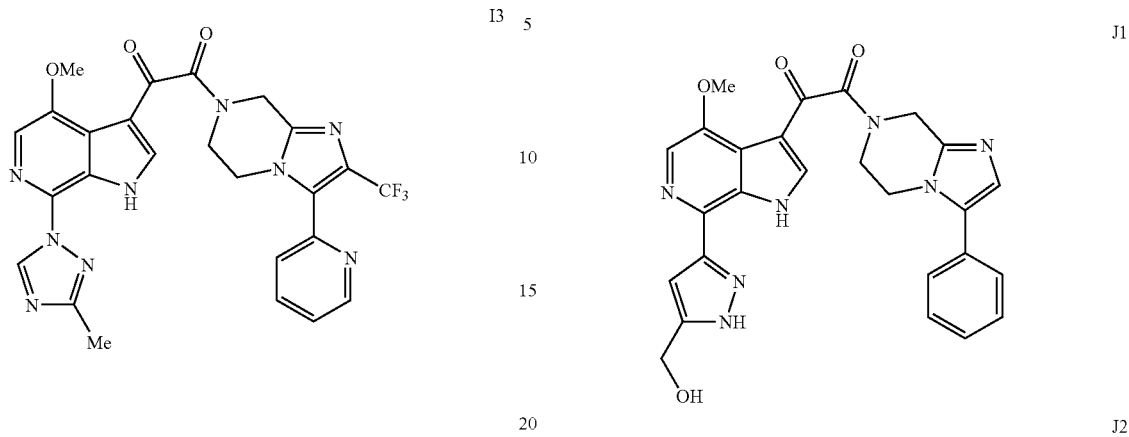
the following reaction scheme may be useful:
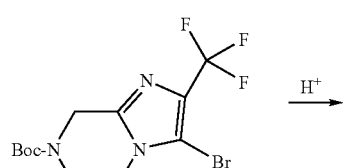
In another embodiment, for the preparation of the following compounds:
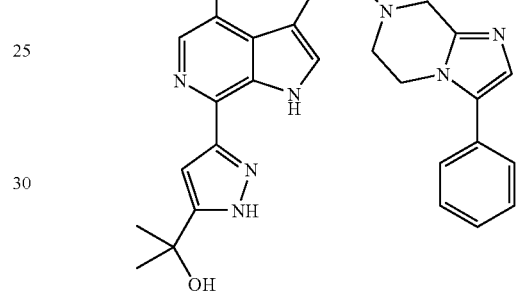
the following reaction scheme may be used:
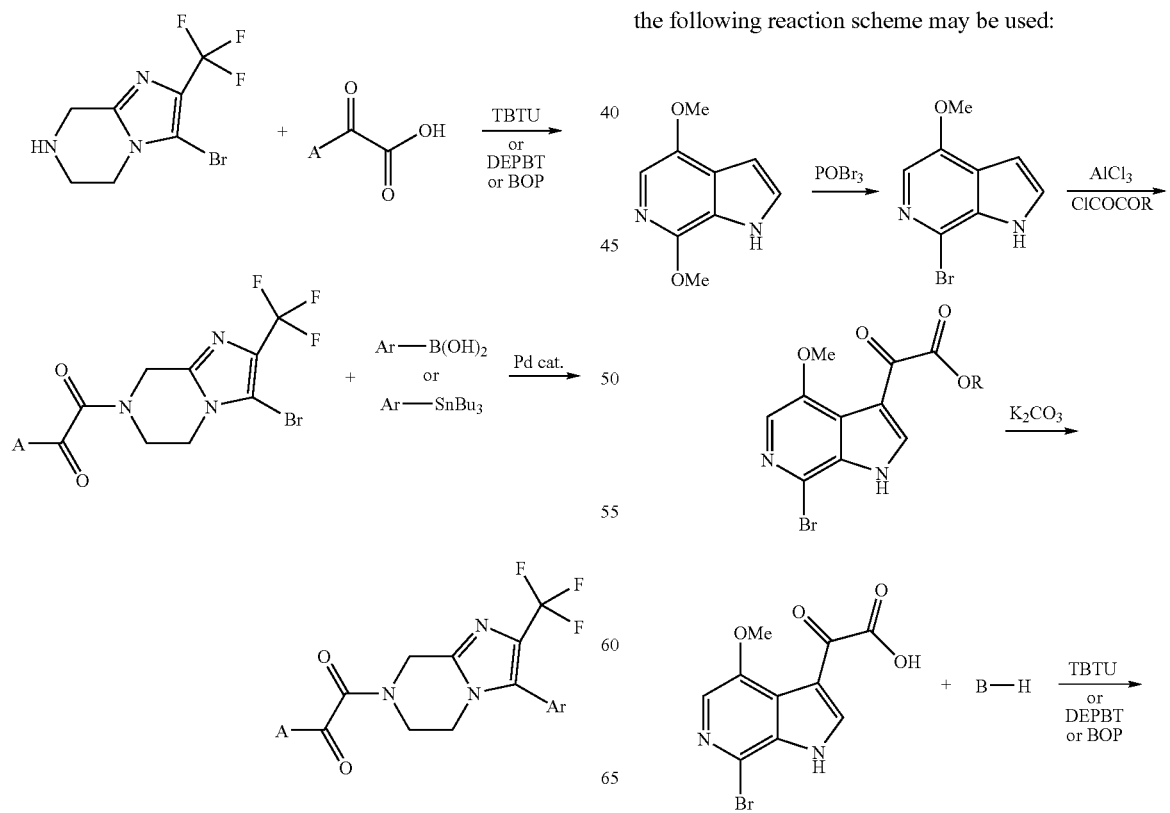

-continued
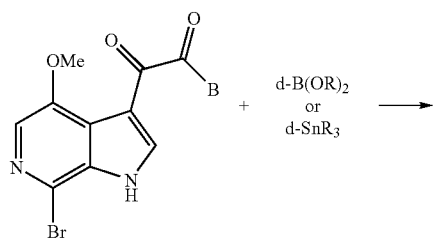
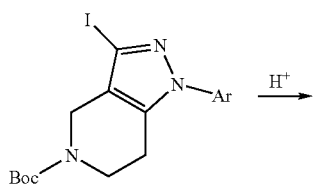
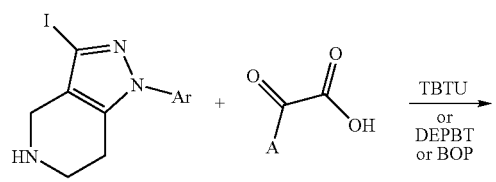
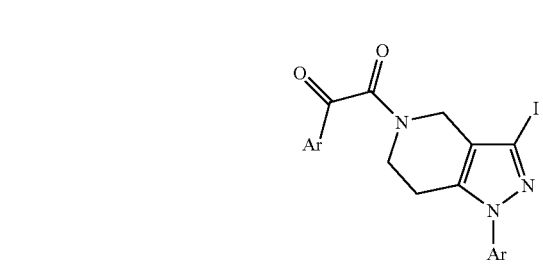
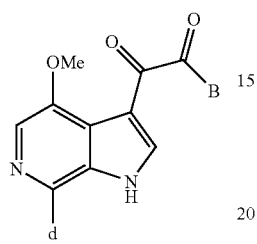
In another embodiment,
When B=
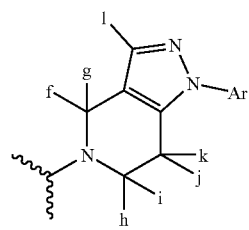
for the following compound:
In another embodiment, for the preparation of the following compounds:
L1
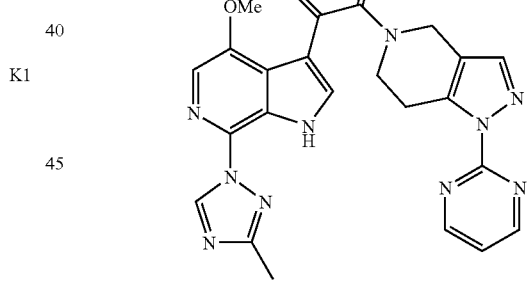
K1
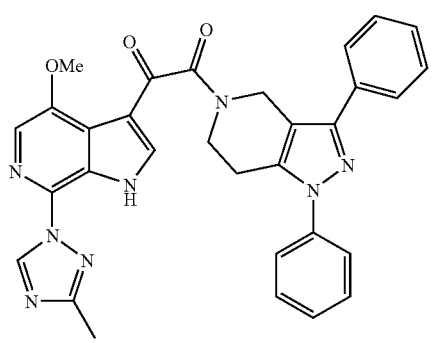
the following reaction scheme may be used:
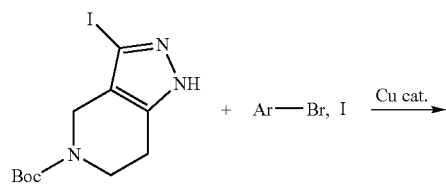
L2
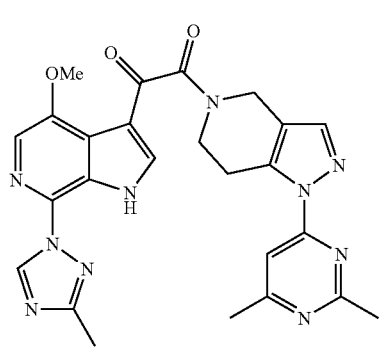

L3
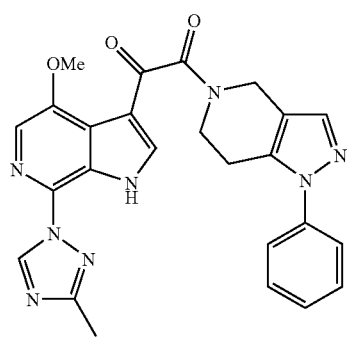
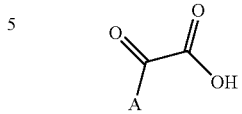
In another embodiment,
When B=
L4
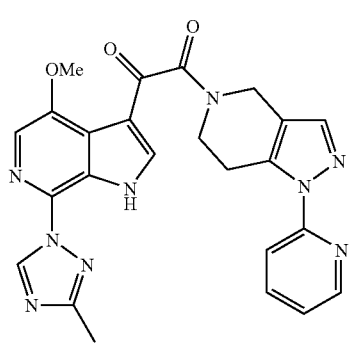
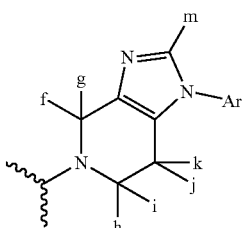
for the preparation of the following compounds:
M1
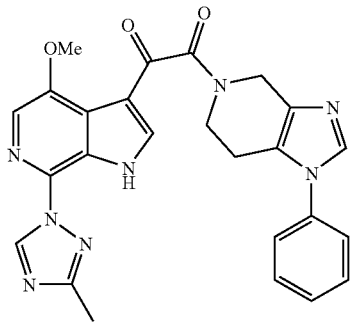
L5
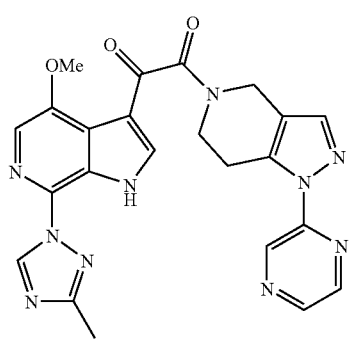
M2
the following reaction may be used:
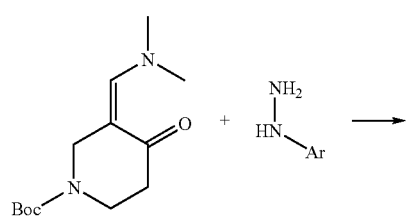
the following reaction scheme may be used:
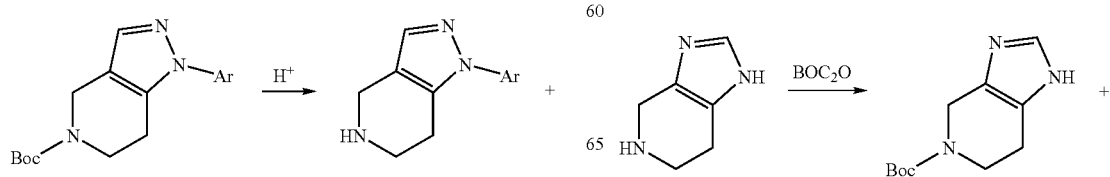

-continued
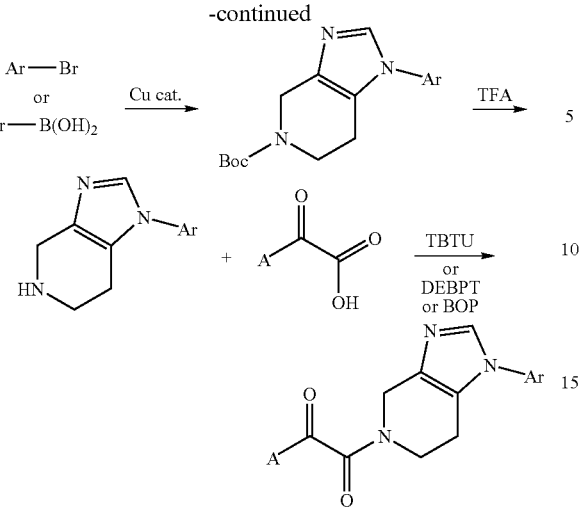
In another embodiment,
When B=
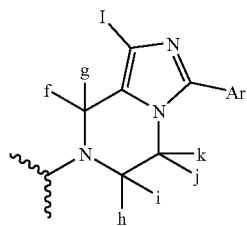
for the preparation of the following compounds:
N1
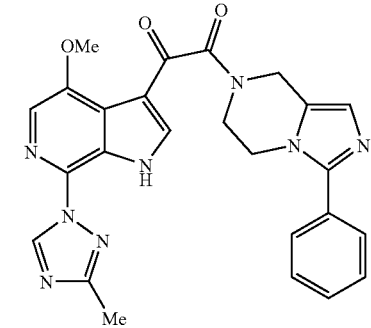
N2
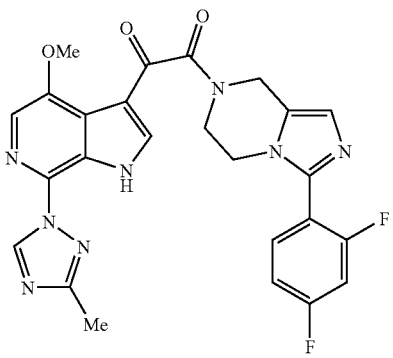
the following reaction schemes may be utilized:
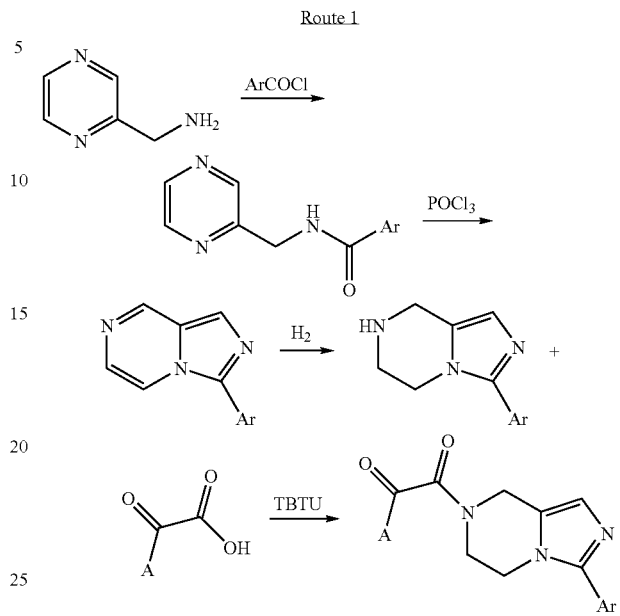
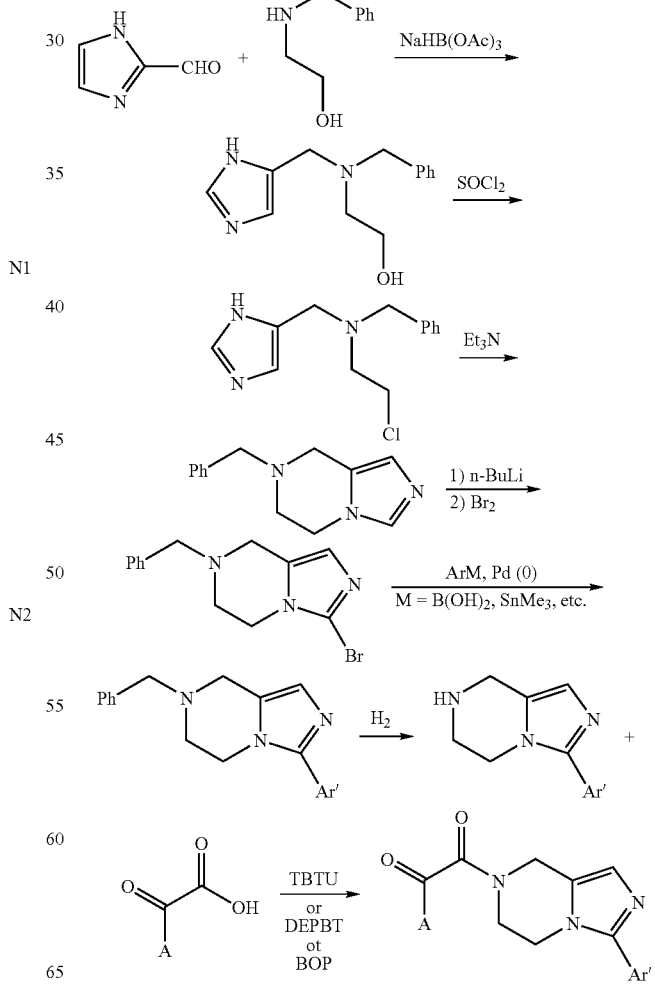

In another embodiment,
When B=

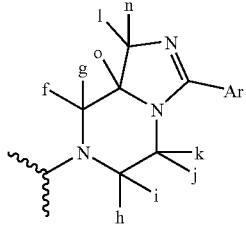

for the preparation of the following compounds:

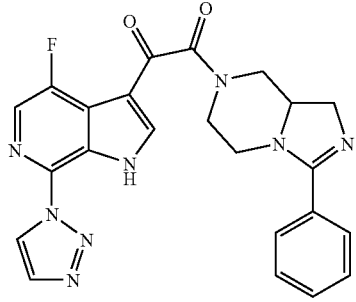

O1

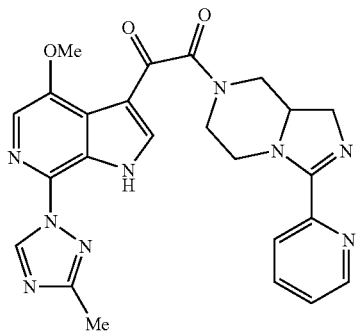

O2 the following reaction scheme may be used:

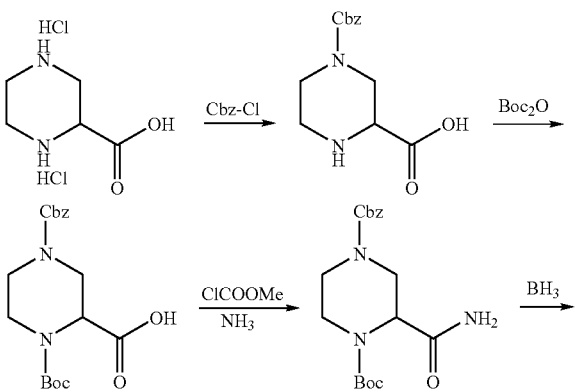

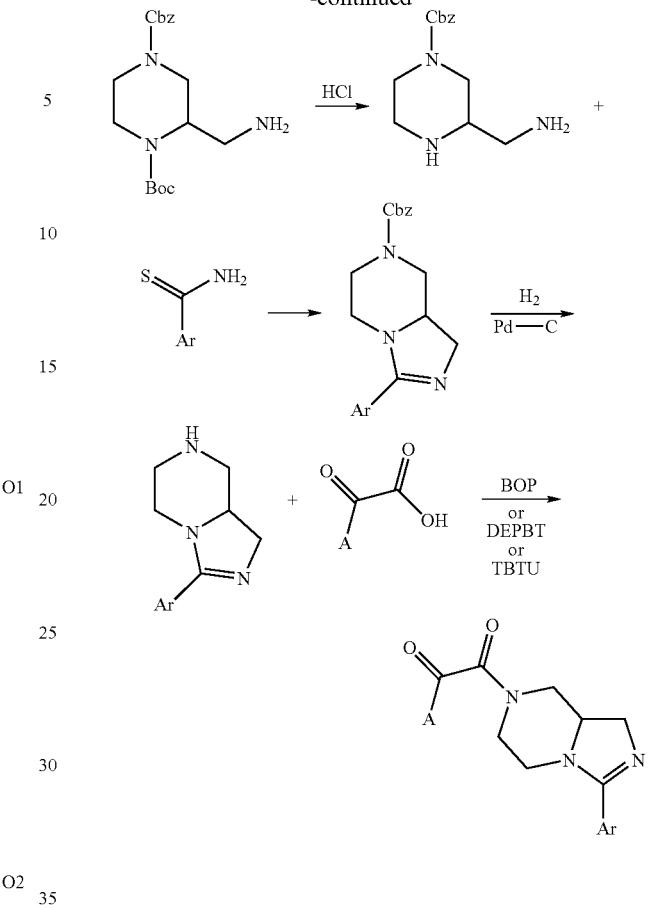

EXAMPLES

The following examples illustrate typical syntheses of the compounds of Formula I as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500 f at 500 MHz (or Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30), and DMSO-d$_6$ ($\delta_H$ 2.50). Standard acronyms were employed to describe the multiplicity patterns: s (singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a MICROMASS® Platform for LC in electrospray mode.

LC/MS Methods (i.e., Compound Identification)

Method 1:
Start % B=0, Final % B=100 over 3 minute gradient (1 minutes collected after run)
Flow Rate=4 mL/Min
Solvent A=5% ACN–95% $H_2O$–10 mm Ammonium Acetate
Solvent B=95% ACN–5% $H_2O$–10 mm Ammonium Acetate
Column: PHENOMENEX® Luna 4.6×50 mm S10

Method 2:
Start % B=0, Final % B=100 over 3 minute gradient (1 minutes collected after run)
Flow Rate=4 mL/Min
Solvent A=10% MeOH–90% $H_2O$–0.1% TFA
Solvent B=90% MeOH–10% $H_2O$–0.1% TFA
Column: PHENOMENEX® Luna 10 u C18 3.0×50 mm Method 3:
Start % B=0, Final % B=100 over 3 minute gradient (1 minutes collected after run)
Flow Rate=4 mL/Min
Solvent A=90% $H_2O$–10% ACN–0.1% TFA
Solvent B=10% $H_2O$–90% ACN–0.1% TFA
Column: SunFire C18 5 u 4.6×50 mm Method 4:
Start % B=0, Final % B=100 over 2 minute gradient (1 minutes collected after run)
Flow Rate=4 mL/Min
Solvent A=90% $H_2O$–10% ACN–0.1% TFA
Solvent B=10% $H_2O$–90% ACN–0.1% TFA
Column: PHENOMENEX® Luna 4.6×50 mm S10

Method 5:
Start % B=0, Final % B=100 over 2 minute gradient (1 minutes collected after run)
Wavelength=220
Flow Rate=4 mL/min
Solvent A=90% $H_2O$–10% MeOH–0.1% TFA
Solvent B=10% $H_2O$–90% MeOH–0.1% TFA
Column: PHENOMENEX® LUNA 4.6×30 mm A10

Method 6:
Start % B=0, Final % B=100 over 2 minute gradient (1 minutes collected after run)
Wavelength=220
Flow Rate=4 mL/min
Solvent A=5% ACN–95% $H_2O$–10 mm Ammonium Acetate
Solvent B=95% ACN–5% $H_2O$–10 mm Ammonium Acetate
Column: PHENOMENEX® LUNA 4.6×30 mm S10

Method 7:
Start % B=0, Final % B=100 over 2 minute gradient (1 minutes collected after run)
Flow Rate=5 mL/Min
Solvent A=5% ACN–95% $H_2O$–10 mm Ammonium Acetate
Solvent B=95% ACN–5% $H_2O$–10 mm Ammonium Acetate
Column: PHENOMENEX® 5 u C18 4.6×30 mm S10

Method 8:
Start % B=0, Final % B=100 over 3 minute gradient (1 minutes collected after run)
Flow Rate=4 mL/Min
Solvent A=10% MeOH–90% $H_2O$–0.1% TFA
Solvent B=90% MeOH–10% $H_2O$–0.1% TFA
Column: PHENOMENEX® Luna 4.6×50 mm S10

Method 9:
Start % B=0, Final % B=100 over 2 minute gradient (1 minutes collected after run)
Flow Rate=4 mL/Min
Solvent A=90% $H_2O$–10% MeOH–0.1% TFA
Solvent B=10% $H_2O$–90% MeOH–0.1% TFA
Column: PHENOMENEX® LUNA 4.6×50 mm S10

Method 10:
Start % B=0, Final % B=100 over 2 minute gradient (1 minutes collected after run)
Wavelength=220
Flow Rate=4 mL/min
Solvent A=5% $H_2O$–95% MeOH–0.1% TFA
Solvent B=95% $H_2O$–5% MeOH–0.1% TFA
Column: PHENOMENEX® LUNA 3.0×50 mm S10

Method 11:
Start % B=0, Final % B=30 over 2 minute gradient (1 minutes collected after run)
Wavelength=220
Flow Rate=4 mL/min
Solvent A=90% $H_2O$–10% MeOH–0.1% TFA
Solvent B=10% $H_2O$–90% MeOH–0.1% TFA
Column: PHENOMENEX® LUNA 4.6×30 mm S10

Method 12:
Start % B=0, Final % B=50 over 2 minute gradient (1 minutes collected after run)
Wavelength=220
Flow Rate=4 mL/min
Solvent A=90% $H_2O$–10% MeOH–0.1% TFA
Solvent B=10% $H_2O$–90% MeOH–0.1% TFA
Column: PHENOMENEX® LUNA 4.6×30 mm S10

Compounds purified by preparative HPLC were diluted in methanol (1.2 ml) and purified using the following methods on a Shimadzu LC-10A automated preparative HPLC system.

Preparative HPLC Method (i.e., Compound Purification)
Purification Method: Initial gradient (40% B, 60% A) ramp to final gradient (100% B, 0% A) over 20 minutes, hold for 3 minutes (100% B, 0% A)
Solvent A: 10% MeOH/90% $H_2O$/0.1% Trifluoroacetic Acid
Solvent B: 10% $H_2O$/90% MeOH/0.1% Trifluoroacetic Acid
Column: YMC C18 S5 20×100 mm column
Detector Wavelength: 220 nm Example A Preparation of Compound A of Formula 1

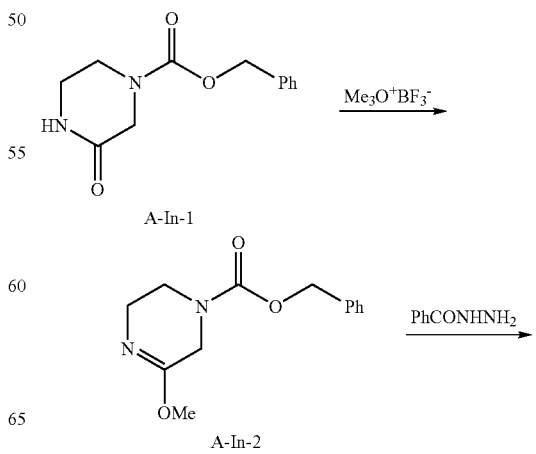

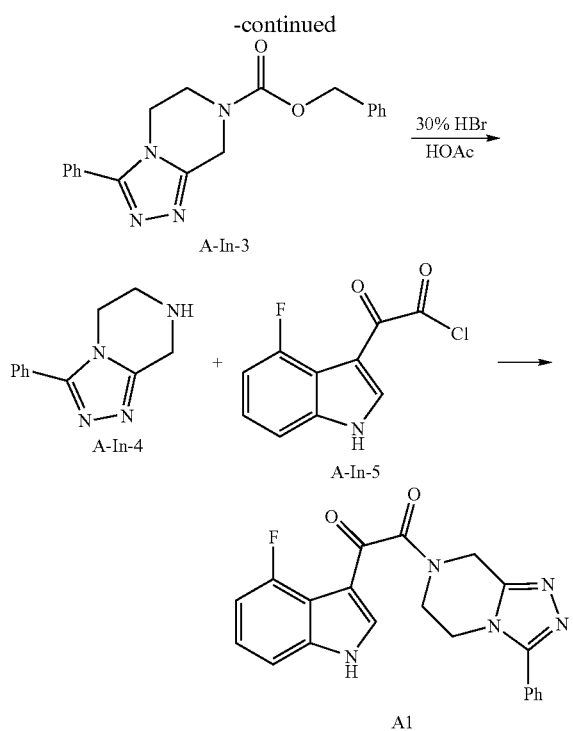

Process for the Preparation of Compound A-In-2:

This compound was prepared by the method described by Bryant, H. J. et al., in WO 01/44250.

To a stirred and cold (ice-bath cooling) suspension of benzyl 3-oxopiperazine-1-carboxylate (A-In-1) (1.00 g) and $K_2CO_3$ (11.8 g) in $CH_2Cl_2$ (40 mL) was added under $N_2$ trimethyloxonium tetrafluoroborate (2.20 g, from Aldrich) in one portion. The cooling bath was removed and the mixture was stirred at room temperature under $N_2$ for 19 h. This mixture was poured into water (40 mL) under ice-cooling and the organic phase was collected. The aqueous phase was extracted with $CH_2Cl_2$. The combined $CH_2Cl_2$ phases were washed with water (20 mL), then with brine, dried ($Na_2SO_4$) and concentrated. The crude residual oil was purified by silica gel column chromatography (5% MeOH/$CH_2Cl_2$) to give the title compound A-In-2 as colorless oil.

Process for the Preparation of Compound A-In-3 from A1-In-2:

A mixture of A1-In-2 (248 mg) and benzoic acid hydrazide (136 mg) in toluene (25 mL) was heated at reflux with a Dean-Stark trap for 24 h. After cooling, the mixture was concentrated in vacuo, and the residue was purified by silica gel column chromatography (5% MeOH/$CH_2Cl_2$), followed by crystallization from $Et_2O$ gave the title compound A-In-3 as white crystals.

Process for the Preparation of Compound A-In-4 from A-In-3:

A mixture of A1-In-3 in 30% HBr in HOAc (1.7 mL) was stirred at room temperature for 3 h. Concentration under vacuum provided an aqueous solution which was extracted with $CH_2Cl_2$ (15 mL). The organic layer was washed with saturated aqueous $NaHCO_3$, dried ($Na_2SO_4$) and concentrated. The residue was purified by silica gel column chromatography (10% of 10% c-$NH_4OH$/MeOH in $CH_2Cl_2$) to give A-In-4 as white solid.

Process for the Preparation of Compound A1 from A-In-4:

To a stirred solution of A-In-4 (30 mg) and A-In-5 (40 mg) in $CH_2Cl_2$ (2 mL) under $N_2$ was injected diisopropylethylamine (31 μL) and the mixture was stirred for 1 h. After removal of solvents under vacuum, the residue was purified by silica gel column chromatography (10% MeOH/$CH_2Cl_2$), followed by trituration from $Et_2O$ to provide the title compound A1 as off-white crystalline powder.

Characterization of A-In and A (Table A):

TABLE A

| Compound No. | Structure | MS (M + H)+ Calcd. | MS (M + H)+ Observ. and Retention Time and NMR |
|---|---|---|---|
| A-In-2 | 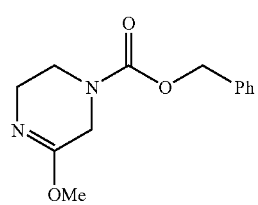 | 249 | 249. $^1$H-NMR (CDCl$_3$, 500 MHz): δ ppm 3.46-3.49 (2 H, m), 3.56 (2 H, m), 3.74 (3 H, br.s), 3.99 (2 H, br.s), 5.15 (2 H, s), 7.33-7.38 (5 H, m). |
| A-In-3 | 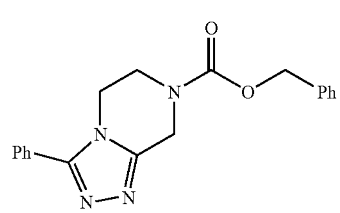 | 335 | 335. $^1$H-NMR (CDCl$_3$) δppm 3.87 (2 H, br.s), 4.08 (2 H, br.s), 4.95 (2 H, s), 5.18 (2 H, s), 7.35 (5 H, s), 7.46 (3 H, br.s), 7.63 (2 H, br). $^{13}$C-NMR (CDCl$_3$): δppm 41.0, 41.7, 44.0, 68.2, 126.5, 128.2, 128.6, 128.8, 129.2, 130.3, 135.9, 148.3, 153.4, 155.0. |
| A-In-4 | 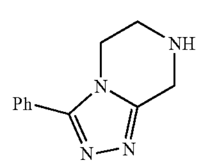 | 201 | 201. $^1$H-NMR (CDCl$_3$) δppm 2.37 (1 H, br.s), 3.17 (2 H, t, J = 5.5 Hz), 4.00 (2 H, t, J = 5.5 Hz), 4.20 (2 H, s), 7.38-7.48 (3 H, m), 7.63 (2 H, dd, J = 6.6, 2.9 Hz). |

TABLE A-continued

| Compound No. | Structure | MS (M + H)+ Calcd. | MS (M + H)+ Observ. and Retention Time and NMR |
|---|---|---|---|
| A-1 | (structure shown) | 390 | 390. <br> ¹H-NMR (300 MHz, DMSO-$d_6$): δppm 3.81 (1.5 H, t, J = 5 Hz), 4.05-4.09 (0.5 H, m), 4.12 (1.5 H, t, J = 5 Hz), 4.32 (0.5 H, t, J = 5 Hz), 4.84 (0.5 H, s), 5.03 (1.5 H, s), 7.03 (1 H, m), 7.24-7.34 (1 H, m), 7.37, 7.40 (1 H, 2 s, 3:1), 7.49-7.60 (3 H, m), 7.68-7.76 (2 H, m), 8.29 (0.25 H, d, J = 3 Hz), 8.43 (0.75 H, d, J = 2 Hz), 12.68 (1 H, br.s). |

Example B

Preparation of Compounds B of Formula 1

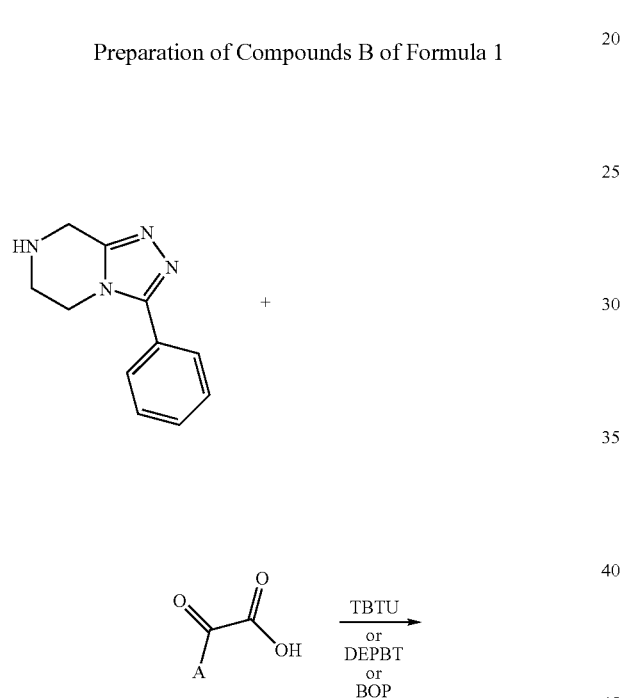

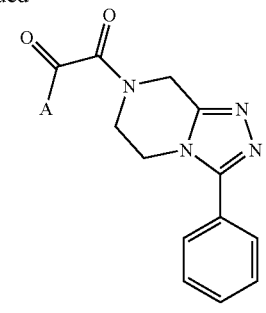

General Process for the Preparation of Compound B from 3-Phenyl-5,6,7,8-tetrahydro-[1,2,4]triazolo[4,3-a]pyrazine:

2-Keto acid (1 eq.), 3-phenyl-5,6,7,8-tetrahydro-[1,2,4]triazolo[4,3-a]pyrazine (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% $NaHCO_3$ or $NH_4Cl$ aqueous solution. The aqueous layer was extracted with ethyl acetate or methylene chloride. The organic phase combined and dried over anhydrous $MgSO_4$. Concentration in vacuo provided a crude product, which was purified by trituration, or recrystallization, or silica gel column chromatography, or Shimadzu automated preparative HPLC system.

Characterization of B-In and B (Table B):

TABLE B

| Compound No. | Structure | MS (M + H)+ Calcd. | MS (M + H)+ Observ. and Retention Time and NMR |
|---|---|---|---|
| B1 | (structure shown) | 484 | 484, Rf = 1.36 min (Method 5). <br> ¹H NMR (500 MHz, MeOD): δppm 9.10 (s, 1 H), 8.30-8.32 (m, 1 H), 7.75 (s, 1 H), 7.63-7.68 (m, 2 H), 7.51-7.56 (m, 3 H), 5.02-5.20 (m, 2 H), 3.93-4.32 (m, 7 H), 2.53 (s, 3 H). |

TABLE B-continued
| Compound No. | Structure | MS (M + H)+ Calcd. | MS (M + H)+ Observ. and Retention Time and NMR |
|---|---|---|---|
| B2 | 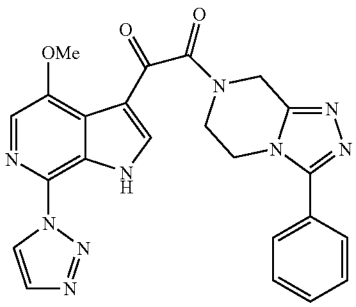 | 470 | 470, Rf = 1.40 min (Method 5). ¹H NMR (500 MHz, DMSO-d₆): δppm 12.84 (s, 1 H), 8.93 (s, 1 H), 8.29-8.40 (m, 1 H), 8.05-8.10 (m, 1 H), 7.93-8.00 (m, 1 H), 7.71-7.81 (m, 2 H), 7.50-7.58 (m, 3 H), 4.87-5.10 (m, 2 H), 3.85-4.33 (m, 7 H). |
| B3 | 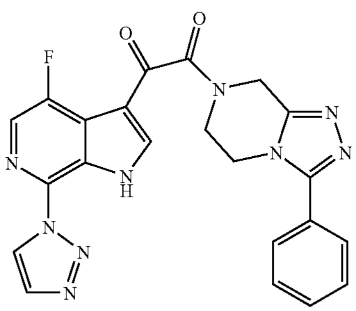 | 458 | 458, Rf = 1.53 min (Method 5). ¹H NMR (500 MHz, DMSO-d₆): δppm 13.10 (s, 1 H), 9.01 (s, 1 H), 8.41-8.62 (m, 1 H), 8.29-8.33 (m, 1 H), 8.07-8.15 (m, 1 H), 7.70-7.80 (m, 2 H), 7.49-7.58 (m, 3 H), 4.91-5.09 (m, 2 H), 4.13-4.34 (m, 2 H), 3.85-4.12 (m, 2 H). |
| B4 | 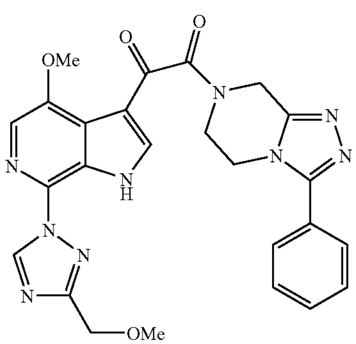 | 514 | 514, Rf = 1.41 min (Method 1). ¹H NMR (500 MHz, MeOD): δppm 9.25 (s, 1 H), 8.33-8.40 (m, 1 H), 7.81-7.85 (m, 1 H), 7.66-7.74 (m, 2 H), 7.53-7.60 (m, 3 H), 5.02-5.24 (m, 2 H), 4.70 (s, 2 H), 3.93-4.37 (m, 7 H), 3.52 (s, 3 H). |
Example C
Preparation of Compounds C of Formula 1
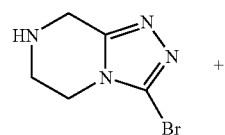
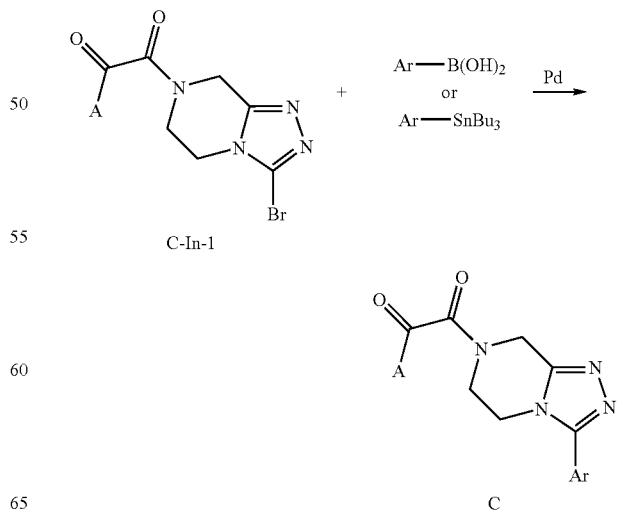

General Process for the Preparation of Compound C-In-1 from 3-Bromo-5,6,7,8-tetrahydro-[1,2,4]triazolo[4,3-a]pyrazine:

2-Keto acid (1 eq.), 3-bromo-5,6,7,8-tetrahydro-[1,2,4]triazolo[4,3-a]pyrazine (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% Na$_2$CO$_3$ or 5% NaHCO$_3$ or NH$_4$Cl aqueous solution. The aqueous layer was extracted with ethyl acetate or methylene chloride. The organic phase combined and dried over anhydrous MgSO$_4$. Concentration in vacuo provided a crude product, which was purified by trituration, or recrystallization, or silica gel column chromatography, or Shimadzu automated preparative HPLC system, to afford C-In-1.

General Process for the Preparation of Compound C from C-In-1:

C-In-1 (1 eq.), boronic or stannane agent (1-10 eq.) and palladium catalyst (e.g., tetrakis(triphenylphosphine)palladium, bis(diphenylphosphino)ferrocene palladium (II) chloride, bis(triphenylphosphine)palladium(II) chloride) (0.05-1 eq.) with or without base (e.g., Cs$_2$CO$_3$, K$_2$CO$_3$, NaCO$_3$, Na$_3$PO$_4$, NaH$_2$PO$_4$, Et$_3$N, iPr$_2$NEt, t-BuOK, t-BuONa) were combined in DMF or dioxane, with or without water. The reaction was either heated to 100° C. to 200° C. in sealed tube or carried out in the microwave synthesizer for 20 minutes to 72 hours. The mixture was diluted with MeOH and filtered. The filtration was concentrated and purified by trituration, or recrystallization, or silica gel column chromatography, or Shimadzu automated preparative HPLC system, to afford Compound C.

Characterization of C-In and C (Table C):

TABLE C

| Compound No. | Structure | MS (M + H)$^+$ Calcd. | MS (M + H)$^+$ Observ. and Retention Time and NMR |
|---|---|---|---|
| C-In-1 | 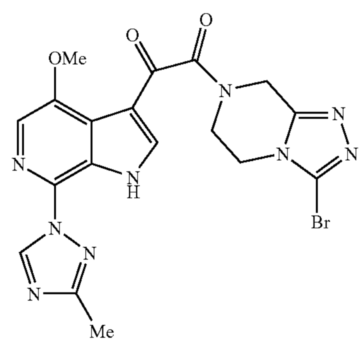 | 486 | 486, Rf = 1.35 min (Method 9). |
| C1 | 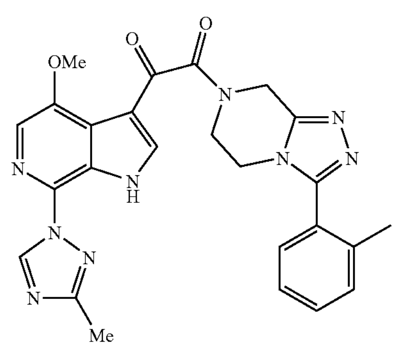 | 498 | 498, Rf = 1.45 min (Method 5). $^1$H NMR (500 MHz, MeOD): δppm 9.12-9.18 (m, 1 H), 8.34 (s, 1 H), 7.78-7.84 (m, 1 H), 7.31-7.47 (m, 4 H), 5.01-5.25 (m, 2 H), 3.98-4.23 (m, 4 H,) 3.92-3.95 (m, 3 H), 2.50-2.58 (m, 3 H), 2.25-2.32 (m, 3 H). |
| C2 | 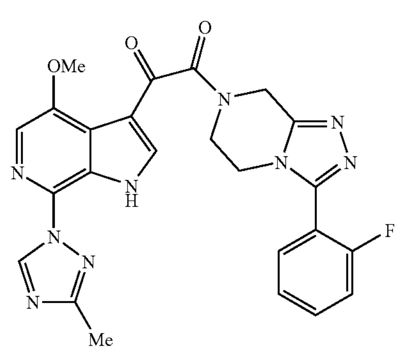 | 502 | 502, Rf = 1.40 min (Method 5). $^1$H NMR (500 MHz, MeOD): δppm 9.15 (s, 1 H), 8.31-8.39 (m, 1 H), 7.76-7.83 (m, 1 H), 7.23-7.62 (m, 4 H), 5.00-5.26 (m, 2 H), 3.98-4.23 (m, 4 H), 3.84-3.98 (m, 3 H), 2.54 (s, 3 H). |

TABLE C-continued

| Compound No. | Structure | MS (M + H)+ Calcd. | MS (M + H)+ Observ. and Retention Time and NMR |
|---|---|---|---|
| C3 | 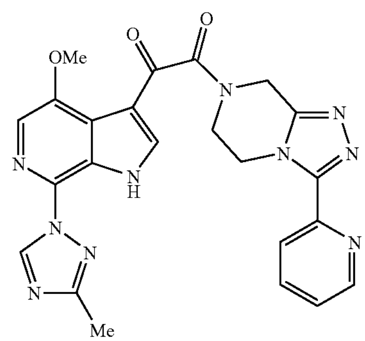 | 485 | 485, Rf = 1.12 min (Method 6). |
| C4 | 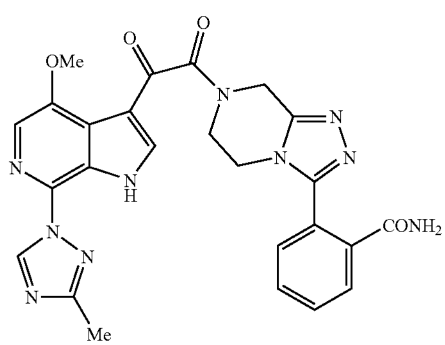 | 527 | 527, Rf = 1.70 min (Method 8). |
| C5 | 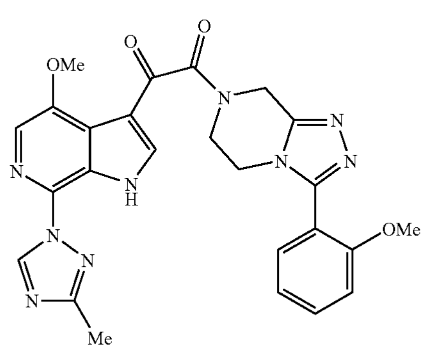 | 514 | 514, Rf = 1.44 min (Method 1). |
| C6 | 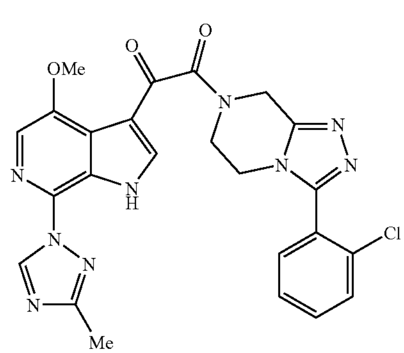 | 518 | 518, Rf = 1.52 min (Method 1). |

TABLE C-continued

| Compound No. | Structure | MS (M + H)+ Calcd. | MS (M + H)+ Observ. and Retention Time and NMR |
|---|---|---|---|
| C7 | 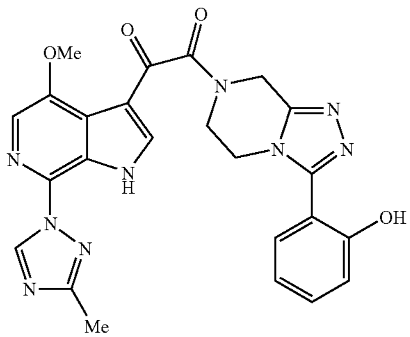 | 498 (M − H) | 498 (M − H)+, Rf = 1.36 min (Method 1). |
| C8 | 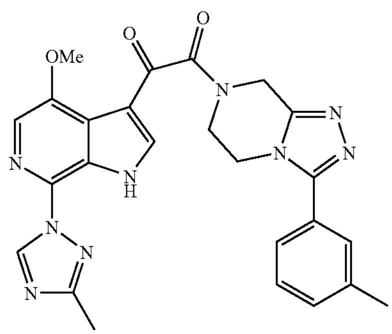 | 498 | 498. |

Example D

Preparation of Compounds D of Formula 1

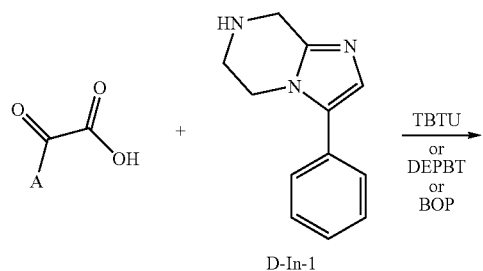

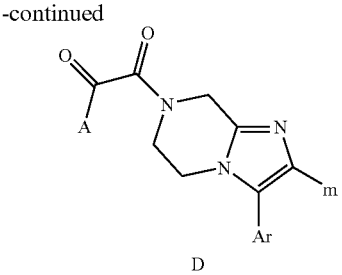

General Process for the Preparation of Compound D from D-In-1:

2-Keto acid (1 eq.), D-In-1 (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% $NaHCO_3$ or $NH_4Cl$ aqueous solution. The aqueous layer was extracted with ethyl acetate or methylene chloride. The organic phase combined and dried over anhydrous $MgSO_4$. Concentration in vacuo provided a crude product, which was purified by trituration, or recrystallization, or silica gel column chromatography, or Shimadzu automated preparative HPLC system.

Characterization of D (Table D):
TABLE D
| Compound No. | Structure | MS (M + H)+ Calcd. | MS (M + H)+ Observ. and Retention Time and NMR |
|---|---|---|---|
| D1 | 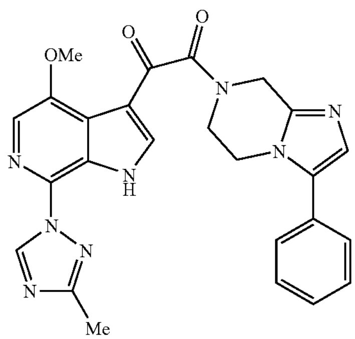 | 483 | 483, Rf = 1.32 min (Method 5). ¹H NMR (500 MHz, CDCl₃) δppm 11.07-11.13 (m, 1 H), 9.08 (s, 1 H), 8.22-8.27 (m, 1 H), 7.34-7.45 (m, 5H), 7.10-7.17 (m, 1 H), 4.93-5.10 (m, 2 H), 3.94-4.15 (m, 4H,) 3.85-3.91 (m, 3 H), 2.55 (s, 3 H). |
| D2 | 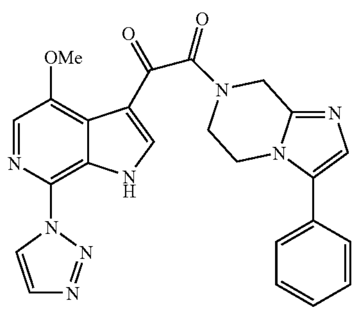 | 469 | 469, Rf = 1.31 min (Method 5). ¹H NMR (500 MHz, MeOD): δppm 8.74 (s, 1 H), 8.31-8.39 (m, 1 H), 7.89 (s, 1 H), 7.83 (s, 1 H), 7.34-7.44 (m, 5H), 7.03-7.08 (m, 1 H), 4.87-5.05 (m, 2 H), 3.89-4.20 (m, 7 H). |
| D3 | 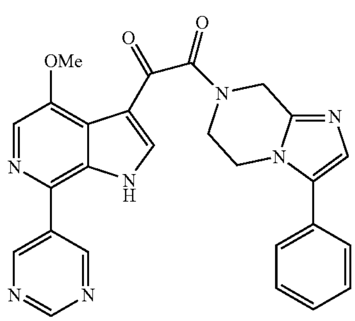 | 480 | 480, Rf = 1.00 min (Method 5). ¹H NMR (500 MHz, MeOD): δppm 9.27-9.32 (m, 1 H), 9.15-9.21 (m, 2 H), 8.43-8.49 (m, 1 H), 8.18 (s, 1 H), 7.49-7.58 (m, 6 H), 5.19-5.32 (m, 2 H), 4.06-4.34 (m, 7 H). |
Example E
Preparation of Compounds E of Formula 1
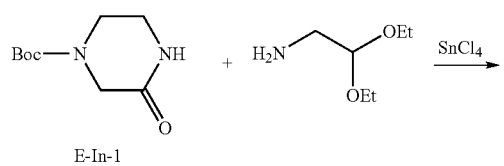
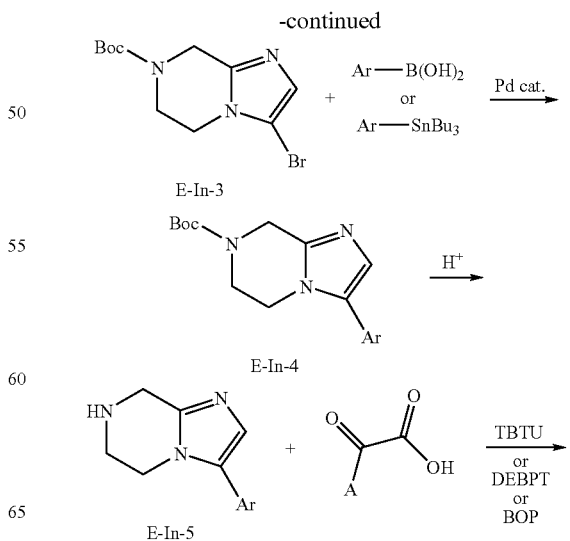

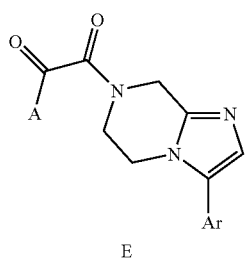

General Process for the Preparation of Compound E-In-2 from E-In-1:

A round bottom flask was charged with E-In-1 (1 eq.), $CH_2Cl_2$, mesitylene and Tin(IV) chloride (0.3 eq.). The mixture was brought to reflux then aminoacetaldehyde diethyl acetal (2 eq.) was added slowly. The reaction was refluxed for 2-3d. The reaction was diluted with $CH_2Cl_2$ and filtered through activated charcoal and the filtrate was evaporated giving a solid which was purified by trituration, or recrystallization, or silica gel column chromatography, or Shimadzu automated preparative HPLC system, to afford E-In-2.

General Process for the Preparation of Compound E-In-3 from E-In-2:

A round bottom flask was charged with E-In-2 (1 eq.), $CCl_4$ and N-bromosuccinimide (1 eq.). The solution was refluxed for 30 minutes then allowed to cool. The $CCl_4$ solution was decanted off a brown solid and evaporated. The residue was purified by trituration, or recrystallization, or silica gel column chromatography, or Shimadzu automated preparative HPLC system, to afford E-In-3.

General Process for the Preparation of Compound E-In-4 from E-In-3:

E-In-3 (1 eq.), boronic or stannane agent (1-10 eq.) and palladium catalyst (e.g., tetrakis(triphenylphosphine)palladium, bis(diphenylphosphino)ferrocene palladium (II) chloride, bis(triphenylphosphine)palladium(II) chloride) (0.05-1 eq.) with or without base (e.g., $Cs_2CO_3$, $K_2CO_3$, $NaCO_3$, $Na_3PO_4$, $NaH_2PO_4$, $Na_2HPO_4$, $Et_3N$, $iPr_2NEt$, t-BuOK, t-BuONa) were combined in DMF or dioxane, with or without water. The reaction was either heated to 100° C. to 200° C. in sealed tube or carried out in the microwave synthesizer for 20 minutes to 72 hours. The mixture was diluted with MeOH and filtered. The filtration was concentrated and purified by HPLC or recrystallization to offer Compound E-In-4.

General Process for the Preparation of Compound E-In-5 from E-In-4:

E-In-4 was added into a solution TFA in dichloromethane (1% to 100%) or HCl in ether (2N). The reaction mixture was stirred at room temperature for 30 minutes to 18 hours. Concentration under vacuum provided a residue which was purified by silica chromatography or HPLC to afford E-In-5.

General Process for the Preparation of Compound E from E-In-5:

2-Keto acid (1 eq.), E-In-5 (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% $NaHCO_3$ or $NH_4Cl$ aqueous solution. The aqueous layer was extracted with ethyl acetate or methylene chloride. The organic phase combined and dried over anhydrous $MgSO_4$. Concentration in vacuo provided a crude product, which was purified by trituration, or recrystallization, or silica gel column chromatography, or Shimadzu automated preparative HPLC system.

Characterization of E-In and E (Table E):

TABLE E

| Compound No. | Structure | MS (M + H)+ Calcd. | MS (M + H)+ Observ. and Retention Time and NMR |
|---|---|---|---|
| E-In-2 | 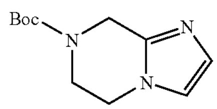 | 224 | 224. $^1$H NMR (DMSO-$d_6$): δ1.46 (s, 9 H), 3.82-3.84 (m, 2 H), 3.97-3.99 (m, 2 H), 4.68 (s, 2 H), 6.85 (s, 1 H), 7.04 (s, 1 H). |
| E-In-3 | 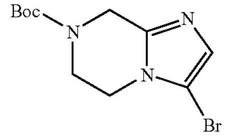 | 302 | 302. $^1$H NMR (DMSO-$d_6$): δ1.46 (s, 9 H), 3.85 (s, 4 H), 4.65 (s, 2 H), 6.99 (s, 1 H). |
| E-In-4 | 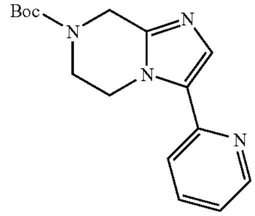 | 301 | 301. $^1$H NMR (DMSO-$d_6$): δ1.47 (s, 9 H), 3.82-3.84 (t, 2 H, J = 5 Hz), 4.51-4.53 (t, 2 H, J = 5 Hz), 4.78 (s, 2 H), 7.11-7.13 (dd, 1 H, J = 7.5 Hz), 7.43 (s, 1 H), 7.51-7.53 (d, 1 H, J = 8 Hz), 7.64-7.68 (dd, 1 H, J = 8.2 Hz), 8.53-8.54 (d, 1 H, J = 5 Hz). |

TABLE E-continued

| Compound No. | Structure | MS (M + H)+ Calcd. | MS (M + H)+ Observ. and Retention Time and NMR |
|---|---|---|---|
| E-In-5 | 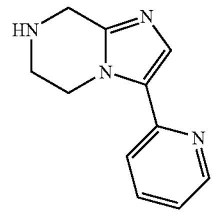 | 201 | 201. |
| E1 | 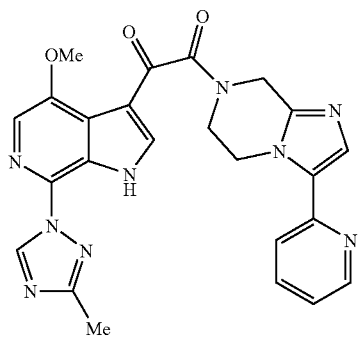 | 484 | 484. $^1$H NMR (DMSO-$d_6$): δ2.52 (s, 3 H), 3.85 & 3.93 (s, 3 H), 3.97-3.99 & 4.16-4.18 (t, 2 H, J = 5 Hz), 4.51-4.53 & 4.67-4.69 (t, 2 H, J = 5 Hz), 5.10 & 4.93 (s, 2 H), 7.37-7.42 (m, 1 H), 7.86-7.95 (m, 3 H), 8.07 (s, 1 H), 8.40-8.41 & 8.32-8.33 (d, 1 H, J = 3 Hz), 8.61-8.61 & 8.68-8.69 (d, 1 H, J = 3 Hz), 9.25 (s, 1 H), 12.51 & 12.46 (s, 1 H). |

Example F

Preparation of Compounds F of Formula 1

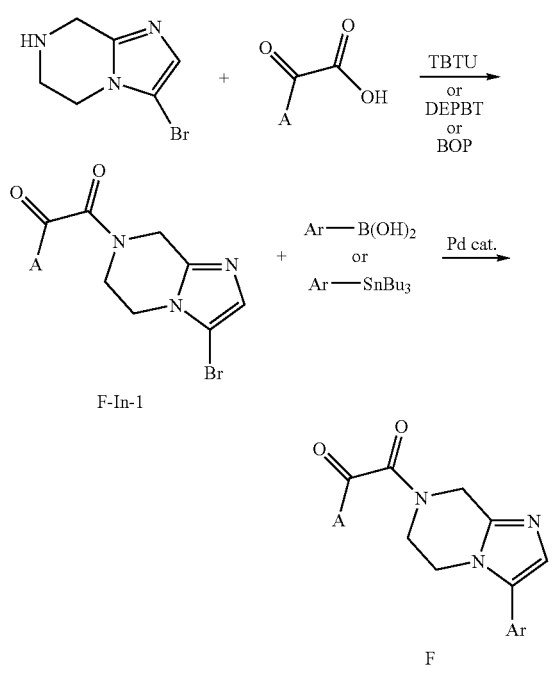

General Process for the Preparation of Compound F-In-1 from 3-Bromo-5,6,7,8-tetrahydroimidazo[1,2-a]pyrazine:

2-Keto acid (1 eq.), 3-bromo-5,6,7,8-tetrahydroimidazo[1,2-a]pyrazine (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% $NaHCO_3$ or $NH_4Cl$ aqueous solution. The aqueous layer was extracted with ethyl acetate or methylene chloride. The organic phase combined and dried over anhydrous $MgSO_4$. Concentration in vacuo provided a crude product, which was purified by trituration, or recrystallization, or silica gel column chromatography, or Shimadzu automated preparative HPLC system.

General Process for the Preparation of Compound F from F-In-1:

F-In-1 (1 eq.), boronic or stannane agent (1-10 eq.) and palladium catalyst (e.g., tetrakis(triphenylphosphine)palladium, bis(diphenylphosphino)ferrocene palladium (II) chloride, bis(triphenylphosphine)palladium(II) chloride) (0.05-1 eq.) with or without base (e.g., $Cs_2CO_3$, $K_2CO_3$, $NaCO_3$, $Na_3PO_4$, $NaH_2PO_4$, $Na_2HPO_4$, $Et_3N$, $iPr_2NEt$, t-BuOK, t-BuONa) were combined in DMF or dioxane, with or without water. The reaction was either heated to 100° C. to 200° C. in sealed tube or carried out in the microwave synthesizer for 20 minutes to 72 hours. The mixture was diluted with MeOH and filtered. The filtration was concentrated and purified by HPLC or recrystallization to offer Compound F.

Characterization of F-In and F (Table F):

TABLE F

| Compound No. | Structure | MS (M + H)+ Calcd. | MS (M + H)+ Observ. and Retention Time and NMR |
|---|---|---|---|
| F-In-1 | 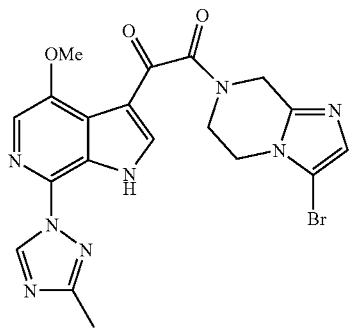 | 485 | 485, Rf = 1.26 min (Method 9). |
| F1 | 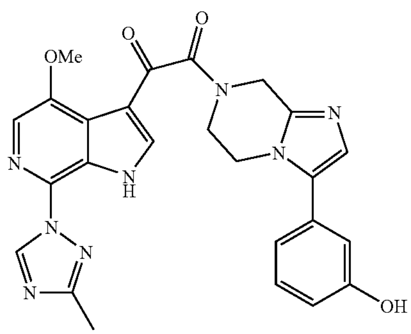 | 499 | 499, Rf = 1.32 min (Method 9). |
| F2 | 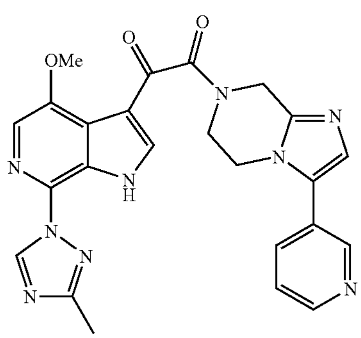 | 484 | 484, Rf = 1.11 min (Method 9). |
| F3 | 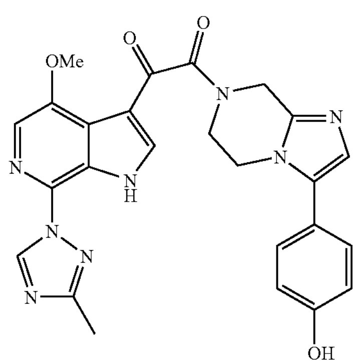 | 499 | 499, Rf = 1.27 min (Method 9). |

TABLE F-continued
| Compound No. | Structure | MS (M + H)+ Calcd. | MS (M + H)+ Observ. and Retention Time and NMR |
|---|---|---|---|
| F4 | 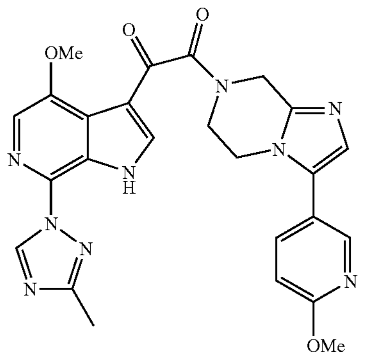 | 514 | 514, Rf = 1.48 min (Method 1). |
| F5 | 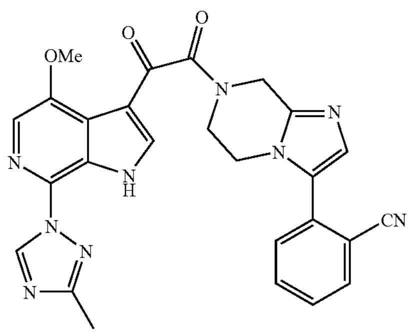 | 508 | 508, Rf = 1.52 min (Method 1). |
| F6 | 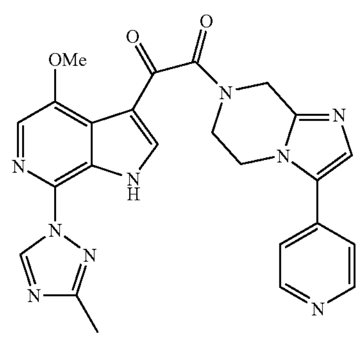 | 484 | 484, Rf = 1.33 min (Method 8). |
Example G
Preparation of Compounds G of Formula 1
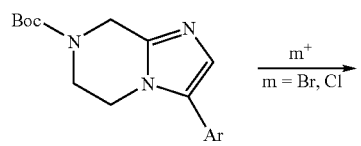
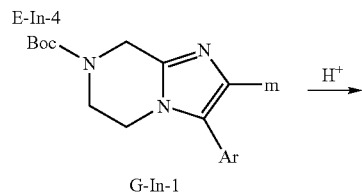
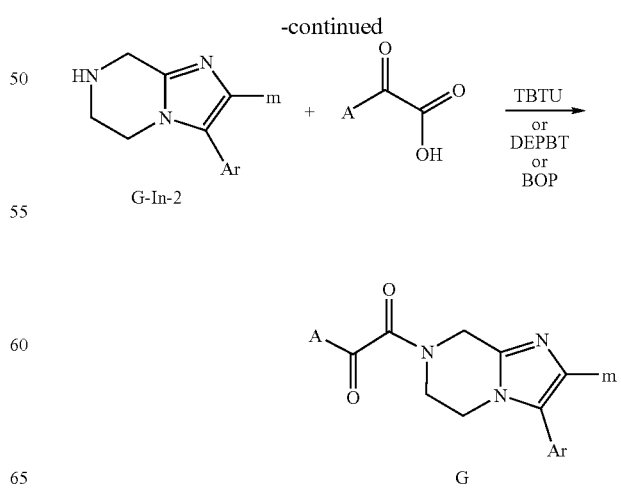

General Process for the Preparation of Compound G-In-1 from E-In-4:

A round bottom flask was charged with acetonitrile, 2-propanol, E-In-4 (1 eq.) and N-chlorosuccinimide or N-bromosuccinimide (1.05 eq.). The reaction was refluxed under nitrogen for 0.25 h. The reaction was diluted with ether, washed with water then brine, dried over $MgSO_4$ and evaporated giving a creamy white powder which was purified by trituration, or recrystallization, or silica gel column chromatography, or Shimadzu automated preparative HPLC system.

General Process for the Preparation of Compound G-In-2 from G-In-1:

G-In-1 was added into a solution TFA in dichloromethane (1% to 100%) or HCl in ether (2N). The reaction mixture was stirred at room temperature for 30 minutes to 18 hours. Concentration under vacuum provided a residue which was purified by silica chromatography or HPLC to afford G-In-2.

General Process for the Preparation of Compound G from G-In-2:

2-Keto acid (1 eq.), G-In-2 (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% $NaHCO_3$ or $NH_4Cl$ aqueous solution. The aqueous layer was extracted with ethyl acetate or methylene chloride. The organic phase combined and dried over anhydrous $MgSO_4$. Concentration in vacuo provided a crude product, which was purified by trituration, or recrystallization, or silica gel column chromatography, or Shimadzu automated preparative HPLC system.

Characterization of G-In and G (Table G):

TABLE G

| Compound No. | Structure | MS (M + H)+ Calcd. | MS (M + H)+ Observ. and Retention Time and NMR |
| --- | --- | --- | --- |
| G-In-1a | 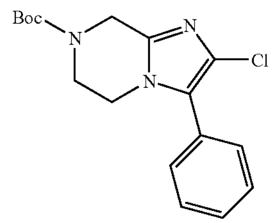 | 334 | 334. $^1$H NMR (DMSO-$d_6$): δ1.49 (s, 9 H), 3.78-3.80 (m, 2 H), 3.86-3.88 (m, 2 H), 4.71 (s, 2 H), 7.38-7.40 (m, 3 H), 7.44-7.47 (m, 2 H). |
| G-In-1b | 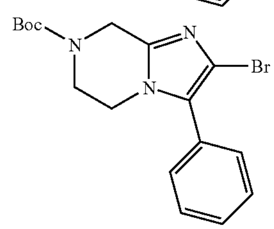 | 378 | $^1$H NMR (DMSO-$d_6$): δ1.48 (s, 9 H), 3.79-3.80 (m, 2 H), 3.86-3.88 (m, 2 H), 4.79 (s, 2 H), 7.38-7.48 (m, 5 H). |
| G1 | 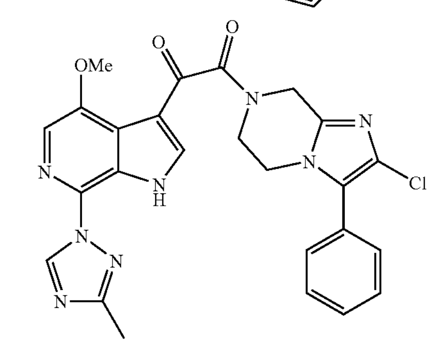 | 517 | 517. $^1$H NMR (DMSO-$d_6$): δ3.17 (s, 3 H), 3.18 (s, 3 H), 3.89-3.91 3.91 (q, 2 H), 4.08-4.11 (q, 2 H), 4.89 & 4.72 (s, 2 H), 7.43-7.55 (m, 5 H), 7.89 & 7.90 (s, 1 H), 8.36 & 8.32 (s, 1 H), 9.25 (s, 1 H), 12.47 (s, 1 H). |
| G2 | 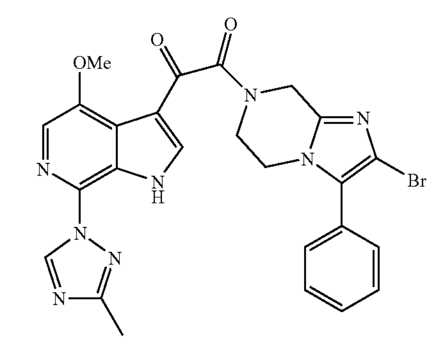 | 561 | 561. $^1$H NMR (DMSO-$d_6$): δ2.52 (s, 3 H), 3.83 & 3.94 (s, 3 H), 3.50-3.90 & 4.05-4.09 (m, 2 H), 4.90 & 4.72 (s, 2 H), 7.42-7.55 (m, 5 H), 7.89 & 7.90 (s, 1 H), 8.36 & 8.32 (s, 1 H), 9.25 (s, 1 H), 12.47 (s, 1 H). |

Example H

Preparation of Compounds H of Formula 1

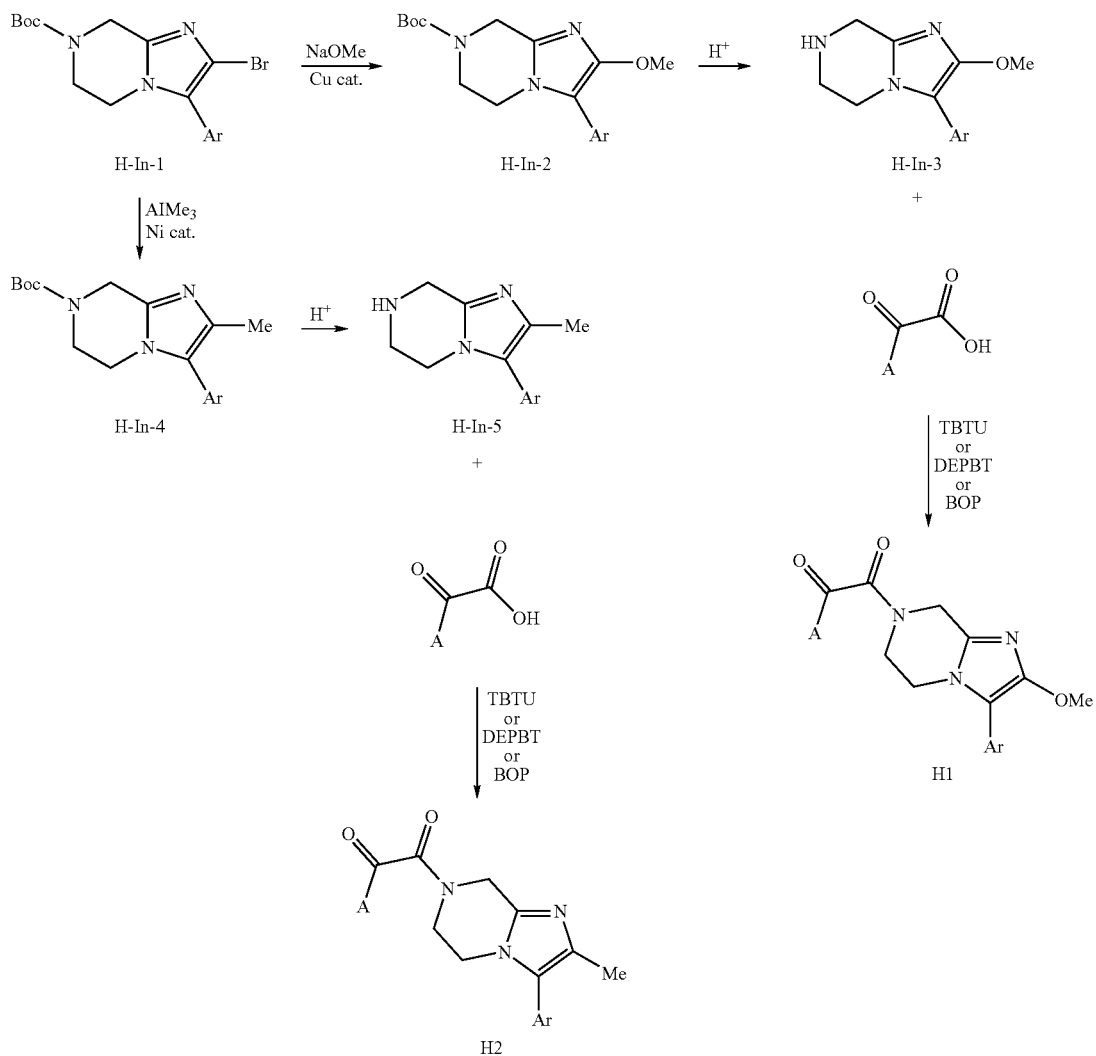

General Process for the Preparation of Compound H-In-2 from H-In-1:

Copper or CuBr or CuCl or CuI was added in the mixture of H-In-1 and sodium methoxide in methanol solution (0.5-4N) in a sealed tube. The reaction mixture was heated to 100-150° C. for 30 minutes to 18 hours. 1N HCl was then added to adjust pH value to 7. The solution was extracted with EtOAc or Ether or dichloromethane. The combined organic layer was washed with brine and then dried over $MgSO_4$. Concentration under vacuum provided a residue which was purified by silica chromatography or HPLC to afford H-In-2.

General Process for the Preparation of Compound H-In-4 from H-In-1:

[1,3-Bis(diphenylphosphino)nickel(II) chloride was added in the mixture of H-In-1 and 2N trimethylalumnium in toluene in a sealed tube. The reaction mixture was heated to 100-150° C. for 30 minutes to 18 hours. 1N HCl was then added to adjust pH value to 7. The solution was extracted with EtOAc or Ether or dichloromethane. The combined organic layer was washed with brine and then dried over $MgSO_4$. Concentration under vacuum provided a residue which was purified by silica chromatography or HPLC to afford H-In-4.

General Process for the Preparation of Compound H-In-3 or H-In-5 from H-In-2 or H-In-4:

H-In-2 or H-In-4 was added into a solution TFA in dichloromethane (1% to 100%) or HCl in ether (2N). The reaction mixture was stirred at room temperature for 30 minutes to 18 hours. Concentration under vacuum provided a residue which was purified by silica chromatography or HPLC to afford H-In-3 or H-In-5.

General Process for the Preparation of Compound H from H-In-3 or H-In-5:

2-Keto acid (1 eq.), H-In-3 or H-In-5 (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% NaHCO₃ or NH₄Cl aqueous solution. The aqueous layer was extracted with ethyl acetate or methylene chloride. The organic phase combined and dried over anhydrous MgSO₄. Concentration in vacuo provided a crude product, which was purified by trituration, or recrystallization, or silica gel column chromatography, or Shimadzu automated preparative HPLC system.

Characterization of H-In and H (Table H):

TABLE H

| Compound No. | Structure | MS (M + H)⁺ Calcd. | MS (M + H)⁺ Observ. and Retention Time and NMR |
|---|---|---|---|
| H-In-2b | 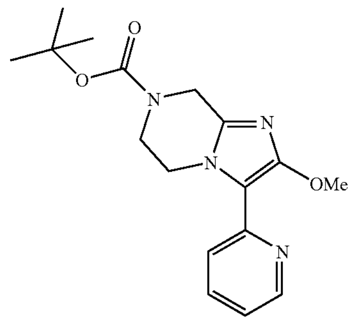 | 331 | 331, Rf = 2.16 min (Method 1). |
| H-In-3a | 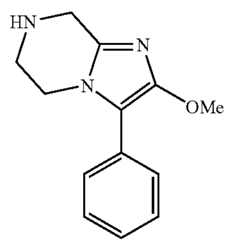 | 230 | 230. |
| H-In-3b | 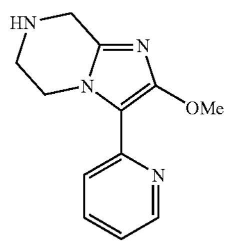 | 231 | 231, Rf = 1.38 min (Method 1). |
| H-In-5a | 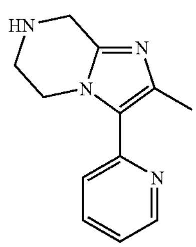 | 215 | 215, Rf = 0.48 min (Method 9). |
| H1a | 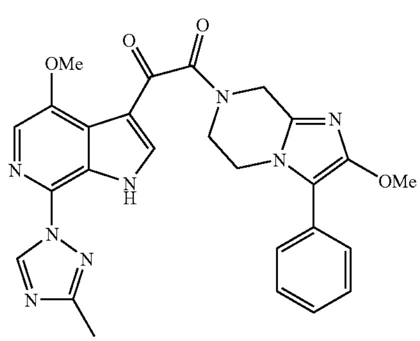 | HRMS: 513.1993 | HRMS: 513.1992. ¹H NMR (DMSO-d₆): δ2.50 (s, 3 H), 3.81 & 3.78 (s, 3 H), 3.86 & 3.92 (s, 3 H), 3.87-3.89 & 4.08-4.10 (t, 2 H, J = 5 Hz), 3.97-3.99 & 4.14-4.16 (t, 2 H, J = 5 Hz), 4.86 & 4.67 (s, 2 H), 7.42-7.55 (m, 5 H), 7.89 & 7.90 (s, 1 H), 8.36 & 8.32 (s, 1 H), 9.25 (s, 1 H), 12.47 (s, 1 H). |

TABLE H-continued
| Compound No. | Structure | MS (M + H)+ Calcd. | MS (M + H)+ Observ. and Retention Time and NMR |
|---|---|---|---|
| H1b | 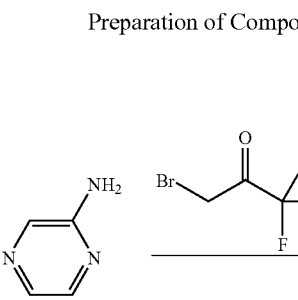 | 514 | 514, Rf = 1.68 min (Method 1). |
| H2 | 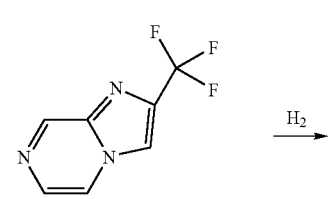 | 498 | 498, Rf = 1.71 min (Method 8). |
Example I
Preparation of Compounds I of Formula 1
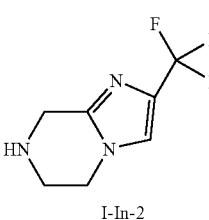
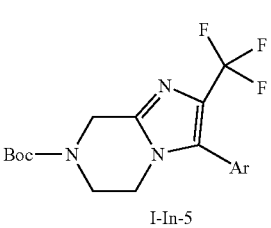
I-In-1
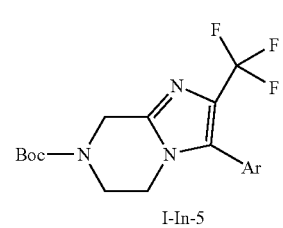
I-In-2
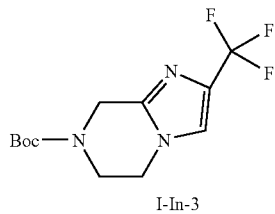
I-In-3
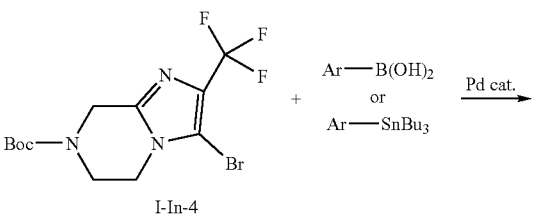
I-In-4
I-In-5

-continued

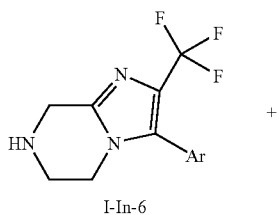

I-In-6

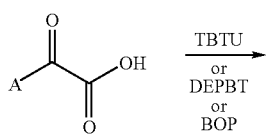

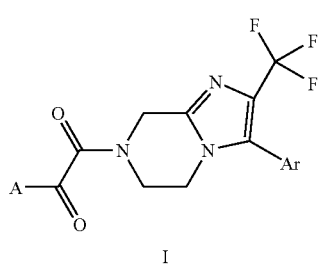

I

Process for the Preparation of Compound I-In-1 from Pyrazin-2-amine:

3-Bromo-1,1,1-trifluoroacetone (1 eq.) was added to a solution of pyrazin-2-amine (1 eq.) in dioxane and the mixture was heated at 40-110° C. for 20 h. The solid formed was collected by filtration and washed twice with EtOAc. This solid was heated in isopropanol at reflux for 3 hours. Reaction mixture cooled to room temperature and partitioned between ethyl acetate and saturated aqueous sodium bicarbonate. The aqueous phase was extracted once more with ethyl acetate. The combined organic layers were washed with brine, dried over sodium sulfate, filtered and concentrated in vacuo to afford a solid containing 2-(trifluoromethyl)imidazo[1,2-a]pyrazine, I-In-1. This material could be purified by trituration, or recrystallization, or silica gel column chromatography, or Shimadzu automated preparative HPLC system, or used as is without further purification.

Process for the Preparation of Compound I-In-2 from I-In-1:

The crude material containing 2-(trifluoromethyl)imidazo[1,2-a]pyrazine, I-In-1 was dissolved in MeOH and was treated with Pd/C and hydrogen at 1atm of pressure. The mixture was stirred at room temperature for 2 h. Reaction transferred to a Parr shaker reactor and kept under 50 psi for 20 h. Solution filtered through CELITE® to remove catalyst and concentrated in vacuo. Residue containing 2-(trifluorom-ethyl)-5,6,7,8-tetrahydroimidazo[1,2-a]pyrazine, I-In-2, could be purified by trituration, or recrystallization, or silica gel column chromatography, or Shimadzu automated preparative HPLC system, or used as is without further purification.

Process for the Preparation of Compound I-In-3 from I-In-2:

The solution of 2-(trifluoromethyl)-5,6,7,8-tetrahydroimidazo[1,2-a]pyrazine (1 eq.), Hunig's Base (1-20 eq.) and $BOC_2O$ (1-5 eq.) was stirred in $CH_2Cl_2$ at room temperature for 1-20 h. The volume was reduced to half in vacuo and then the solution was partitioned between ethyl acetate and 0.5N HCl. Aqueous phase was extracted twice with EtOAc. The combined organic phases were dried over sodium sulfate, filtered and concentrated in vacuo. The residue was purified on silica gel to afford I-In-3.

Process for the Preparation of Compound I-In-4 from I-In-3:

I-In-3 (1 eq.) in chloroform was cooled to 0° C. and bromine (1 eq.) was added slowly. The reaction was stirred at this temperature for 30 min and then placed at room temperature for 1.5 h. Bromine (1 eq.) was added and the stirring continued for 2 h. The reaction was quenched with aq. sat. $NaHCO_3$, extracted with AcOEt, dried over $Na_2SO_4$, and purified on silica gel (hexanes-10% EtOAc/Hex) to afford I-In-4.

General Process for the Preparation of Compound I-In-5 from I-In-4:

I-In-4 (1 eq.), boronic or stannane agent (1-10 eq.) and palladium catalyst (e.g., tetrakis(triphenylphosphine)palladium, bis(diphenylphosphino)ferrocene palladium (II) chloride, bis(triphenylphosphine)palladium(II) chloride) (0.05-1 eq.) with or without base (e.g., $Cs_2CO_3$, $K_2CO_3$, $NaCO_3$, $Na_3PO_4$, $NaH_2PO_4$, $Na_2HPO_4$, $Et_3N$, $iPr_2NEt$, t-BuOK, t-BuONa) were combined in DMF or dioxane, with or without water. The reaction was either heated to 100° C. to 200° C. in sealed tube or carried out in the microwave synthesizer for 20 minutes to 72 hours. The mixture was diluted with MeOH and filtered. The filtration was concentrated and purified by HPLC or recrystallization to offer I-In-5.

General Process for the Preparation of Compound I-In-6 from I-In-5:

I-In-5 was added into a solution TFA in dichloromethane (1% to 100%) or HCl in ether (2 N). The reaction mixture was stirred at room temperature for 30 minutes to 18 hours. Concentration under vacuum provided a residue which was purified by silica chromatography or HPLC to afford I-in-6.

General Process for the Preparation of Compound I from I-In-6:

2-Keto acid (1 eq.), I-In-6 (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% $NaHCO_3$ or $NH_4Cl$ aqueous solution. The aqueous layer was extracted with ethyl acetate or methylene chloride. The organic phase combined and dried over anhydrous $MgSO_4$. Concentration in vacuo provided a crude product, which was purified by trituration, or recrystallization, or silica gel column chromatography, or Shimadzu automated preparative HPLC system, to afford Compound I.

Characterization of I-In and I (Table I):

TABLE I

| Compound No. | Structure | MS (M + H)+ Calcd. | MS (M + H)+ Observ. and Retention Time and NMR |
| --- | --- | --- | --- |
| I-In-1 | 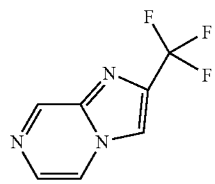 | 188 | 188, Rf = 1.19 min (Method 2). ¹H NMR (500 MHz, CDCl₃) δppm 9.21 (s, 1 H), 8.11 (s, 1 H), 7.94-8.08 (m, 2 H). |
| I-In-2 | 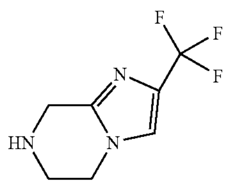 | 192 | 192, Rf = 0.24 min (Method 2). |
| I-In-3 | 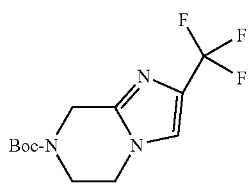 | 292 | 292, Rf = 2.99 min. (Method 2). ¹H NMR (500 MHz, CDCl₃): δppm 7.20 (s, 1 H), 4.71 (s, 2 H), 3.97-4.07 (m, 2 H), 3.78-3.93 (m, 2 H), 1.47 (s, 9 H). |
| I-In-4 | 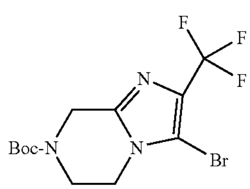 | 370 | ¹H NMR (500 MHz, CDCl₃): δppm 4.70 (s, 2 H), 3.91-3.90 (m, 4 H), 1.49 (s, 9 H). |
| I-In-5a | 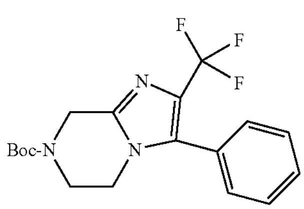 | 368 | 368, Rf = 2.35 min. (Method 2). |
| I-In-5b | 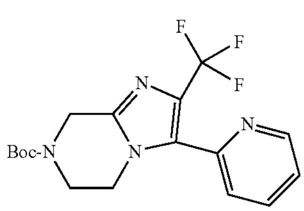 | 369 | 369, Rf = 2.10 min (Method 3). |
| I-In-6a | 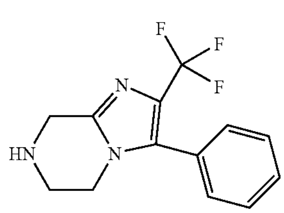 | 268 | 268, Rf = 1.67 min. (Method 2). |

TABLE I-continued

| Compound No. | Structure | MS (M + H)+ Calcd. | MS (M + H)+ Observ. and Retention Time and NMR |
|---|---|---|---|
| I-In-6b | 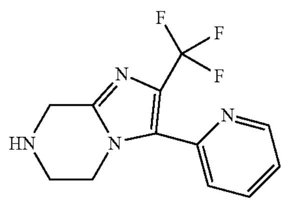 | 269 | 269, Rf = 1.39 min (Method 3). |
| I1 | 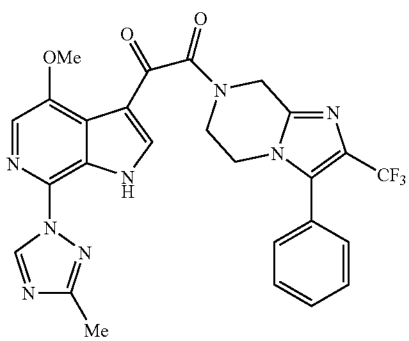 | 551 | 551, Rf = 2.77 min (Method 2). $^1$H NMR (500 MHz, DMSO-d$_6$): δppm 12.45-12.52 (m, 1 H), 9.22-9.27 (m, 1 H), 8.30-8.38 (m, 1 H), 7.87-7.92 (m, 1 H), 7.41-7.58 (m, 5 H), 4.74-4.98 (m, 2 H), 3.74-4.14 (m, 10 H). |
| I2 | 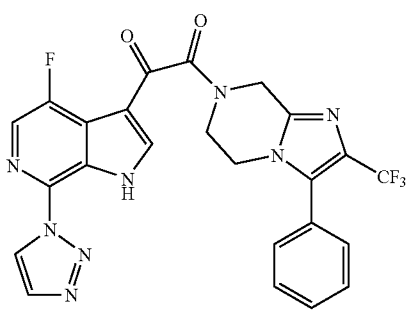 | 525 | 525, Rf = 2.00 min (Method 1). $^1$H NMR (500 MHz, DMSO-d$_6$): δppm 13.07-13.18 (m, 1 H), 8.99-9.06 (m, 1 H), 8.42-8.61 (m, 1 H), 8.31-8.37 (m, 1 H), 8.13 (s, 1 H), 7.41-7.59 (m, 5 H), 4.79-4.98 (m, 2 H), 3.76-4.13 (m, 4 H). |
| I3 | 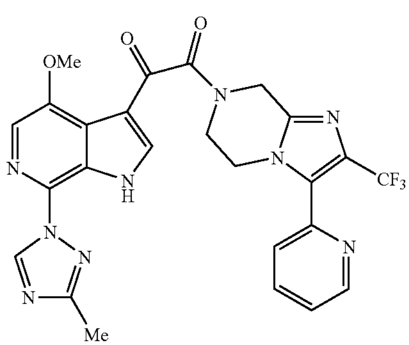 | 552 | 552, Rf = 1.23 min (Method 4). $^1$H NMR (500 MHz, DMSO-d$_6$): δppm 2.51 (s, 3 H), 3.69-4.33 (m, 7 H), 4.71-5.16 (m, 2 H), 7.43-7.71 (m, 2 H), 7.81-7.95 (m, 1 H) 7.92-8.15 (m, 1 H) 8.19-8.48 (m, 1 H), 8.70 (d, J = 4.27 Hz, 1 H), 9.24 (s, 1 H), 12.49 (s, 1 H). |

Example J

Preparation of Compounds J of Formula 1

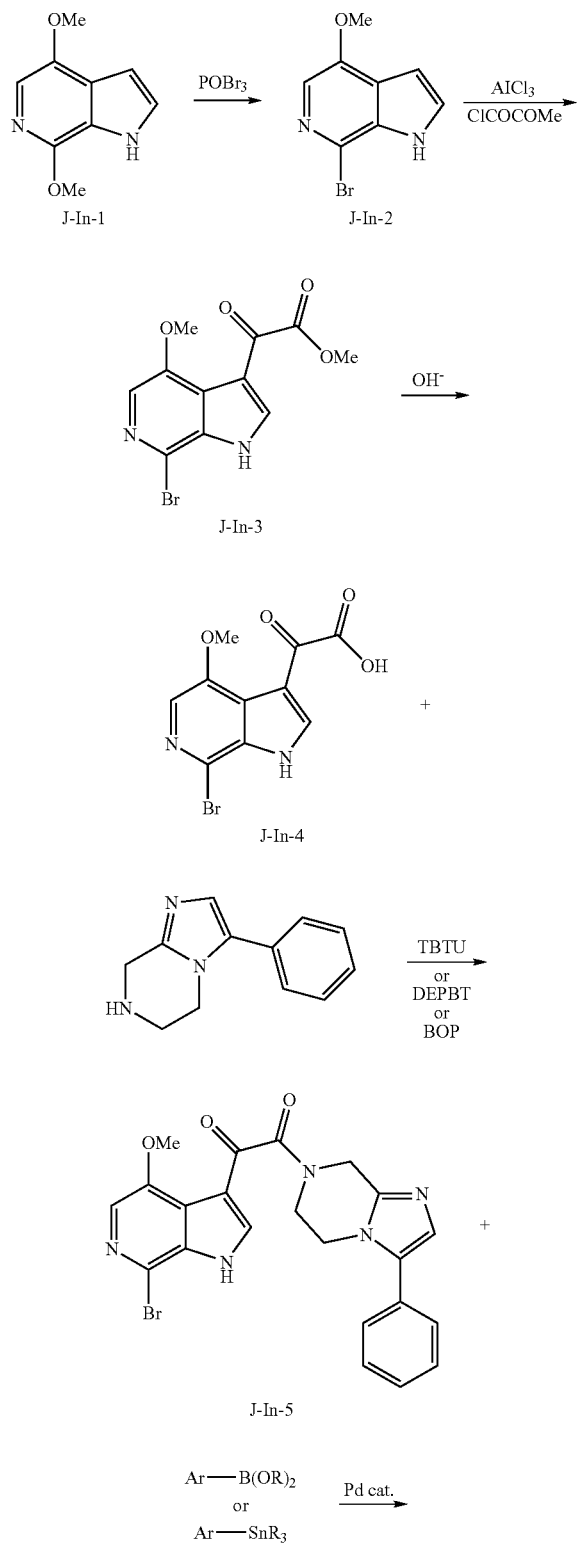

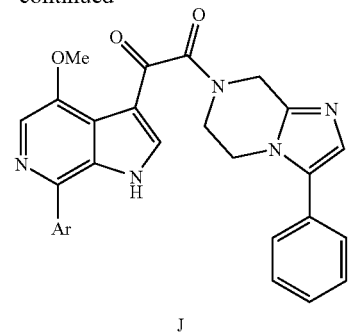

Process for the Preparation of Compound J-In-2 from J-In-1:

To a stirred solution of 4,7-dimethoxy azaindole (1 eq.) in anisole was added phosphorus oxybromide (1 eq.) portion wise and the reaction mixture was slowly heated to 120° C. Reaction mixture was allowed to stir at 120° C. for about 18 h. Then, the reaction mixture was cooled to 10° C. and slowly quenched with ice-water mixture. The resulting mixture was neutralized with saturated sodium bicarbonate solution and then extracted with ethyl acetate. The combined organic layer was washed with brine, dried over sodium sulfate, filtered and concentrated. The crude product was purified by column chromatography using 60-120 silica gel and 15% ethyl acetate in hexane as eluent to afford J-In-2.

Process for the Preparation of Compound J-In-3 from J-In-2:

To a stirred solution of aluminum chloride (4 eq.) in dry dichloromethane under nitrogen atmosphere was added J-In-2 (1 eq.) portion wise and the reaction mixture was stirred at room temperature for 2 h. In a separate flask, to a stirred solution of aluminum chloride (6 eq.) in dry dichloromethane under nitrogen atmosphere was added methoxy oxalylchloride (3 eq.) drop wise. The reaction mixture was allowed to stir at room temperature for 2 hrs. Then this reaction mixture was added slowly to the above reaction mixture for about 30 min and stirred for 16 h at room temperature. The reaction mixture was quenched with saturated ammonium acetate solution to pH-7. The resulting mixture was extracted with ethyl acetate. The combined organic layer was washed with brine, dried over sodium sulfate, filtered and concentrated. The crude product was purified by column chromatography using 60-120 silica gel and 25% ethyl acetate in hexane as eluent to afford J-In-3.

General Process for the Preparation of Compound J-In-4 from J-In-3:

J-In-3 (1 eq.) was dissolved in THF/water or acetone/water mixture (1:1), LiOH or NaOH or $K_2CO_3$ (2-10 eq.) and the reaction was stirred for 20 h at room temperature. The volatiles were removed under reduced pressure and acidified the mixture using dilute HCl (pH-6). The resulting solid (J-In-4) was filtered, dried and used for the next step without further purification.

General Process for the Preparation of Compound J-In-5 from J-In-4:

2-Keto acid (1 eq.), J-In-4 (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% $NaHCO_3$ or $NH_4Cl$ aqueous solution. The aqueous layer was extracted with ethyl acetate or methylene chloride. The organic phase combined and dried over anhydrous $MgSO_4$.

Concentration in vacuo provided a crude product, which was purified by trituration, or recrystallization, or silica gel column chromatography, or Shimadzu automated preparative HPLC system, to afford J-In-5.

General Process for the Preparation of Compound J from J-In-5:

J-In-5 (1 eq.), boronic or stannane agent (1-10 eq.) and palladium catalyst (e.g., tetrakis(triphenylphosphine)palladium, bis(diphenylphosphino)ferrocene palladium (II) chloride, bis(triphenylphosphine)palladium(II) chloride) (0.05-1 eq.) with or without base (e.g., $Cs_2CO_3$, $K_2CO_3$, $NaCO_3$, $Na_3PO_4$, $NaH_2PO_4$, $Na_2HPO_4$, $Et_3N$, $iPr_2NEt$, t-BuOK, t-BuONa) were combined in DMF or dioxane, with or without water. The reaction was either heated to 100° C. to 200° C. in sealed tube or carried out in the microwave synthesizer for 20 minutes to 72 hours. The mixture was diluted with MeOH and filtered. The filtration was concentrated and purified by HPLC or recrystallization to offer Compound J.

Characterization of J-In and J (Table J):

TABLE J

| Compound No. | Structure | MS (M + H)+ Calcd. | MS (M + H)+ Observ. and Retention Time and NMR |
|---|---|---|---|
| J-In-2 | 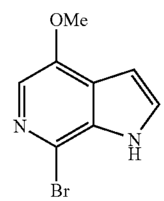 | 227 | 227. |
| J-In-3 | 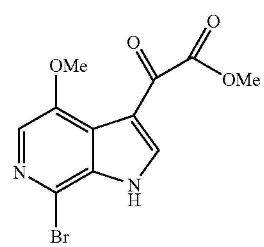 | 313 | 313. |
| J-In-4 | 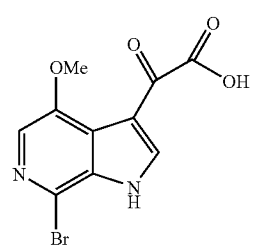 | 299 | 299. |
| J-In-5 | 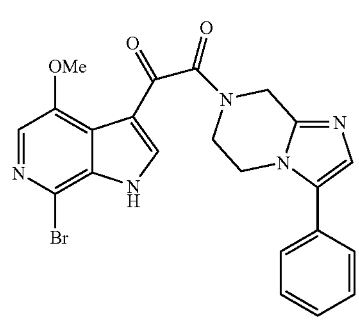 | 480 | 480. |

TABLE J-continued

| Compound No. | Structure | MS (M + H)+ Calcd. | MS (M + H)+ Observ. and Retention Time and NMR |
|---|---|---|---|
| J1 | 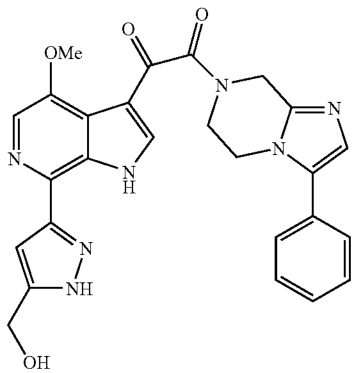 | 498 | 498, Rf = 1.72 min (Method 2). $^1$H NMR (500 MHz, MeOD): δppm 4.08-4.22 (m, 5 H), 4.30-4.46 (m, 2 H), 4.81 (s, 2 H), 5.23-5.40 (m, 2 H), 7.19 (s, 1 H), 7.53-7.67 (m, 5 H), 7.70-7.80 (m, 1 H), 7.99-8.07 (m, 1 H), 8.68-8.79 (m, 1 H). |
| J2 | 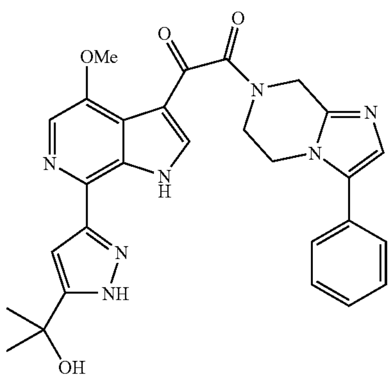 | 526 | 526, Rf = 1.92 min (Method 2). $^1$H NMR (500 MHz, MeOD): δppm 1.69 (s, 6 H), 4.15 (m, 5 H), 4.29-4.48 (m, 2 H), 5.27-5.39 (m, 2 H), 7.14 (s, 1 H), 7.54-7.69 (m, 5 H), 7.71-7.83 (m, 1 H), 8.04 (s, 1 H), 8.72-8.82 (m, 1 H). |

Example K

Preparation of Compounds K of Formula 1

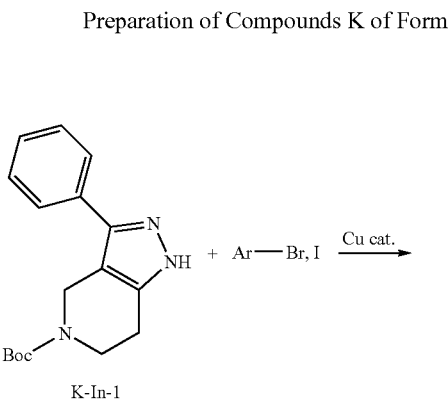

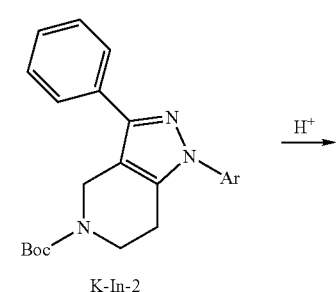

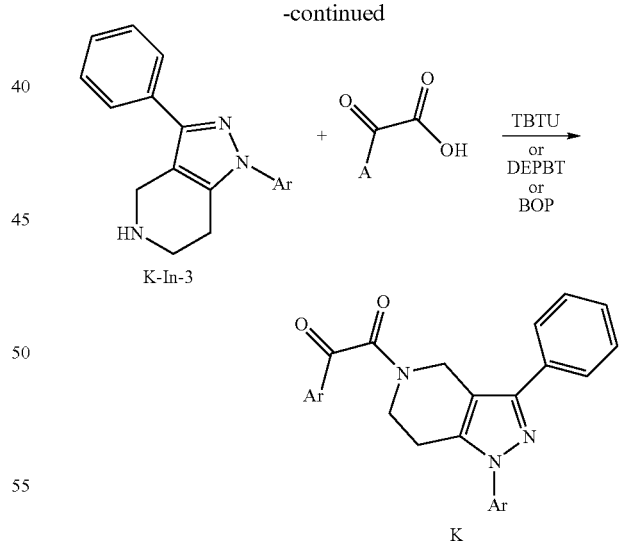

General Process for the Preparation of Compound K-In-2 from K-In-1:

K-In-1 (1 eq.), base selected from $Cs_2CO_3$, $K_2CO_3$, $NaCO_3$, $Na_3PO_4$, $NaH_2PO_4$, $Na_2HPO_4$, $Et_3N$, $iPr_2NEt$, t-BuOK and t-BuONa (1-10 eq.), copper agent selected from Cu, CuCl, CuBr and CuI (0.01-2 eq.), (1R,2R)-diaminomethylcyclohexane (0.02-4 eq.), and aryl bromide or aryl iodide (1-5 eq.) were combined in a sealable flask. The mixture was diluted with 1,4-dioxane. The flask was flushed with $N_2$, sealed, and heated to 100° C. for 2-24 h. The mixture was cooled to room temperature and was filtered through a pad of CELITE® to remove solids. The organic solution was concentrated under reduced pressure, and the residue was purified by silica chromatography or HPLC to afford K-In-2.

General Process for the Preparation of Compound K-In-3 from K-In-2:

K-In-2 was added into a solution TFA in dichloromethane (1% to 100%) or HCl in ether (2N). The reaction mixture was stirred at room temperature for 30 minutes to 18 hours. Concentration under vacuum provided a residue which was purified by silica chromatography or HPLC to afford K-In-3.

General Process for the Preparation of Compound K from K-In-3:

2-Keto acid (1 eq.), K-In-3 (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% $NaHCO_3$ or $NH_4Cl$ aqueous solution. The aqueous layer was extracted with ethyl acetate or methylene chloride. The organic phase combined and dried over anhydrous $MgSO_4$. Concentration in vacuo provided a crude product, which was purified by trituration, or recrystallization, or silica gel column chromatography, or Shimadzu automated preparative HPLC system, to afford Compound K.

Characterization of K-In and K (Table K):

TABLE K

| Compound No. | Structure | MS (M + H)⁺ Calcd. | MS (M + H)⁺ Observ. and Retention Time and NMR |
|---|---|---|---|
| K-In-2 | 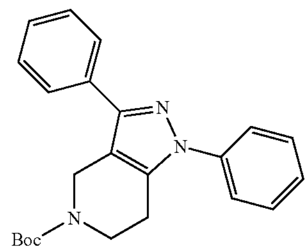 | 376 | 376, Rf = 3.405 min (Method 2). $^1$H NMR (500 MHz, $CDCl_3$): δppm 7.77 (d, J = 7.02 Hz, 2 H), 7.26-7.61 (m, 8 H), 4.75 (br. s., 2 H), 3.74 (br. s., 2 H), 2.85-2.94 (m, 2 H), 1.48-1.55 (m, 9 H). |
| K-In-3 | 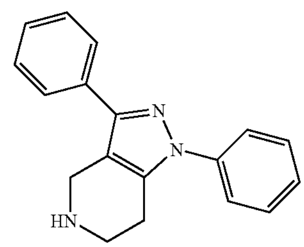 | 276 | 276, Rf = 2.06 min (Method 2). $^1$H (500 MHz, MeOD): δppm 7.40-7.74 (m, 10 H), 4.54 (s, 2 H), 3.60 (t, J = 6.10 Hz, 2 H), 3.20 (t, J = 6.10 Hz, 2 H). |
| K1 | 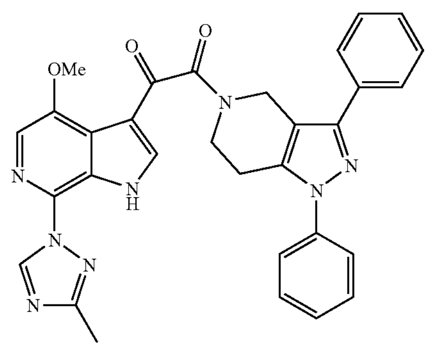 | 559 | 559, Rf = 2.09 min (Method 1). $^1$H NMR (500 MHz, DMSO-$d_6$): δppm 12.44 (br. s., 1 H), 9.21-9.28 (m, 1 H), 8.19-8.35 (m, 1 H), 7.27-7.98 (m, 11 H), 4.73-4.98 (m, 2 H), 3.70-4.04 (m, 5 H), 2.91-3.12 (m, 2 H), 2.44-2.55 (m, 3 H). |

Example L

Preparation of Compounds L of Formula 1

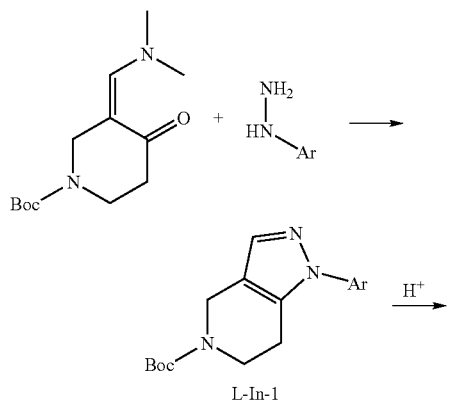

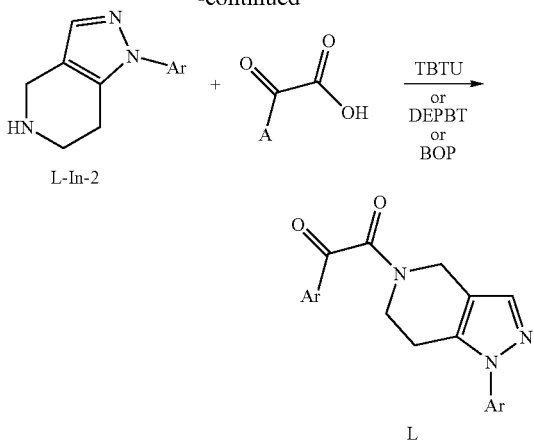

General Process for the Preparation of Compound L-In-1 from tert-Butyl 3-((dimethylamino)methylene)-4-oxopiperidine-1-carboxylate:

tert-Butyl 3-((dimethylamino)methylene)-4-oxopiperidine-1-carboxylate (1 eq.) and hydrazine (1-2eq.) were mixed in ethanol. The reaction mixture was heated at 115° C. for 16 h. After removal of the solvents under vacuum, the residue was purified using silica gel column chromatography or Shimadzu automated preparative HPLC system, to afford L-In-1.

General Process for the Preparation of Compound L-In-2 from L-In-1:

L-In-1 was added to a solution of TFA in dichloromethane (1% to 100%) or HCl in ether (2N). The reaction mixture was stirred at room temperature for 30 minutes to 18 hours. Concentration under vacuum provided a residue which was purified by silica chromatography or HPLC to afford L-In-2.

General Process for the Preparation of Compound L from L-In-2:

2-Keto acid (1 eq.), L-In-2 (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% $NaHCO_3$ or $NH_4Cl$ aqueous solution. The aqueous layer was extracted with ethyl acetate or methylene chloride. The organic phase combined and dried over anhydrous $MgSO_4$. Concentration in vacuo provided a crude product, which was purified by trituration, or recrystallization, or silica gel column chromatography, or Shimadzu automated preparative HPLC system, to afford Compound L.

Characterization of L-In and L (Table L):

TABLE L

| Compound No. | Structure | MS (M + H)+ Calcd. | MS (M + H)+ Observ. and Retention Time and NMR |
|---|---|---|---|
| L-In-1a | 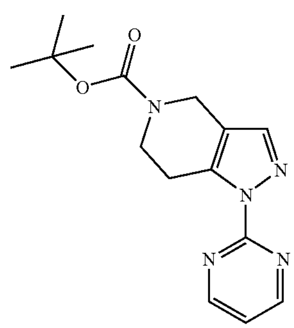 | 302 | 302, Rf = 1.72 min (Method 4). |
| L-In-1b | 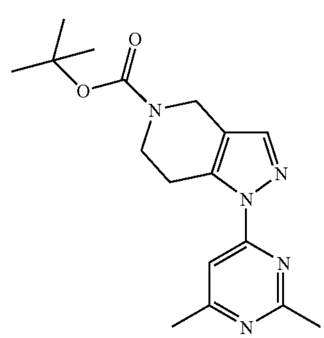 | 330 | 330, Rf = 1.72 min (Method 4). |

TABLE L-continued

| Compound No. | Structure | MS (M + H)+ Calcd. | MS (M + H)+ Observ. and Retention Time and NMR |
|---|---|---|---|
| L-In-1c | 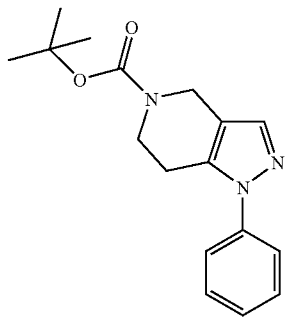 | 300 | 300, Rf = 1.91 min (Method 4). |
| L-In-1d | 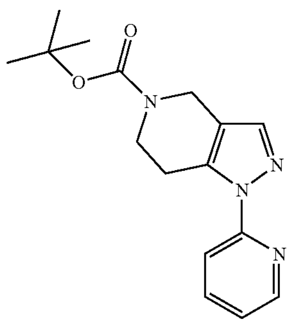 | 301 | 301, Rf = 1.94 min (Method 4). |
| L-In-1e | 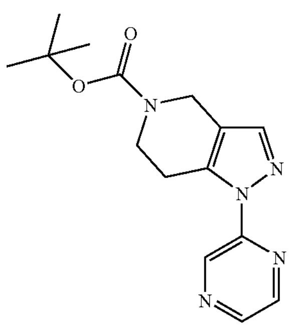 | 302 | 302, Rf = 1.86 min (Method 4). |
| L-In-2a | 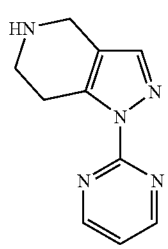 | 202 | 202, Rf = 0.26 min (Method 10). |
| L-In-2b | 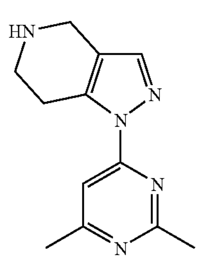 | 230 | 230, Rf = 0.46 min (Method 11). |

TABLE L-continued

| Compound No. | Structure | MS (M + H)+ Calcd. | MS (M + H)+ Observ. and Retention Time and NMR |
|---|---|---|---|
| L-In-2c | 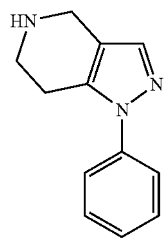 | 200 | 200, Rf = 1.01 min (Method 12). |
| L-In-2d | 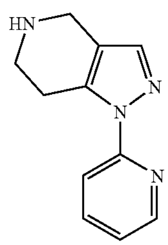 | 201 | 201, Rf = 0.65 min (Method 4). |
| L-In-2e | 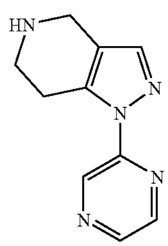 | 202 | 202, Rf = 0.35 min (Method 10). |
| L1 | 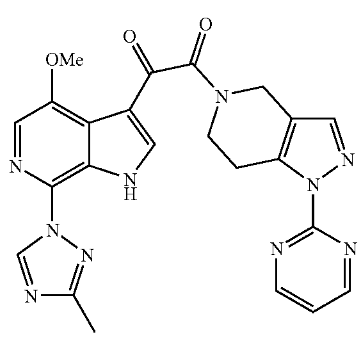 | 485 | 485, Rf = 1.48 min (Method 5). $^1$H NMR (500 MHz, DMSO-$d_6$): δppm 12.36-12.44 (m, 1 H), 9.20-9.25 (m, 1 H), 8.80-8.92 (m, 2 H), 8.17-8.30 (m, 1 H), 7.40-7.88 (m, 3 H), 4.46-4.77 (m, 2 H), 3.78-3.97 (m, 5 H), 3.13-3.33 (m, 2 H), 2.46 (s, 3 H). |
| L2 | 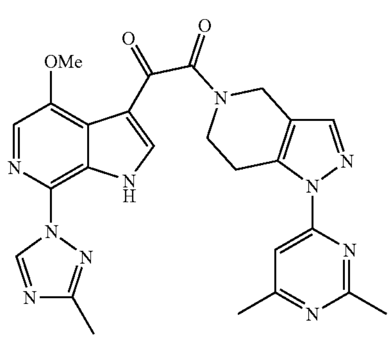 | 513 | 513, Rf = 1.49 min (Method 5). $^1$H NMR (500 MHz, DMSO-$d_6$): δppm 12.30-12.49 (m, 1 H), 9.16-9.30 (m, 1 H), 8.12-8.32 (m, 1 H), 7.55-7.88 (m, 3 H), 4.45-4.75 (m, 2 H), 3.66-3.99 (m, 6 H), 3.25-3.44 (m, 3 H), 2.50-2.61 (m, 3 H), 2.46-2.48 (m, 4 H). |

TABLE L-continued
| Compound No. | Structure | MS (M + H)+ Calcd. | MS (M + H)+ Observ. and Retention Time and NMR |
|---|---|---|---|
| L3 | 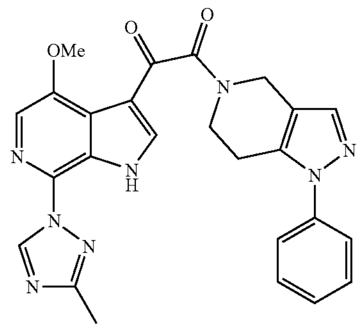 | 483 | 483, Rf = 1.69 min (Method 5). ¹H NMR (500 MHz, DMSO-d₆): δppm 12.35-12.48 (m, 1 H), 9.18-9.26 (m, 1 H), 8.19-8.33 (m, 1 H), 7.82-7.90 (m, 1 H), 7.60-7.72 (m, 1 H), 7.46-7.59 (m, 4 H), 7.34-7.40 (m, 1 H), 4.48-4.74 (m, 2 H), 3.65-3.96 (m, 5 H), 2.85-3.04 (m, 2 H), 2.47-2.48 (m, 3 H). |
| L4 | 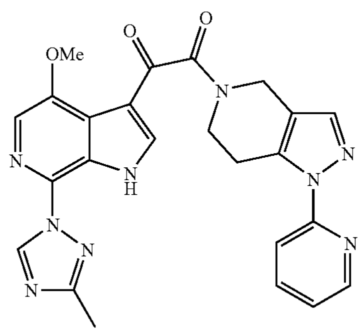 | 484 | 484, Rf = 1.68 min (Method 5). ¹H NMR (500 MHz, DMSO-d₆): δppm 12.33-12.44 (m, 1 H), 9.18-9.27 (m, 1 H), 8.36-8.50 (m, 1 H), 8.17-8.29 (m, 1 H), 7.93-8.00 (m, 1 H), 7.81-7.90 (m, 2 H), 7.58-7.77 (m, 1 H), 7.28-7.36 (m, J = 6.87, 5.34 Hz, 1 H), 4.47-4.73 (m, 2 H), 3.68-3.97 (m, 5 H), 3.19-3.38 (m, 2 H), 2.46-2.48 (m, 3 H). |
| L5 | 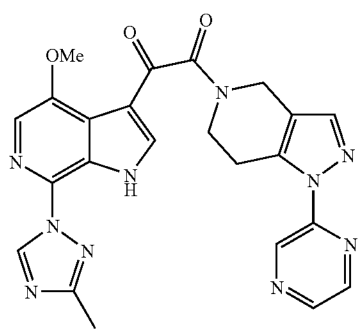 | 485 | 485, Rf = 1.58 min (Method 5). ¹H NMR (500 MHz, DMSO-d₆): δppm 12.34-12.44 (m, 1 H), 9.15-9.26 (m, 2 H), 8.44-8.61 (m, 2 H), 8.17-8.29 (m, 1 H), 7.68-7.89 (m, 2 H), 4.48-4.77 (m, 2 H), 3.68-3.99 (m, 5 H), 2.70-3.20 (m, 2 H), 2.46-2.48 (m, 3 H). |
Example M
Preparation of Compounds M of Formula 1
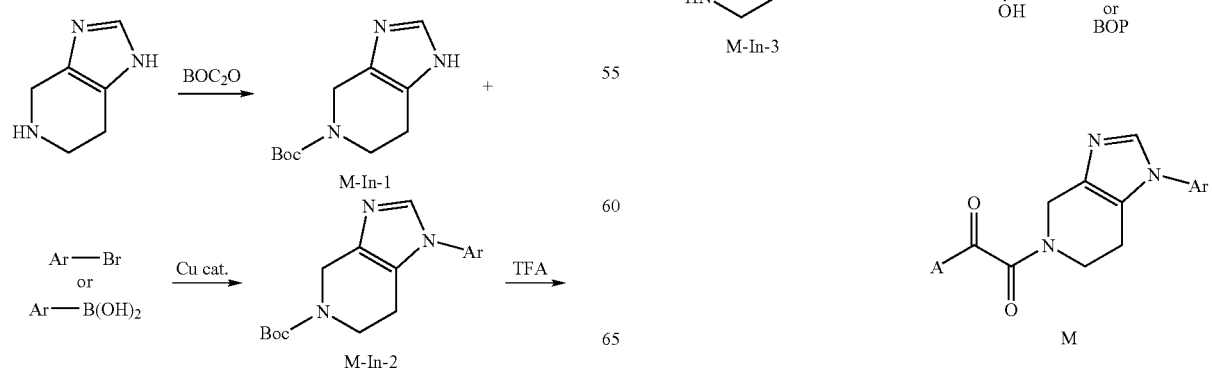

General Process for the Preparation of Compound M-In-1 from 4,5,6,7-Tetrahydro-1H-imidazo[4,5-c]pyridine:

4,5,6,7-Tetrahydro-1H-imidazo[4,5-c]pyridine (1 eq.) was dissolved in $CH_2Cl_2$ and treated with TEA (2-10 eq.), BOC-Anhydride (2 eq.) and a catalytic amount of DMAP (0.01-1 eq.) and the mixture was stirred at room temperature for 1-7 days. The reaction mixture was quenched with 1N HCl, followed by extraction with $CH_2Cl_2$. The organic phase was dried over $Na_2SO_4$, filtered and concentrated. The crude product containing both diboc-regioisomers drawn above was dissolved in MeOH and treated with ammonia in MeOH and the mixture was heated at 60° C. for 2-8 h. Removal of solvents under vacuum afforded M-In-1 which was purified by trituration, or recrystallization, or silica gel column chromatography, or Shimadzu automated preparative HPLC system. The crude M-In-1 could be used in the further reaction without any purification.

General Process for the Preparation of Compound M-In-2 from M-In-1:

M-In-1 (1 eq.), boronic acid (1-5 eq.), pyridine (0.01-5 eq.), $Cu(OAc)_2$ (0.01-2 eq.) and molecular sieves (4 A) were stirred in $CH_2Cl_2$ at room temperature with open air for 1-10 days. The reaction mixture was filtered to remove solids and the filtrate was concentrated under vacuum provided a residue which was purified by HPLC to afford M-In-2.

General Process for the Preparation of Compound M-In-3 from M-In-2:

M-In-2 was added into a solution TFA in dichloromethane (1% to 100%) or HCl in ether (2N). The reaction mixture was stirred at room temperature for 30 minutes to 18 hours. Concentration under vacuum provided a residue which was purified by silica chromatography or HPLC to afford M-In-3.

General Process for the Preparation of Compound M from M-In-3:

2-Keto acid (1 eq.), M-In-3 (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% $NaHCO_3$ or $NH_4Cl$ aqueous solution. The aqueous layer was extracted with ethyl acetate or methylene chloride. The organic phase combined and dried over anhydrous $MgSO_4$. Concentration in vacuo provided a crude product, which was purified by trituration, or recrystallization, or silica gel column chromatography, or Shimadzu automated preparative HPLC system, to afford Compound M.

Characterization of M-In and M (Table M):

TABLE M

| Compound No. | Structure | MS (M + H)+ Calcd. | MS (M + H)+ Observ. and Retention Time and NMR |
|---|---|---|---|
| M-In-1 | 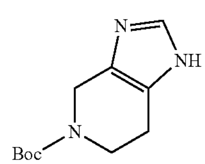 | 224 | 224, Rf = 0.96 min (Method 1). $^1$H NMR (500 MHz, CDCl$_3$): δppm 7.57 (s, 1 H), 4.43 (brs, 2 H), 3.66 (brs, 2 H), 2.64 (brs, 2 H), 1.42 (s, 9 H). |
| M-In-2a | 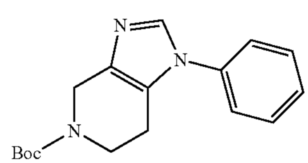 | 300 | 300, Rf = 1.41 min (Method 1). $^1$H NMR (500 MHz, CDCl$_3$): δppm 8.68 (br. s., 1 H), 7.32-7.73 (m, 6 H), 4.66 (br. s., 2 H), 3.76 (br. s., 2 H), 2.60-2.80 (m, 2 H), 1.37-1.60 (m, 12 H). |
| M-In-2b | 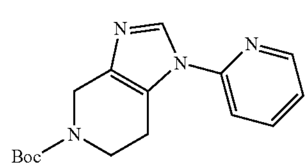 | 301 | $^1$H NMR (500 MHz, CDCl$_3$): δ9.04 (s, 1 H), 8.54 (m, 1 H), 7.95 (m, 1 H), 7.57 (m, 1 H), 7.44 (m, 1 H), 4.62 (s, 2 H). 3.74 (m, 2 H), 3.00 (m, 2 H), 1.45 (s, 9 H). |
| M-In-3a | 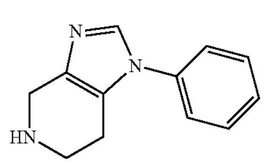 | 200 | 200, Rf = 0.77 min (Method 1). |

TABLE M-continued

| Compound No. | Structure | MS (M + H)+ Calcd. | MS (M + H)+ Observ. and Retention Time and NMR |
|---|---|---|---|
| M1 | 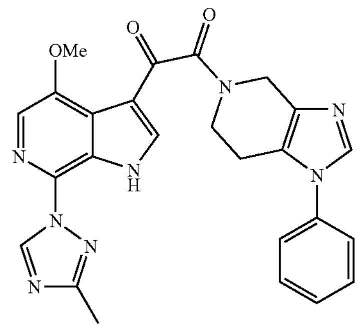 | 483 | 483, Rf = 1.10 min (Method 1). ¹H NMR (500 MHz, MeOD): δppm 9.24 (s, 1 H), 8.82-9.05 (m, 1 H), 8.29-8.42 (m, 1 H), 7.88 (s, 1 H), 7.52-7.74 (m, 5 H), 3-5.02 (m, 2 H), 3.95-4.07 (m, 3 H), 3.83-4.23 (m, 2 H), 2.78-2.99 (m, 2 H), 2.57 (s, 3 H). |
| M2 | 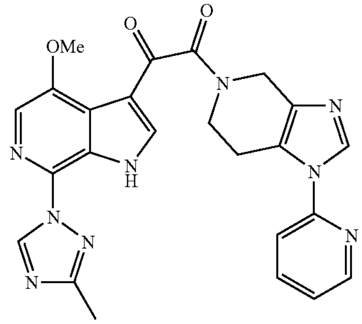 | 484 | 484, Rf = 1.15 min (Method 1). ¹H NMR (500 MHz, DMSO-d₆): δppm 12.47 (s, 1 H), 9.24 (s, 1 H) 8.9-8.78 (m, 1 H) 8.60-8.58 (m, 1 H), 8.31-8.28 (m, 1 H), 8.11-8.08 (m, 1 H), 7.88-7.80 (m, 2 H) 7.54-7.51 (m, 1 H) 4.78-4.53 (m, 2 H), 4.01-3.73 (m, 3 H), 3.84 (s, 3 H), 2.5 (s, 3 H). |

Example N

Preparation of Compounds N of Formula 1

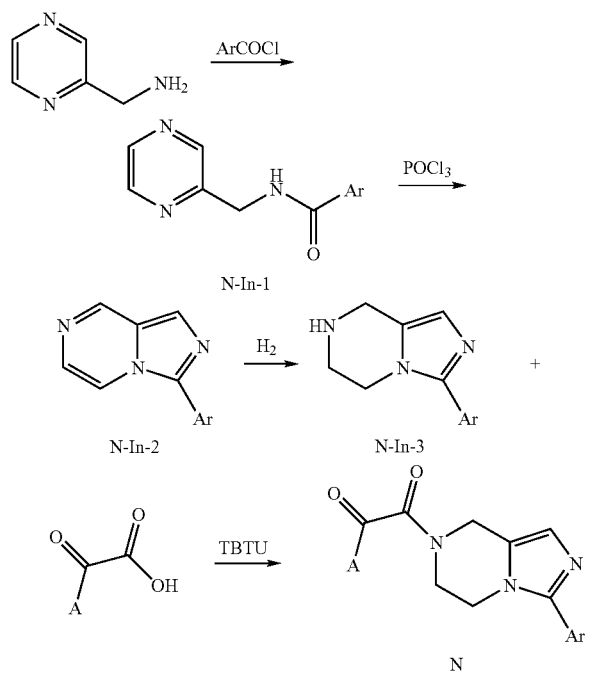

General Process for the Preparation of Compound N—In-1 from Pyrazin-2-ylmethanamine:

To a solution of 2-(aminomethyl)pyrazine dihydrochloride (1 eq.) [prepared as described by Dhar, T. G. M. et al., *Bioorg. Med. Chem. Lett.*, 17, 5019-5024 (2007)] and N,N-diisopropylethylamine (2-10 eq.) in DMF at 25° C. was added aroyl chloride (1-2 eq.), and the mixture was stirred at 25° C. for 24 h. The resulting mixture was concentrated under vacuum, and the residue was dissolved in ethyl acetate. The solution was washed with water and brine, dried over anhyd. sodium sulfate, filtered, and concentrated. Column chromatography on silica gel (elution: 0-50% ethyl acetate/methylene chloride) N—In-1.

General Process for the Preparation of Compound N—In-2 from N—In-1:

To a suspension of N—In-1 (1 eq.) in toluene at room temperature was added phosphorous oxychloride (1-10 eq.) dropwise. The resulting mixture was heated at reflux for 2.5 h. After cooling to room temperature the reaction mixture was diluted with ethyl acetate and water. The phases were separated. The aqueous phase was adjusted to pH 7 employing aqueous sodium bicarbonate solution and then extracted with ethyl acetate. The combined organic phases were washed with water and brine, dried over anhyd. sodium sulfate, filtered, and concentrated. Column chromatography on silica gel (elution: 0-5% isopropanol/chloroform) provided N—In-2.

General Process for the Preparation of Compound N—In-3 from N—In-2:

A mixture of N—In-2 (1 eq.) and 20% palladium hydroxide on carbon (0.01-0.5 eq.) in methanol was stirred at 25° C. under hydrogen gas (1.00 atm) for 26 h. The reaction mixture was filtered, and the filtrate was concentrated under vacuum to provide N—In-3.

General Process for the Preparation of Compound N from N—In-3:

2-Keto acid (1 eq.), N—In-3 (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% $NaHCO_3$ or $NH_4Cl$ aqueous solution. The aqueous layer was extracted with ethyl acetate or methylene chloride. The organic phase combined and dried over anhydrous $MgSO_4$. Concentration in vacuo provided a crude product, which was purified by trituration, or recrystallization, or silica gel column chromatography, or Shimadzu automated preparative HPLC system, to afford Compound N.

Characterization of N—In and N (Table N):

TABLE N

| Compound No. | Structure | MS (M + H)+ Calcd. | MS (M + H)+ Observ. and Retention Time and NMR |
|---|---|---|---|
| N-In-1a | 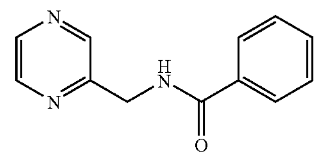 | 214 | 214.<br>$^1$H NMR (500 MHz, $CDCl_3$):<br>δ8.69 (s, 1 H), 8.53 (m, 2 H), 7.84 (m, 2 H), 7.53-7.44 (m, 3 H), 4.83 (d, 1 H, J = 4.9 Hz). |
| N-In-2a | 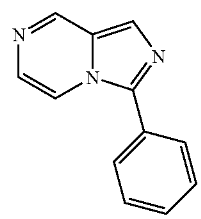 | 196 | 196. |
| N-In-3a | 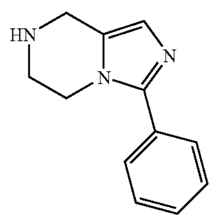 | 200 | 200. |
| N1 | 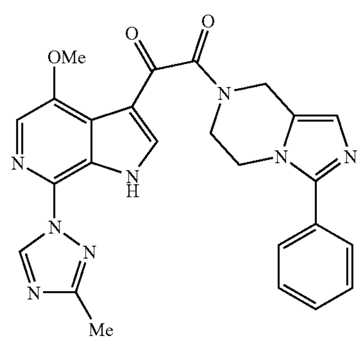 | HRMS: 483.1888 | HRMS: 483.1873.<br>$^1$H-NMR (500 MHz, DMSO-$d_6$): δ12.48 (br s, 1 H), 9.25 (s, 1 H), 8.36-8.31 (m, 1 H), 7.90 (m, 1 H), 7.80-7.73 (m, 2 H), 7.62-7.57 (m, 3 H), 7.45 (s, ⅔ H), 7.27 (s, ⅓ H), 5.00 (s, ⅔ H), 4.84 (s, ⅔ H), 4.41 (m, ⅔ H), 4.26 (m, ⅔ H), 4.05 (m, ⅔ H), 3.92 (s, 1 H), 3.88 (s, 2 H), 3.86 (m, ⅔ H), 2.50 (s, 3 H). |
| N2 | 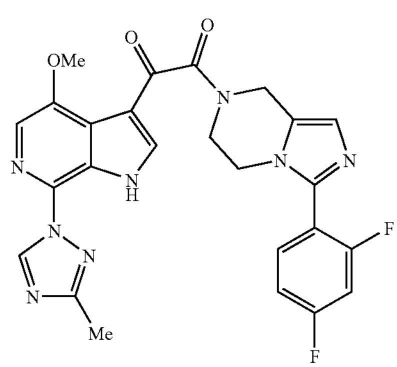 | HRMS: 519.1699 | HRMS: 519.1689.<br>$^1$H-NMR (500 MHz, DMSO-$d_6$): δ12.46 (br s, 1 H), 9.24 (s, 1 H), 8.34-8.30 (m, 1 H), 7.88-7.86 (m, 1 H), 7.69-7.60 (m, 1 H), 7.50-7.40 (m, 1 H), 7.29-7.21 (m, 1 H), 7.10 (s, ⅔ H), 6.94 (s, ⅓ H), 4.96 (s, ⅔ H), 4.79 (s, ⅔ H), 4.09 (m, ⅔ H), 3.98 (m, ⅔ H), 3.91 (m, ⅔ H), 3.84 (s, 1 H), 3.81 (m, ⅔ H), 3.77 (s, 2 H), 2.50 (s, 3 H). |

Example O

Preparation of Compounds O of Formula 1

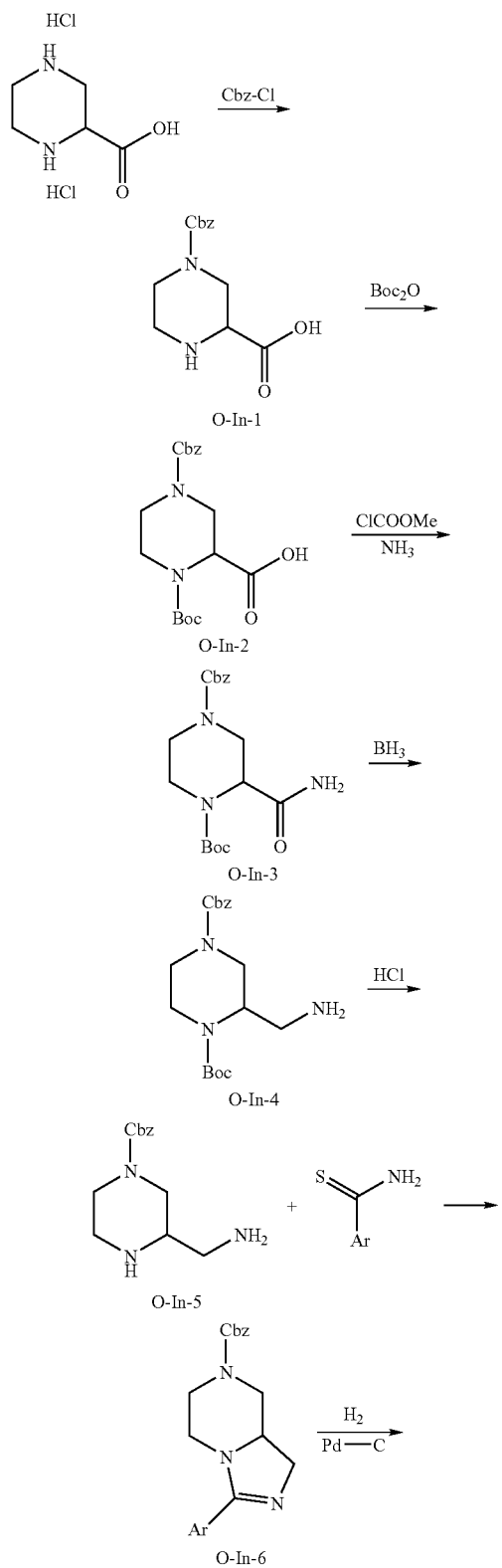

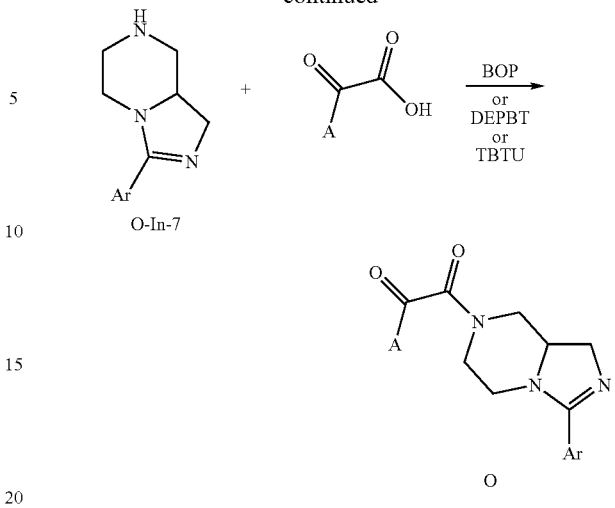

General Process for the Preparation of Compound O-In-1 from Piperazine-2-carboxylic acid:

A three necked round bottom flask was charged with piperazine-2-carboxylic acid dihydrochloride (1 eq.), cupric carbonate (1.1 eq.) and water. The reaction mixture was refluxed for about 2 h and it was filtered through CELITE® bed. The deep blue color filtrate was cooled to 0° C. and added sodium bicarbonate (3.7 eq.) into the reaction mixture very slowly. The reaction mixture was stirred at 0° C. for 30 min and benzyl chloroformate (1.5 eq.) was added to the reaction mixture very slowly. The progress of the reaction was monitored by TLC. After consumption of starting material, the reaction mixture was filtered and a pale blue solid was washed with cold water, ethanol and diethyl ether. The pale blue solid was taken up in water and concentrated hydrochloric acid was added. To this solution, $H_2S$ gas was purged for 1 h under stirring at room temperature. The excess $H_2S$ gas was removed by purging with nitrogen for 30 min. The reaction mixture was filtered through CELITE® bed and was washed with 1.5N HCl. The colorless filtrate was concentrated to afford desired O-In-1.

General Process for the Preparation of Compound O-In-2 from O-In-1:

A three necked round bottom flask was charged with O-In-1 (1 eq.), sodium hydroxide (2 eq.) and acetonitrile. The reaction mixture was cooled to 0° C. and Boc anhydride (1 eq.) was added into the reaction mixture very slowly. The reaction mixture was stirred at room temperature for 16 h. The progress of the reaction was monitored by TLC. After consumption of starting material, the reaction mixture was washed with petroleum ether. The aqueous layer was acidified with citric acid to pH~6 and extracted with dichloro methane. The combined organic layer was washed with brine solution and dried over anhydrous sodium sulfate. The organic layer was filtered and concentrated to afford O-In-2.

General Process for the Preparation of Compound O-In-3 from O-In-2:

A three necked round bottom flask was charged with O-In-2 (1 eq.), triethyl amine (2 eq.) and dry dichloromethane under nitrogen atmosphere. The reaction mixture was cooled to 0° C. and methyl chloroformate (1.3 eq.) was added into the reaction mixture very slowly. The reaction mixture was stirred at −10° C. for 30 min and further cooled to −30 ° C. Ammonia gas was purged in the reaction mixture for 30 min at −30° C. The reaction mixture was allowed to stir at room temperature for 16 h. After consumption of starting material, ice-cold water was added to reaction mixture. The organic layer was separated and aqueous layer was extracted with dichloromethane. The combined organic layers was washed with water, brine and dried over anhydrous sodium sulfate. The organic layer was filtered and concentrated under reduced pressure. The resulting crude product was purified by column chromatography using 60-120 silica gel and chloroformmethanol (6%) as eluant to afford O-In-3.

General Process for the Preparation of Compound O-In-4 from O-In-3:

A three necked round bottom flask was charged with O-In-3 (1 eq.) in dry THF under nitrogen atmosphere. The reaction mixture was cooled to 0° C. and borane-dimethyl sulphide (4 eq.) was added into the reaction mixture very slowly. The reaction mixture was allowed to stir at room temperature for 16 h. After consumption of starting material, methanol was added to the reaction mixture very slowly. The reaction mixture was stirred at room temperature for 30 min and evaporated to remove volatiles. The residue was dissolved in dichloromethane and ice cold water. The organic layer was separated and aqueous layer was extracted with dichloromethane. The combined organic layers was washed with water, brine and dried over anhydrous sodium sulfate. The organic layer was filtered and concentrated under reduced pressure. The resulting crude product was purified by column chromatography using 60-120 silica gel and chloroformmethanol (10%) as eluant to afford O-In-4.

General Process for the Preparation of Compound O-In-5 from O-In-4:

To O-In-5 dissolved in dry methanol, excess of methanolic HCl was added at 0° C. The reaction mixture was allowed to stir at room temperature for 3 h. The volatiles were completely removed under vacuum to provide O-In-5 as an HCl salt which was used in the further reactions without any purification.

General Process for the Preparation of Compound O-In-6 from O-In-5:

To O-In-5 (1 eq.) dissolved in dry triethylamine, thiobenzamide (2 eq.) was added. The reaction mixture was heated to 100° C. for 3 h. The volatiles were completely removed under vacuum and the residue was diluted with water. The aqueous layer was extracted with dichloromethane and the combined organic layer was washed with brine solution, dried over $MgSO_4$ and evaporated. The crude product was purified by column chromatography using 60-120 silica gel and chloroformmethanol (8%) as eluant to afford O-In-6.

General Process for the Preparation of Compound O-In-7 from O-In-6:

Palladium on carbon (0.01-0.5 eq.) was added into the solution of O-In-6 (1 eq.) in dry methanol under a nitrogen atmosphere. The reaction mixture was allowed to stir under a hydrogen atmosphere at 2 kg pressure for 16 h. After the completion of the reaction, the reaction mixture was filtered through a CELITE® bed and washed repeatedly with methanol. The filtrate was concentrated under vacuum to afford O-In-7.

General Process for the Preparation of Compound O from O-In-7:

2-Keto acid (1 eq.), O-In-7 (1-5 eq.), coupling agent (TBTU, DEPBT or BOP) (1-5 eq.) and Hunig's Base (1-100 eq.) were combined in DMF or THF. The mixture was stirred at room temperature for 17 hours. DMF or THF was removed via evaporation at reduced pressure and the residue was partitioned between ethyl acetate and 5-10% $Na_2CO_3$ or 5% $NaHCO_3$ or $NH_4Cl$ aqueous solution. The aqueous layer was extracted with ethyl acetate or methylene chloride. The organic phase combined and dried over anhydrous $MgSO_4$. Concentration in vacuo provided a crude product, which was purified by trituration, or recrystallization, or silica gel column chromatography, or Shimadzu automated preparative HPLC system, to afford Compound O.

Characterization of O-In and O (Table O):

TABLE O

| Compound No. | Structure | MS (M + H)+ Calcd. | MS (M + H)+ Observ. and Retention Time and NMR |
|---|---|---|---|
| O-In-1 | Cbz-piperazine-COOH | 265 | 265. $^1$H NMR (400 MHz, DMSO-$d_6$): δ3.24 (m, 2 H), 3.89 (m, 2 H), 4.14-4.20 (m, 2 H), 5.11 (m, 1 H), 7.30-7.42 (m, 5 H), 9.86 (bs, 1 H). |
| O-In-2 | Cbz/Boc-piperazine-COOH | (M − 1)+ 363 | 363 (M− 1)+. $^1$H NMR (400 MHz, DMSO-$d_6$): δ1.40 (s, 9 H), 2.94 (m, 4 H), 3.72-3.86 (m, 2 H), 4.46 (m, 2 H), 7.29-7.38 (m, 5 H), 13.2 (bs, 1 H). |
| O-In-3 | Cbz/Boc-piperazine-CONH$_2$ | 364 | $^1$H NMR (400 MHz, DMSO-$d_6$): δ1.48 (s, 9 H), 2.90 (m, 1 H), 3.15-3.18 (m, 2 H), 3.6-3.68 (m, 2 H), 3.71-3.81 (m, 2 H), 4.57-4.67 (m, 2 H), 5.07-5.10 (dd, 2 H), 7.29-7.38 (m, 5 H). |

TABLE O-continued

| Compound No. | Structure | MS (M + H)+ Calcd. | MS (M + H)+ Observ. and Retention Time and NMR |
|---|---|---|---|
| O-In-4 | Cbz-piperazine-CH2NH2, N-Boc | 350 | 350. ¹H NMR (400 MHz, DMSO-d₆): δ1.48 (s, 9 H), 2.90-3.1 (m, 2 H), 3.2-3.33 (m, 3 H), 3.6-3.68 (d, 1 H), 3.71-3.81 (dd, 1 H), 4.35-4.45 (m, 2 H), 5.05 (s, 2 H), 7.01 (bs, 1 H), 7.35-7.38 (m, 5 H). |
| O-In-5 | Cbz-piperazine-CH2NH2, NH | 250 | 250. ¹H NMR (400 MHz, DMSO-d₆): δ2.90-3.1 (m, 2 H), 3.18-3.33 (m, 3 H), 3.5-3.65 (m, 2 H), 3.94-4.02 (dd, 1 H), 4.18-4.23 (dd, 1 H), 5.05 (s, 2 H), 7.35-7.44 (m, 5 H), 8.5 (bs, 3 H), 10.12 (bs, 2 H). |
| O-In-6a | Cbz-bicyclic imidazole-phenyl | 336 | 336. ¹H NMR (400 MHz, DMSO-d₆): δ2.70-2.73 (m, 1 H), 3.11-3.18 (m, 2 H), 3.58-3.63 (m, 2 H), 3.75-3.80 (m, 2 H), 4.18-4.22 (m, 2 H), 5.05 (s, 2 H), 7.35-7.50 (m, 10 H). |
| O-In-6b | Cbz-bicyclic imidazole-pyridyl | 337 | 337. ¹H NMR (400 MHz, DMSO-d₆): δ3.18 -3.23 (m, 3 H), 3.41-3.58 (m, 2 H), 3.6-3.65 (m, 2 H), 4.10-4.14 (m, 2 H), 5.05 (s, 2 H), 7.35-7.44 (m, 5 H), 7.7 (m, 1 H), 8.02-8.03 (m, 1 H), 8.48-8.50 (d, 1 H), 8.65-8.66 (d, 1 H). |
| O-In-7a | H-bicyclic imidazole-phenyl | 202 | 202. ¹H NMR (400 MHz, DMSO-d₆): δ3.05-3.10 (m, 2 H), 3.21-3.28 (m, 2 H), 3.58-3.65 (m, 2 H), 3.70-3.73 (m, 1 H), 3.9-4.04 (m, 2 H), 7.36-7.5 (m, 5 H). |
| O-In-7b | H-bicyclic imidazole-pyridyl | 203 | 203. ¹H NMR (400 MHz, DMSO-d₆): δ3.2-3.40 (m, 3 H), 3.51-3.60 (m, 2 H), 3.6-3.65 (m, 2 H), 4.0-4.04 (m, 2 H), 7.7 (m, 1 H), 8.02-8.03 (m, 1 H), 8.48-8.50 (d, 1 H), 8.65-8.66 (d, 1 H). |

TABLE O-continued

| Compound No. | Structure | MS (M + H)+ Calcd. | MS (M + H)+ Observ. and Retention Time and NMR |
|---|---|---|---|
| O1 | 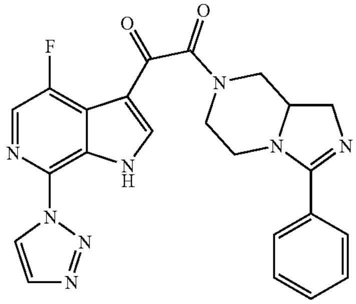 | 459 | 459. $^1$H NMR (400 MHz, DMSO-$d_6$): δ2.6 (m, 2 H), 2.85-2.95 (m, 2 H), 3.10-3.15 (m, 1 H), 3.5-3.69 (m, 4 H), 3.8-4.01 (m, 2 H), 4.17-4.43 (m, 3 H), 4.47 (dd, 1 H), 7.17 (m, 1 H), 7.40-7.60 (m, 2 H), 7.70-7.97 (m, 3 H), 8.04-8.09 (dd, 1 H), 8.17-8.25 (m, 1 H), 8.29-8.32 (dd, 1 H), 9.03 (m, 1 H). |
| O2 | 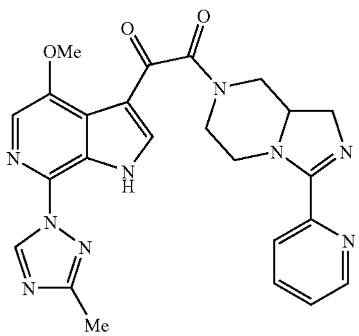 | 486 | 486. $^1$H NMR (400 MHz, DMSO-$d_6$): δ2.4 (s, 3 H), 3.11-3.13 (m, 1 H), 3.49-3.59 (m, 3 H), 3.6-3.69 (m, 1 H), 4.01 (s, 3 H), 4.17-4.43 (d, 2 H), 4.47 (dd, 1 H), 7.77 (m, 1 H), 7.89-7.90 (d, 1 H), 7.96-7.97 (m, 1 H), 8.14-8.27 (m, 1 H), 8.27-8.29 (d, 1 H), 8.80-8.9 (dd, 1 H), 9.23 (s, 1 H), 12.5 (bs, 1 H). |

Biology Data for the Examples

"μM" means micromolar
"mL" means milliliter
"μl" means microliter
"mg" means milligram The materials and experimental procedures used to obtain the results reported in Tables 1-2 are described below.

Cells:
Virus production—Human embryonic Kidney cell line, 293T, was propagated in Dulbecco's Modified Eagle Medium (Invitrogen, Carlsbad, Calif.) containing 10% fetal Bovine serum (FBS, Sigma, St. Louis, Mo.).

Virus infection—Human epithelial cell line, HeLa, expressing the HIV-1 receptor CD4 was propagated in Dulbecco's Modified Eagle Medium (Invitrogen, Carlsbad, Calif.) containing 10% fetal Bovine serum (FBS, Sigma, St. Louis, Mo.) and supplemented with 0.2 mg/mL GENETICIN® (Invitrogen, Carlsbad, Calif.).

Virus—Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al., Ref. 41). Transfections were performed using Lipofectamine Plus reagent as described by the manufacturer (Invitrogen, Carlsbad, Calif.).

Experimental Procedure:
1. HeLa CD4 cells were plated in 96 well plates at a cell density of $1\times10^4$ cells per well in 100 μl Dulbecco's Modified Eagle Medium containing 10% fetal Bovine serum and incubated overnight.
2. Compound was added in a 2 μl dimethylsulfoxide solution, so that the final assay concentration would be ≦10 μM.
3. 100 μl of single-round infectious reporter virus in Dulbecco's Modified Eagle Medium was then added to the plated cells and compound at an approximate multiplicity of infection (MOI) of 0.01, resulting in a final volume of 200 μl per well.
4. Virally-infected cells were incubated at 37° C., in a $CO_2$ incubator, and harvested 72 h after infection.
5. Viral infection was monitored by measuring luciferase expression from viral DNA in the infected cells using a luciferase reporter gene assay kit, as described by the manufacturer (Roche Molecular Biochemicals, Indianapolis, Ind.). Infected cell supernatants were removed and 50 μl of lysis buffer was added per well. After 15 minutes, 50 μl of freshly-reconstituted luciferase assay reagent was added per well. Luciferase activity was then quantified by measuring luminescence using a Wallac MICROBETA® scintillation counter.
6. The percent inhibition for each compound was calculated by quantifying the level of luciferase expression in cells infected in the presence of each compound as a percentage of that observed for cells infected in the absence of compound and subtracting such a determined value from 100.

7. An $EC_{50}$ provides a method for comparing the antiviral potency of the compounds of this disclosure. The effective concentration for fifty percent inhibition ($EC_{50}$) was calculated with the Microsoft Excel Xlfit curve fitting software. For each compound, curves were generated from percent inhibition calculated at 10 different concentrations by using a four parameter logistic model (model 205). The $EC_{50}$ data for the compounds is shown in Table 2. Table 1 is the key for the data in Table 2.

Results

TABLE 1

Biological Data Key for $EC_{50}$s

| Compounds with $EC_{50}$s >0.5 μM | Compounds with $EC_{50}$ <0.5 μM |
|---|---|
| Group "B" | Group "A" |

TABLE 2

| Compound No. | Structure | $EC_{50}$ Group from Table 1 |
|---|---|---|
| A1 | 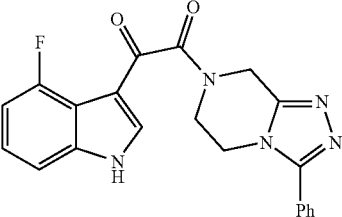 | 217 nM |
| B1 | 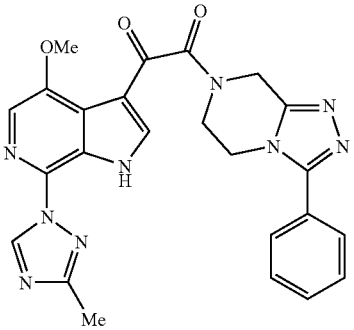 | 0.95 nM |
| B2 | 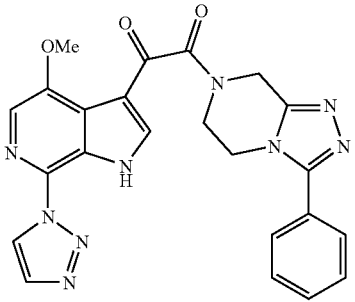 | A |
| B3 | 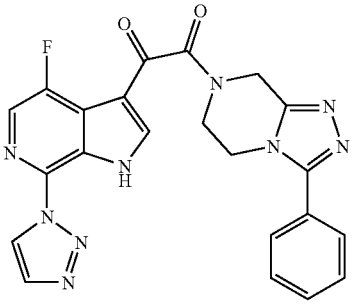 | A |

TABLE 2-continued

| Compound No. | Structure | EC$_{50}$ Group from Table 1 |
|---|---|---|
| B4 | 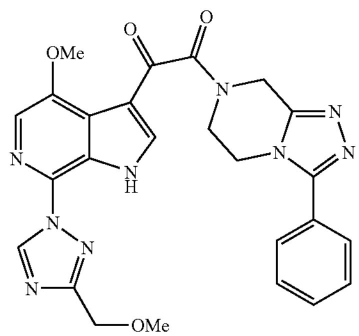 | A |
| C1 | 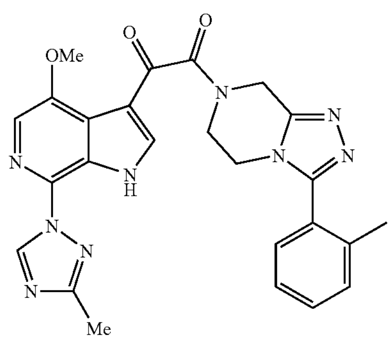 | 11.8 nM |
| C2 | 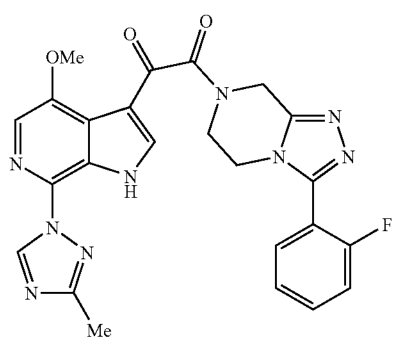 | 0.29 nM |
| C3 | 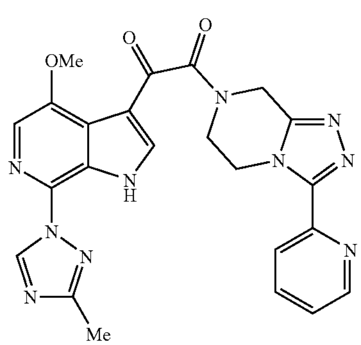 | A |

TABLE 2-continued

| Compound No. | Structure | EC$_{50}$ Group from Table 1 |
|---|---|---|
| C4 | 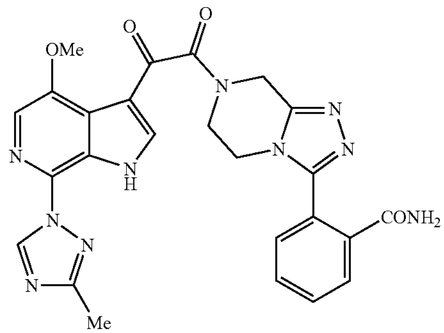 | >500 nM |
| C5 | 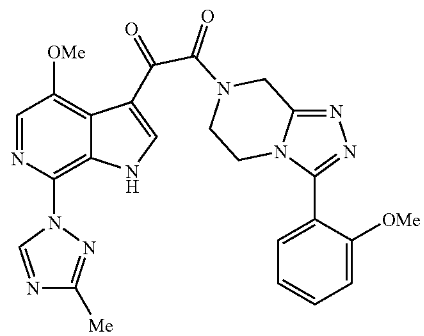 | A |
| C6 | 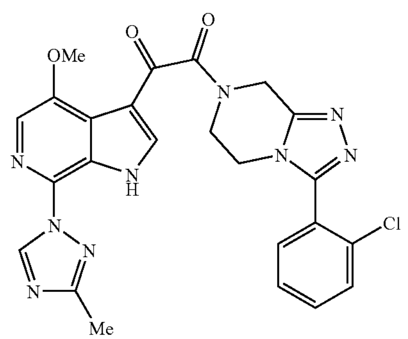 | A |
| C7 | 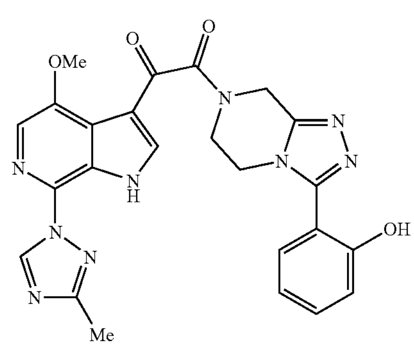 | 1.91 nM |

TABLE 2-continued

| Compound No. | Structure | EC$_{50}$ Group from Table 1 |
| --- | --- | --- |
| C8 | 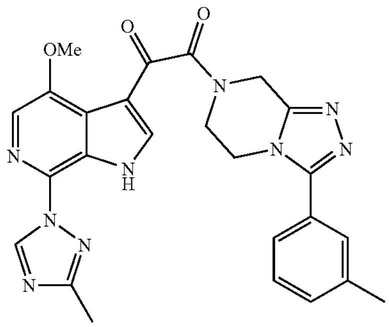 | A |
| D1 | 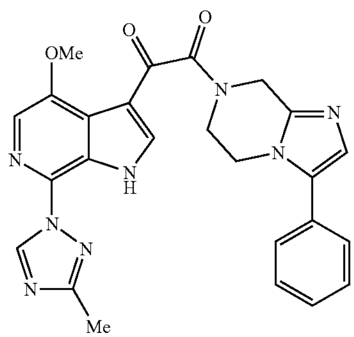 | A |
| D2 | 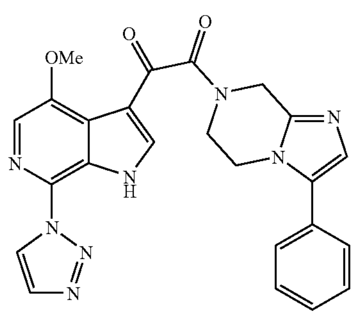 | 0.05 nM |
| D3 | 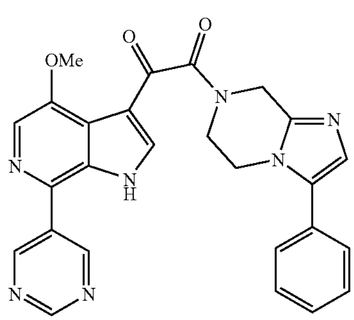 | A |

TABLE 2-continued

| Compound No. | Structure | EC$_{50}$ Group from Table 1 |
|---|---|---|
| E1 | 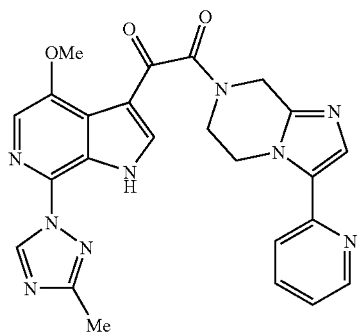 | A |
| F1 | 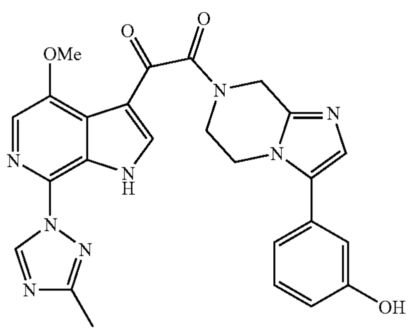 | A |
| F2 | 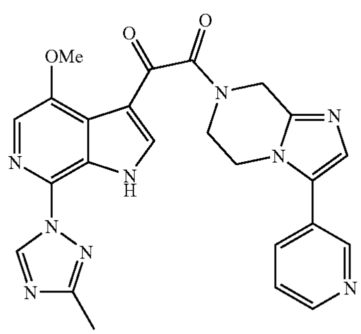 | A |
| F3 | 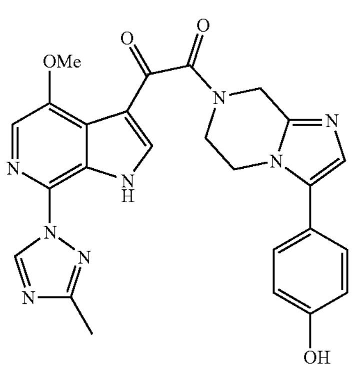 | A |

TABLE 2-continued

| Compound No. | Structure | EC$_{50}$ Group from Table 1 |
|---|---|---|
| F4 | 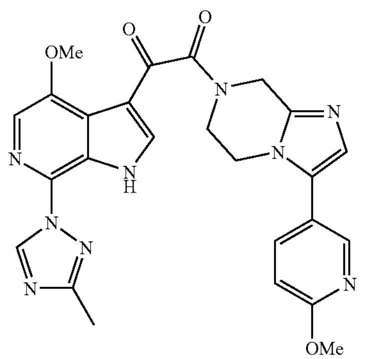 | A |
| F5 | 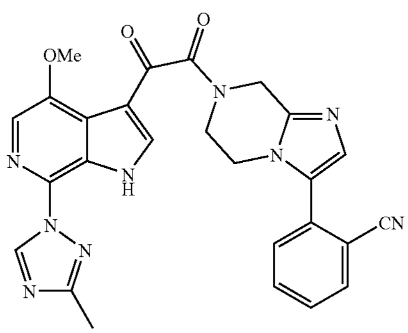 | 98.9 nM |
| F6 | 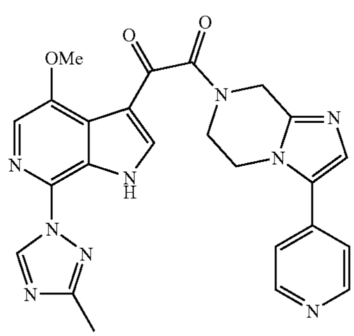 | 13.6 nM |
| G1 | 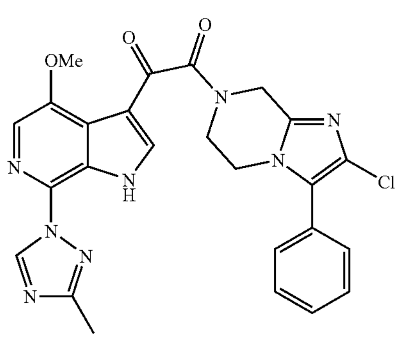 | A |

TABLE 2-continued
| Compound No. | Structure | EC$_{50}$ Group from Table 1 |
|---|---|---|
| G2 | 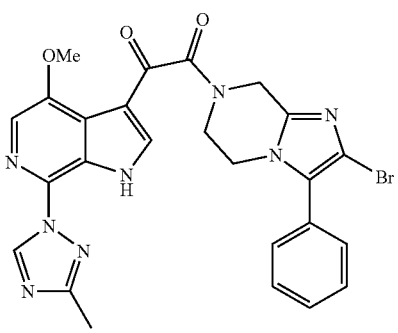 | A |
| H1a | 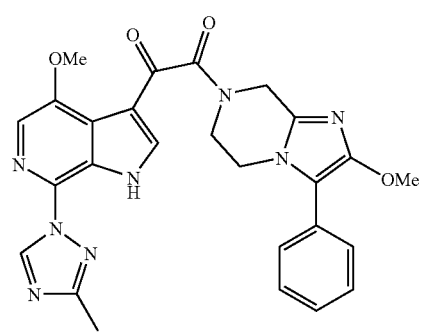 | A |
| H1b | 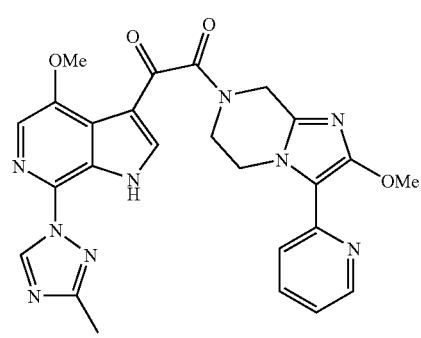 | A |
| H2 | 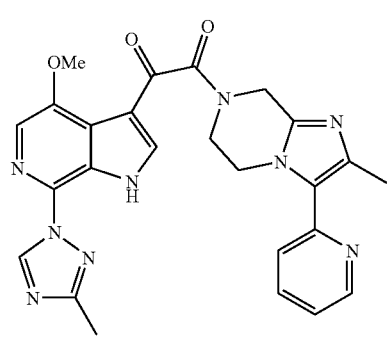 | 1 nM |

TABLE 2-continued
| Compound No. | Structure | EC$_{50}$ Group from Table 1 |
|---|---|---|
| I1 | 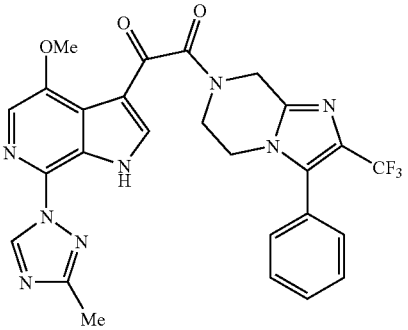 | A |
| I2 | 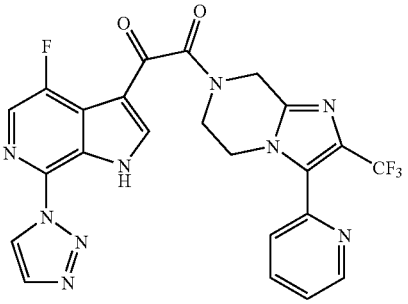 | A |
| I3 | 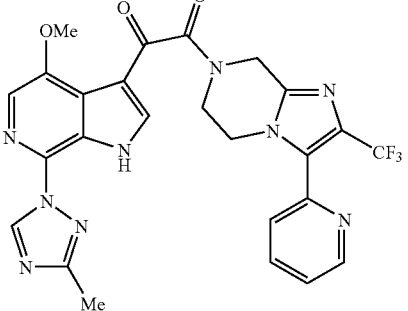 | 0.59 nM |
| J1 | 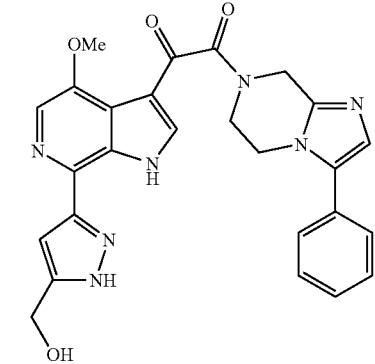 | 0.05 nM |

TABLE 2-continued

| Compound No. | Structure | EC$_{50}$ Group from Table 1 |
| --- | --- | --- |
| J2 | 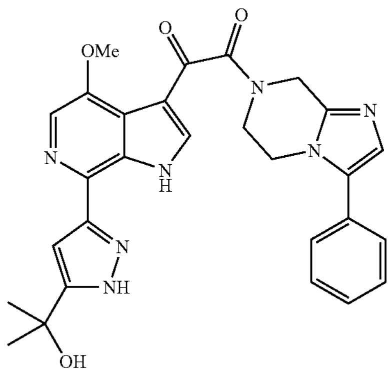 | A |
| K1 | 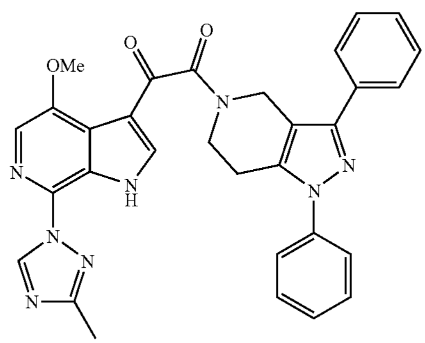 | 2.6 nM |
| L1 | 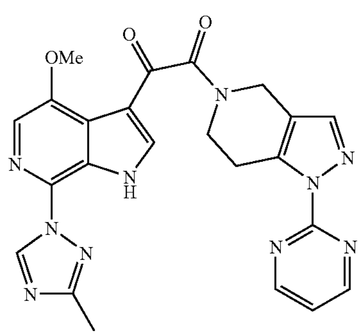 | A |
| L2 | 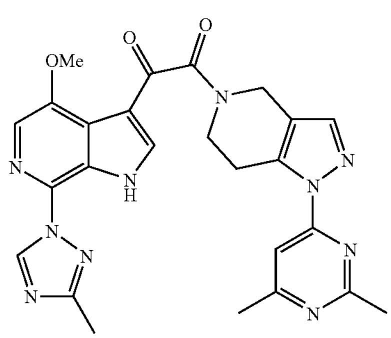 | 331 nM |

TABLE 2-continued

| Compound No. | Structure | EC$_{50}$ Group from Table 1 |
|---|---|---|
| L3 | 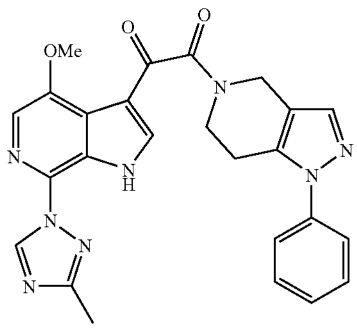 | 0.03 nM |
| L4 | 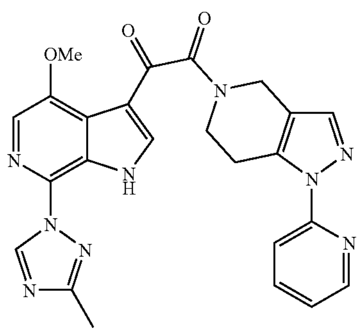 | A |
| L5 | 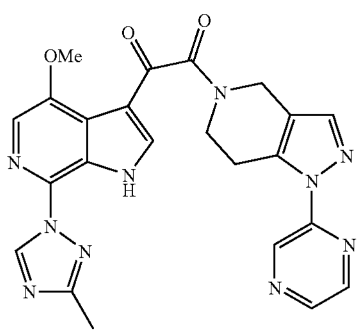 | A |
| M1 | 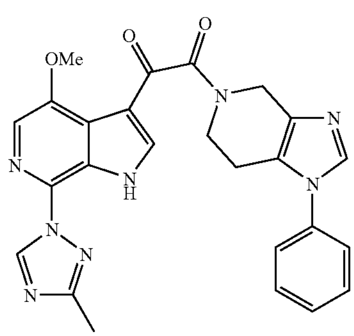 | 0.07 nM |

TABLE 2-continued

| Compound No. | Structure | EC$_{50}$ Group from Table 1 |
|---|---|---|
| M2 | 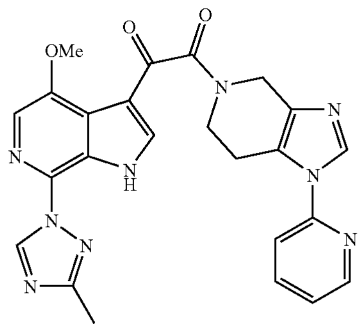 | A |
| N1 | 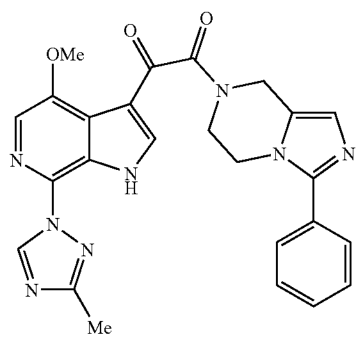 | 0.06 nM |
| N2 | 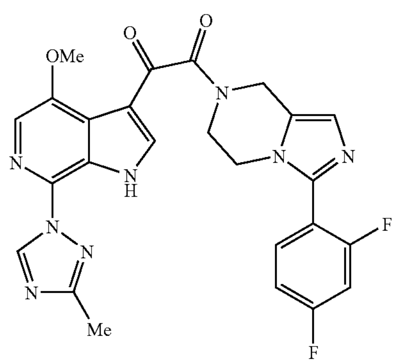 | A |
| O1 | 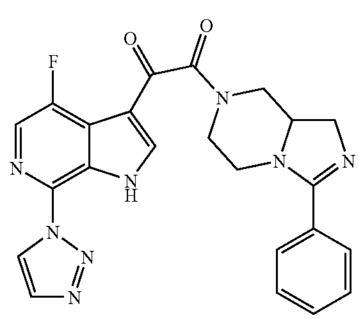 | 13 nM |

TABLE 2-continued

| Compound No. | Structure | EC$_{50}$ Group from Table 1 |
|---|---|---|
| O2 | 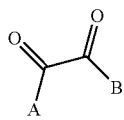 | A |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound of Formula I, including pharmaceutically acceptable salts thereof:

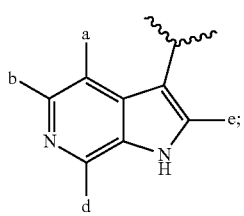

I wherein A is

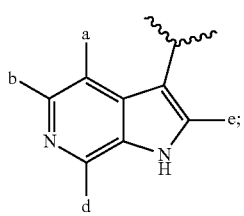

wherein B is

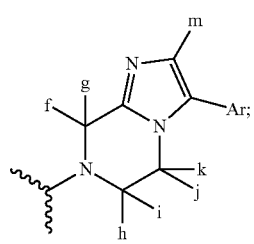

and further wherein
a is methoxy;
b is H;
d is selected from Group C;
e is H;
f and g are H;
h and i are H;
j and k are H;
m is H;
Ar is phenyl; wherein said phenyl is independently optionally substituted with one to three same or different halogens or from one to three same or different substituents selected from Group E;
Group C is triazolyl;
Group E is selected from the group consisting of OH and CN.

2. A compound which is selected from the group consisting of:

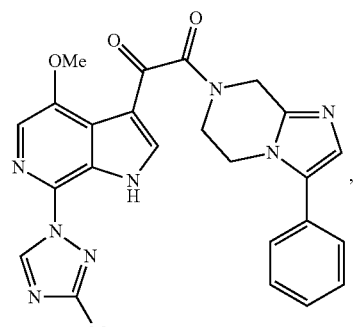

,

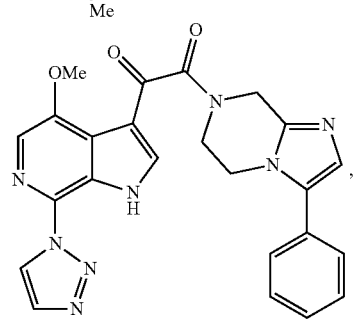

,

151
-continued

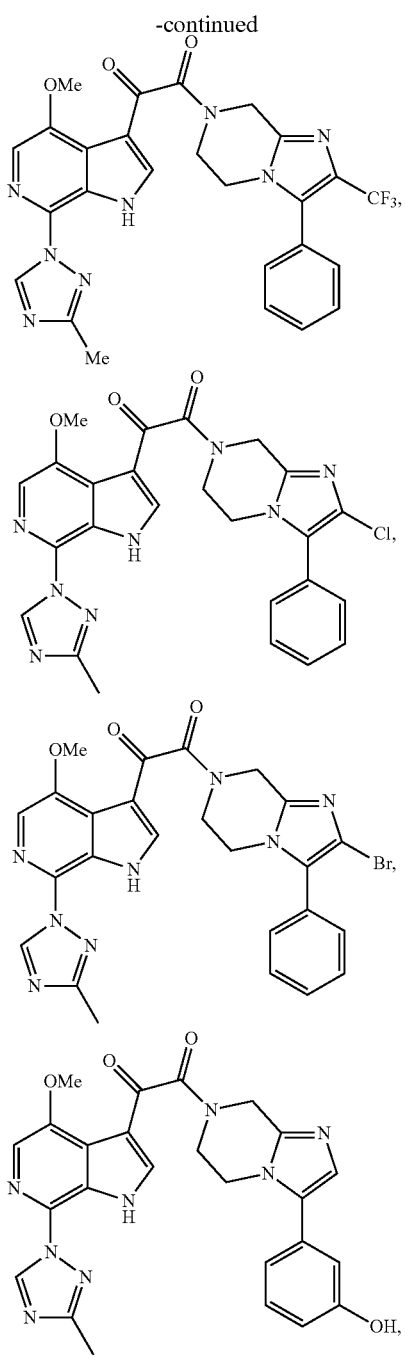

152
-continued

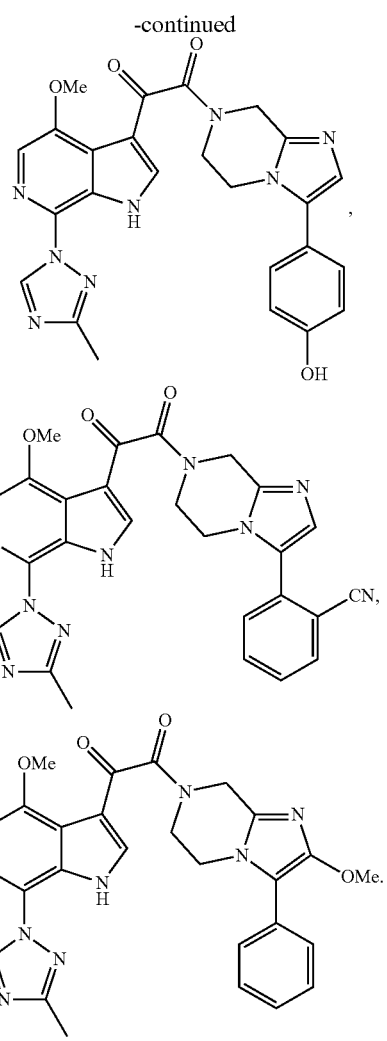

3. A pharmaceutical composition which comprises an antiviral effective amount of one or more of the compounds of Formula I as claimed in claim 1, together with one or more pharmaceutically acceptable carriers, excipients or diluents.

4. A pharmaceutical composition which comprises an antiviral effective amount of one or more of the compounds of Formula I as claimed in claim 2, together with one or more pharmaceutically acceptable carriers, excipients or diluents.

* * * * *